(12) United States Patent
Eksioglu

US012264184B2

(10) Patent No.: US 12,264,184 B2
(45) Date of Patent: Apr. 1, 2025

(54) DAP12 CONSTRUCTS AND THEIR USE TO ENHANCE DC VACCINES AND IMMUNOTHERAPIES

(71) Applicant: H. LEE MOFFITT CANCER CENTER AND RESEARCH INSTITUTE, INC., Tampa, FL (US)

(72) Inventor: Erika A. Eksioglu, Tampa, FL (US)

(73) Assignee: H. Lee Moffitt Cancer Center and Research Institute, Inc., Tampa, FL (US)

( * ) Notice: Subject to any disclaimer, the term of this patent is extended or adjusted under 35 U.S.C. 154(b) by 0 days.

(21) Appl. No.: 17/678,565

(22) Filed: Feb. 23, 2022

(65) Prior Publication Data

US 2023/0062550 A1    Mar. 2, 2023

Related U.S. Application Data

(60) Provisional application No. 63/152,378, filed on Feb. 23, 2021.

(51) Int. Cl.
| | |
|---|---|
| *C07K 14/47* | (2006.01) |
| *A61K 35/15* | (2015.01) |
| *A61K 38/17* | (2006.01) |
| *A61K 39/00* | (2006.01) |
| *A61K 45/06* | (2006.01) |
| *A61P 35/00* | (2006.01) |
| *C12N 5/0783* | (2010.01) |
| *C12N 5/0784* | (2010.01) |

(52) U.S. Cl.
CPC ...... *C07K 14/4705* (2013.01); *A61K 38/1709* (2013.01); *A61K 39/4615* (2023.05); *A61K 39/4622* (2023.05); *A61K 39/46449* (2023.05); *A61K 45/06* (2013.01); *A61P 35/00* (2018.01); *C12N 5/0636* (2013.01); *C12N 5/0639* (2013.01); *A61K 2239/31* (2023.05); *A61K 2239/38* (2023.05); *A61K 2239/57* (2023.05); *C12N 2501/998* (2013.01)

(58) Field of Classification Search
CPC ............. C07K 14/4705; A61K 35/15; A61K 38/1709; A61K 45/06; A61P 35/00; C12N 5/0636; C12N 5/0639; C12N 2501/998; C12N 2510/00
USPC ....................................................... 514/19.3
See application file for complete search history.

(56) References Cited

FOREIGN PATENT DOCUMENTS

EP        3656851 A1 *  5/2020  ............ A61K 35/17

OTHER PUBLICATIONS

Lewis L. Lanier , DAP10- and DAP12-associated receptors in innate immunity, Immunol Rev. Jan. 2009 ; 227(1).*
Youssef Fikri, Cloning, sequencing, and cell surface expression pattern of bovine immunoreceptor NKG2D and adaptor molecules DAP10 and DAP12, Immunogenetics (2007) 59:653-659.*
www.genome.gov; definition of vector, accessed on May 20, 2024.*
Anguille, S.; Smits, E.L.; Cools, N.; Goossens, H.; Berneman, Z.N.; Van Tendeloo, V.F. Short-term cultured, interleukin-15 differentiated dendritic cells have potent immunostimulatory properties. J Transl Med 2009, 7, 109, doi: 10.1186/1479-5876-7-109.
Ardavin, C.; Martinez del Hoyo, G.; Martin, P.; Anjuere, F.; Arias, C.F.; Marin, A.R.; Ruiz, S.; Parrillas, V.; Hernandez, H. Origin and differentiation of dendritic cells. Trends in immunology 2001, 22, 691-700.
Baggiolini, M.; Loetscher, P. Chemokines in inflammation and immunity. Immunology today 2000, 21, 418-420, doi: 10.1016/s0167-5699(00)01672-8.
Bakker, A.B.; Hoek, R.M.; Cerwenka, A.; Blom, B.; Lucian, L.; McNeil, T.; Murray, R.; Phillips, L.H.; Sedgwick, J.D.; Lanier, L.L. DAP12-deficient mice fail to develop autoimmunity due to impaired antigen priming. Immunity 2000, 13, 345-353, doi:10.1016/s1074-7613(00)00034-0.
Barrow, A.D.; Trowsdale, J. You say ITAM and I say ITIM, let's call the whole thing off: the ambiguity of immunoreceptor signalling. European journal of immunology 2006, 36, 1646-1653, doi:10.1002/eji.200636195.
Berk, E.; Xu, S.; Czerniecki, B.J. Dendritic cells matured in the presence of TLR ligands overcome the immunosuppressive functions of regulatory T cells. Oncoimmunology 2014, 3, e27617, doi:10.4161/onci.27617.
Billadeau, D.D.; Leibson, P.J. ITAMs versus ITIMs: striking a balance during cell regulation. The Journal of clinical investigation 2002, 109, 161-168, doi: 10.1172/JCI14843.
Bouchon, A.; Facchetti, F.; Weigand, M.A.; Colonna, M. TREM-1 amplifies inflammation and is a crucial mediator of septic shock. Nature 2001, 410, 1103-1107, doi:10.1038/3507411435074114 [pii].
Bouchon, A.; Hernandez-Munain, C.; Cella, M.; Colonna, M. A DAP12-mediated pathway regulates expression of CC chemokine receptor 7 and maturation of human dendritic cells. The Journal of experimental medicine 2001, 194, 1111-1122.
Chen, B.; Zhou, M.; Zhang, H.; Wang, C.; Hu, X.; Wang, B.; Wang, E. TREM1/Dap12-based CAR-T cells show potent antitumor activity. Immunotherapy 2019, 11, 1043-1055, doi:10.2217/imt-2019-0017.
Chen, X.; Bai, F.; Sokol, L.; Zhou, J.; Ren, A.; Painter, J.S.; Liu, J.; Sallman, D.A.; Chen, Y.A.; Yoder, J.A., et al. A critical role for DAP10 and DAP12 in CD8+ T cell-mediated tissue damage in large granular lymphocyte leukemia. Blood 2008.

(Continued)

*Primary Examiner* — Julie Ha
*Assistant Examiner* — Erinne R Dabkowski
(74) *Attorney, Agent, or Firm* — Meunier Carlin & Curfman LLC

(57) ABSTRACT

Disclosed are modified DAP12 and methods of their use for enhancing immune responses and for treating cancer.

23 Claims, 14 Drawing Sheets

Figure 1B:
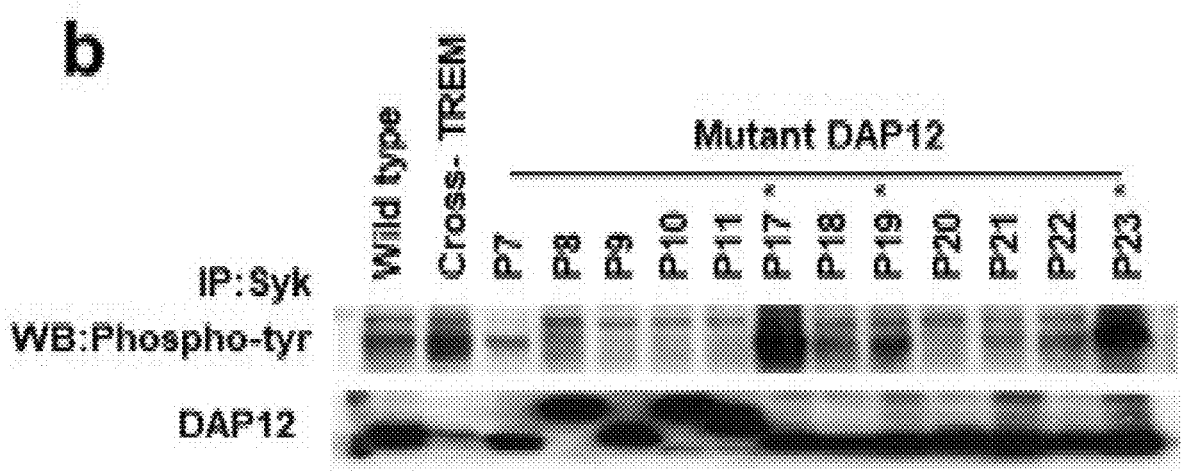

Specification includes a Sequence Listing.

(56) References Cited

OTHER PUBLICATIONS

Chen, X.; Eksioglu, E.A.; Carter, J.D.; Fortenbery, N.; Donatelli, S.S.; Zhou, J.; Liu, J.; Yang, L.; Gilvary, D.; Djeu, J., et al. Inactivation of DAP12 in PMN inhibits TREM1-mediated activation in rheumatoid arthritis. PloS one 2015, 10, e0115116, doi:10.1371/journal.pone.0115116.

Chen, X.; Eksioglu, E.A.; Zhou, J.; Zhang, L.; Djeu, J.; Fortenbery, N.; Epling-Burnette, P.; Van Bijnen, S.; Dolstra, H.; Cannon, J., et al. Induction of myelodysplasia by myeloid-derived suppressor cells. The Journal of clinical investigation 2013, 123, 4595-4611, doi:10.1172/JCI67580.

Chen, X.; Eksioglu, E.A.; Zhou, J.; Zhang, L.; Djeu, J.; Fortenbery, N.; Epling- Burnette, P.; Van Bijnen, S.; Dolstra, H.; Cannon, J., et al. Induction of myelodysplasia by myeloid-derived suppressor cells. The Journal of clinical investigation 2013, 10.1172/JCI67580, doi:10.1172/JCI67580.

Davids, M.S.; Burger, J.A. Cell Trafficking in Chronic Lymphocytic Leukemia. Open journal of hematology 2012, 3, doi:10.13055/ojhmt_3_s1 03.120221.

De Vries, I.J.; Krooshoop, D.J.; Scharenborg, N.M.; Lesterhuis, W.J.; Diepstra, J.H.; Van Muijen, G.N.; Strijk, S.P.; Ruers, T.J.; Boerman, O.C.; Oyen, W.J., et al. Effective migration of antigen-pulsed dendritic cells to lymph nodes in melanoma patients is determined by their maturation state. Cancer Res 2003, 63, 12-17.

Dhodapkar, M.V.; Steinman, R.M.; Krasovsky, J.; Munz, C.; Bhardwaj, N. Antigen-specific inhibition of effector T cell function in humans after injection of immature dendritic cells. The Journal of experimental medicine 2001, 193, 233-238.

Donatelli, S.S.; Zhou, J.M.; Gilvary, D.L.; Eksioglu, E.A.; Chen, X.; Cress, W.D.; Haura, E.B.; Schabath, M.B.; Coppola, D.; Wei, S., et al. TGF-beta-inducible microRNA-183 silences tumor-associated natural killer cells. Proc Natl Acad Sci U S A 2014, 111, 4203-4208, doi:10.1073/pnas.1319269111.

Eksioglu, E.A.; Eisen, S.; Reddy, V. Dendritic cells as therapeutic agents against cancer. Frontiers in bioscience 2010, 15, 321-347.

Eksioglu, E.A.; Kielbasa, J.; Eisen, S.; Reddy, V. Granulocyte-macrophage colony-stimulating factor increases the proportion of circulating dendritic cells after autologous but not after allogeneic hematopoietic stem cell transplantation. Cytotherapy 2011, 13, 888-896, doi:10.3109/14653249.2011.579956.

Fasbender, F.; Claus, M.; Wingert, S.; Sandusky, M.; Watzl, C. Differential Requirements for Src-Family Kinases in SYK or ZAP70-Mediated SLP-76 Phosphorylation in Lymphocytes. Frontiers in immunology 2017, 8, 789, doi:10.3389/fimmu.2017.00789.

Fontes, J.A.; Barin, J.G.; Talor, M.V.; Stickel, N.; Schaub, J.; Rose, N.R.; Cihakova, D. Complete Freund's adjuvant induces experimental autoimmune myocarditis by enhancing IL-6 production during initiation of the immune response. Immun Inflamm Dis 2017, 5, 163-176, doi:10.1002/iid3.155.

Giordano, D.; Magaletti, D.M.; Clark, E.A. Nitric oxide and cGMP protein kinase (cGK) regulate dendritic-cell migration toward the lymph-node-directing chemokine CCL19. Blood 2006, 107, 1537-1545, doi:10.1182/blood-2005-07-2901.

Gmyrek, G.B.; Akilesh, H.M.; Graham, D.B.; Fuchs, A.; Yang, L.; Miller, M.J.; Sandoval, G.J.; Sheehan, K.C.; Schreiber, R.D.; Diamond, M.S., et al. Loss of DAP12 and FcRgamma drives exaggerated IL-12 production and CD8(+) T cell response by CCR2(+) Mo-DCs. PloS one 2013, 8, e76145, doi:10.1371/journal.pone.0076145.

Graham, D.B.; Stephenson, L.M.; Lam, S.K.; Brim, K.; Lee, H.M.; Bautista, J.; Gilfillan, S.; Akilesh, S.; Fujikawa, K.; Swat, W. An ITAM-signaling pathway controls cross-presentation of particulate but not soluble antigens in dendritic cells. The Journal of experimental medicine 2007, 204, 2889-2897, doi:10.1084/jem.20071283.

Heizmann, B.; Reth, M.; Infantino, S. Syk is a dual-specificity kinase that self-regulates the signal output from the B-cell antigen receptor. Proceedings of the National Academy of Sciences 2010, 107, 18563-18568, doi:10.1073/pnas.1009048107.

Hinshaw, D.C.; Shevde, L.A. The Tumor Microenvironment Innately Modulates Cancer Progression. Cancer Res 2019, 79, 4557-4566, doi:10.1158/0008-5472.CAN-18-3962.

Hiscott, J.; Pitha, P.; Genin, P.; Nguyen, H.; Heylbroeck, C.; Mamane, Y.; Algarte, M.; Lin, R. Triggering the interferon response: the role of IRF-3 transcription factor. Journal of interferon & cytokine research : the official journal of the International Society for Interferon and Cytokine Research 1999, 19, 1-13, doi:10.1089/107999099314360.

Ivanov, S.; Scallan, J.P.; Kim, K.W.; Werth, K.; Johnson, M.W.; Saunders, B.T.; Wang, P.L.; Kuan, E.L.; Straub, A.C.; Ouhachi, M., et al. CCR7 and IRF4-dependent dendritic cells regulate lymphatic collecting vessel permeability. The Journal of clinical investigation 2016, 126, 1581-1591, doi:10.1172/JCI84518.

Jakus, Z.; Fodor, S.; Abram, C.L.; Lowell, C.A.; Mocsai, A. Immunoreceptor-like signaling by beta 2 and beta 3 integrins. Trends in cell biology 2007, 17, 493-501, doi:10.1016/j.tcb.2007.09.001.

Jonuleit, H.; Kuhn, U.; Muller, G.; Steinbrink, K.; Paragnik, L.; Schmitt, E.; Knop, J.; Enk, A.H. Pro-inflammatory cytokines and prostaglandins induce maturation of potent immunostimulatory dendritic cells under fetal calf serum-free conditions. European journal of immunology 1997, 27, 3135-3142, doi:10.1002/eji.1830271209.

Kilpelainen, P.T.; Hietala, O.A. Mutation of aspartate-233 to valine in mouse ornithine decarboxylase reduces enzyme activity. The international journal of biochemistry & cell biology 1998, 30, 803-809.

Kluckova, K.; Kozak, J.; Szaboova, K.; Rychly, B.; Svajdler, M.; Suchankova, M.; Tibenska, E.; Filova, B.; Steno, J.; Matejcik, V., et al. TREM-1 and TREM-2 Expression on Blood Monocytes Could Help Predict Survival in High-Grade Glioma Patients. Mediators of inflammation 2020, 2020, 1798147, doi:10.1155/2020/1798147.

Lanier, L.L. DAP10- and DAP12-associated receptors in innate immunity. Immunological reviews 2009, 227, 150-160, doi:10.1111/j.1600-065X.2008.00720.x.

Lanier, L.L. NK cell recognition. Annu Rev Immunol 2005, 23, 225-274.

Lanier, L.L.; Bakker, A.B. The ITAM-bearing transmembrane adaptor DAP12 in lymphoid and myeloid cell function. Immunology today 2000, 21, 611-614.

Lanier, L.L.; Corliss, B.C.; Wu, J.; Leong, C.; Phillips, J.H. Immunoreceptor DAP12 bearing a tyrosine-based activation motif is involved in activating NK cells. Nature 1998, 391, 703-707, doi:10.1038/35642.

Laufer, J.M.; Kindinger, I.; Artinger, M.; Pauli, A.; Legler, D.F. CCR7 Is Recruited to the Immunological Synapse, Acts as Co-stimulatory Molecule and Drives LFA-1 Clustering for Efficient T Cell Adhesion Through ZAP70. Frontiers in immunology 2019, 9, doi:10.3389/fimmu.2018.03115.

Ma, Y.; Adjemian, S.; Mattarollo, S.R.; Yamazaki, T.; Aymeric, L.; Yang, H.; Portela Catani, J.P.; Hannani, D.; Duret, H.; Steegh, K., et al. Anticancer chemotherapy-induced intratumoral recruitment and differentiation of antigen-presenting cells. Immunity 2013, 38, 729-741, doi:10.1016/j.immuni.2013.03.003.

Michielsen, A.J.; Hogan, A.E.; Marry, J.; Tosetto, M.; Cox, F.; Hyland, J.M.; Sheahan, K.D.; O'Donoghue, D.P.; Mulcahy, H.E.; Ryan, E.J., et al. Tumour tissue microenvironment can inhibit dendritic cell maturation in colorectal cancer. PloS one 2011, 6, e27944, doi:10.1371/journal.pone.0027944.

Mildner, A.; Jung, S. Development and function of dendritic cell subsets. Immunity 2014, 40, 642-656, doi:10.1016/j.immuni.2014.04.016.

Mocsai, A.; Humphrey, M.B.; Van Ziffle, J.A.; Hu, Y.; Burghardt, A.; Spusta, S.C.; Majumdar, S.; Lanier, L.L.; Lowell, C.A.; Nakamura, M.C. The immunomodulatory adapter proteins DAP12 and Fc receptor gamma-chain (FcRgamma) regulate development of functional osteoclasts through the Syk tyrosine kinase. Proc Natl Acad Sci U S A 2004, 101, 6158-6163, doi:10.1073/pnas.0401602101.

(56) References Cited

OTHER PUBLICATIONS

Palucka, K.; Banchereau, J. Dendritic-cell-based therapeutic cancer vaccines. Immunity 2013, 39, 38-48, doi:10.1016/j.immuni.2013.07.004.

Pinheiro da Silva, F.; Aloulou, M.; Benhamou, M.; Monteiro, R.C. Inhibitory ITAMs: a matter of life and death. Trends in immunology 2008, 29, 366-373, doi:10.1016/j.it.2008.05.001 S1471-4906(08)00155-5 [pii].

Ravetch, J.V.; Lanier, L.L. Immune inhibitory receptors. Science 2000, 290, 84-89.

Reis e Sousa, C. Dendritic cells in a mature age. Nature reviews. Immunology 2006, 6, 476-483, doi:10.1038/nri1845.

Ribas, A.; Glaspy, J.A.; Lee, Y.; Dissette, V.B.; Seja, E.; Vu, H.T.; Tchekmedyian, N.S.; Oseguera, D.; Comin-Anduix, B.; Wargo, J.A., et al. Role of dendritic cell phenotype, determinant spreading, and negative costimulatory blockade in dendritic cell-based melanoma immunotherapy. Journal of immunotherapy 2004, 27, 354-367.

Ris-Stalpers, C.; Trifiro, M.A.; Kuiper, G.G.; Jenster, G.; Romalo, G.; Sai, T.; van Rooij, H.C.; Kaufman, M.; Rosenfield, R.L.; Liao, S., et al. Substitution of aspartic acid-686 by histidine or asparagine in the human androgen receptor leads to a functionally inactive protein with altered hormone-binding characteristics. Molecular endocrinology 1991, 5, 1562-1569, doi:10.1210/mend-5-10-1562.

Sedlik, C.; Orbach, D.; Veron, P.; Schweighoffer, E.; Colucci, F.; Gamberale, R.; Ioan-Facsinay, A.; Verbeek, S.; Ricciardi-Castagnoli, P.; Bonnerot, C., et al. A critical role for Syk protein tyrosine kinase in Fc receptor-mediated antigen presentation and induction of dendritic cell maturation. Journal of immunology 2003, 170, 846-852.

Sjolin, H.; Robbins, S.H.; Bessou, G.; Hidmark, A.; Tomasello, E.; Johansson, M.; Hall, H.; Charifi, F.; Karlsson Hedestam, G.B.; Biron, C.A., et al. DAP12 signaling regulates plasmacytoid dendritic cell homeostasis and down-modulates their function during viral infection. Journal of immunology 2006, 177, 2908-2916.

Tawab, A.; Fan, Y.; Read, E.J.; Kurlander, R.J. Effect of ex vivo culture duration on phenotype and cytokine production by mature dendritic cells derived from peripheral blood monocytes. Transfusion 2009, 49, 536-547, doi:10.1111/j.1537-2995.2008.02020.x.

Trakatelli, M.; Toungouz, M.; Blocklet, D.; Dodoo, Y.; Gordower, L.; Laporte, M.; Vereecken, P.; Sales, F.; Mortier, L.; Mazouz, N., et al. A new dendritic cell vaccine generated with interleukin-3 and interferon-beta induces CD8+ T cell responses against NA17-A2 tumor peptide in melanoma patients. Cancer Immunol Immunother 2006, 55, 469-474, doi:10.1007/s00262-005-0056-z.

Turnbull, I.R.; McDunn, J.E.; Takai, T.; Townsend, R.R.; Cobb, J.P.; Colonna, M. DAP12 (KARAP) amplifies inflammation and increases mortality from endotoxemia and septic peritonitis. The Journal of experimental medicine 2005, 202, 363-369, doi:10.1084/jem.20050986.

Turnis, M.E.; Rooney, C.M. Enhancement of dendritic cells as vaccines for cancer. Immunotherapy 2010, 2, 847-862, doi:10.2217/imt.10.56.

Underhill, D.M.; Goodridge, H.S. The many faces of ITAMs. Trends in immunology 2007, 28, 66-73, doi:10.1016/j.it.2006.12.004.

Villadangos, J.A.; Schnorrer, P. Intrinsic and cooperative antigen-presenting functions of dendritic-cell subsets in vivo. Nature reviews. Immunology 2007, 7, 543-555, doi:10.1038/nri2103.

Zhou, W.; Freed, C.R. Tyrosine-to-cysteine modification of human alpha-synuclein enhances protein aggregation and cellular toxicity. The Journal of biological chemistry 2004, 279, 10128-10135, doi:10.1074/jbc.M307563200.

\* cited by examiner

FIG. 1A

Extracellular domain | Transmembrane domain | Cytoplasmic domain

YQELQGQRSDVYSDLNTQRPYYK

| Name | Sequence |
|---|---|
| | YQELQGQRSDVYSDLNTQRPYYK (ITAM sequence) |
| Wild type DAP12 | IRLLAVYFLGRLVPRGRAAEAATKQTITETESPYQELQGQRSDVYSDLNTQRPYYK |
| dnDAP12 | ---------------------------------------------------A¹⁰⁰--------------- |
| P7 (D100V) | ------------------------------------------------------V--------------- |
| P8 (Y97YYEE3) | ---------------------------------------E⁹⁷-----------E¹⁰²------------- |
| P9 (Y91D) | ---------------------------------------D⁹¹---------------------------- |
| P10 (Y97YYEE4) | ---------------------------------------E⁹⁷-----------E¹⁰²------------- |
| P11 (Y91Y102DD) | ---------------------------------------D⁹¹-----------D¹⁰²------------- |
| P17 (Y91D, D100V101VR)* | ----------------------------------------------------VR--------------- |
| P18 (D100D104HH) | -----------------------------------------------------H-----H---------- |
| P19 (D104N)* | -----------------------------------------------------------N---------- |
| P20 (Y91C) | ---------------------------------------C⁹¹---------------------------- |
| P21 (Y102C) | ------------------------------------------------------C¹⁰²------------ |
| P22 (L105Y) | ------------------------------------------------------------Y--------- |
| P23 (N108K)* | --------------------------------------------------------------K------- |

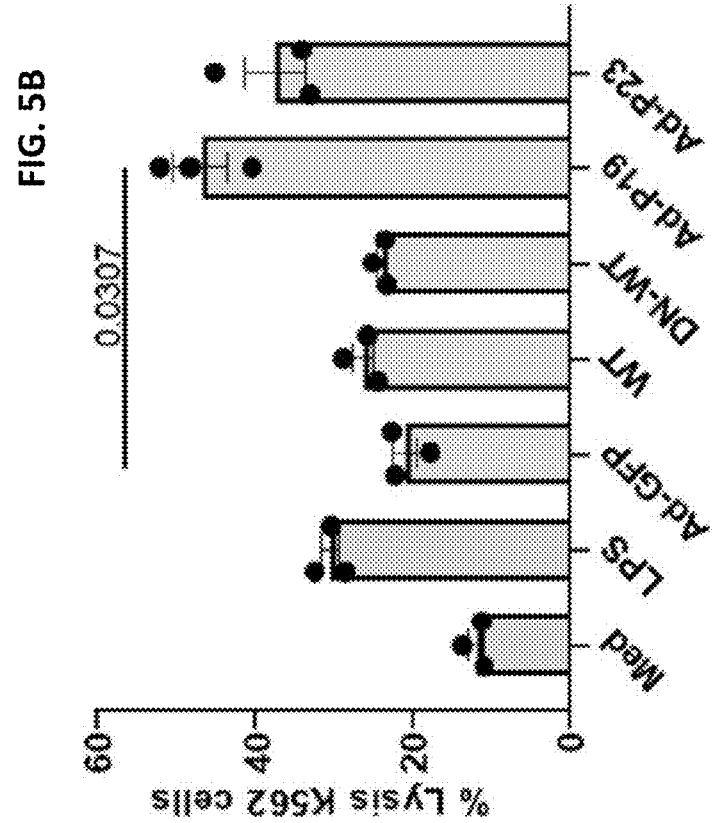
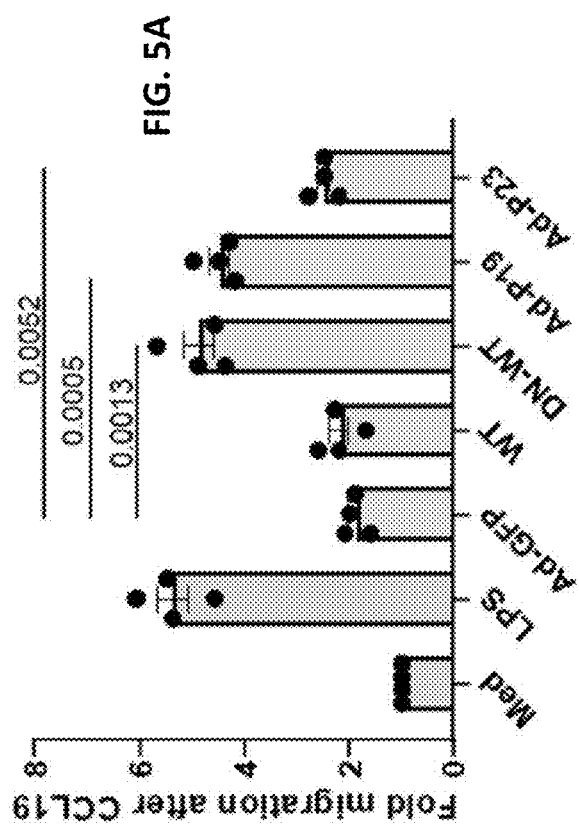
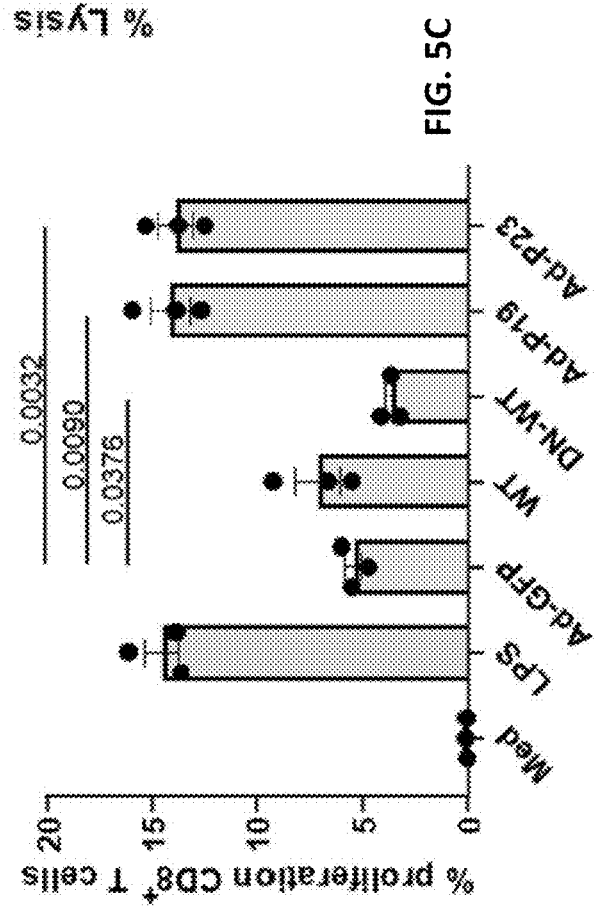

SEQUENCE LISTING

```
<160> NUMBER OF SEQ ID NOS: 40

<210> SEQ ID NO 1
<211> LENGTH: 57
<212> TYPE: PRT
<213> ORGANISM: Homo sapiens

<400> SEQUENCE: 1

Ile Ala Leu Ala Val Tyr Phe Leu Gly Arg Leu Val Pro Arg Gly Arg
1               5                   10                  15

Gly Ala Ala Glu Ala Ala Thr Arg Lys Gln Arg Ile Thr Glu Thr Glu
            20                  25                  30

Ser Pro Tyr Gln Glu Leu Gln Gly Gln Arg Ser Asp Val Tyr Ser Asp
        35                  40                  45

Leu Asn Thr Gln Arg Pro Tyr Tyr Lys
    50                  55

<210> SEQ ID NO 2
<211> LENGTH: 20
<212> TYPE: DNA
<213> ORGANISM: Artificial Sequence
<220> FEATURE:
<223> OTHER INFORMATION: Synthetic construct

<400> SEQUENCE: 2
```
aatacgactc actataggga                                                20

<210> SEQ ID NO 3
<211> LENGTH: 24
<212> TYPE: DNA
<213> ORGANISM: Artificial Sequence
<220> FEATURE:
<223> OTHER INFORMATION: Synthetic construct

<400> SEQUENCE: 3
ggacagtggg agtggcacct tcca                                           24

<210> SEQ ID NO 4
<211> LENGTH: 21
<212> TYPE: DNA
<213> ORGANISM: Artificial Sequence
<220> FEATURE:
<223> OTHER INFORMATION: Synthetic construct

<400> SEQUENCE: 4
gtagacaacc gacctctgac c                                              21

<210> SEQ ID NO 5
<211> LENGTH: 21
<212> TYPE: DNA
<213> ORGANISM: Artificial Sequence
<220> FEATURE:
<223> OTHER INFORMATION: Synthetic construct

<400> SEQUENCE: 5
aggtcggttg tctacagcga c                                              21

<210> SEQ ID NO 6
<211> LENGTH: 27
<212> TYPE: DNA
<213> ORGANISM: Artificial Sequence
<220> FEATURE:
<223> OTHER INFORMATION: Synthetic construct

<400> SEQUENCE: 6
cgctcatttg tattccggcc tctgtgc                                        27

<210> SEQ ID NO 7
<211> LENGTH: 27
<212> TYPE: DNA
<213> ORGANISM: Artificial Sequence
<220> FEATURE:
<223> OTHER INFORMATION: Synthetic construct

<400> SEQUENCE: 7
cagaggccgg aatacaaatg agcggcc                                        27

<210> SEQ ID NO 8
<211> LENGTH: 26
<212> TYPE: DNA
<213> ORGANISM: Artificial Sequence
<220> FEATURE:
<223> OTHER INFORMATION: Synthetic construct

<400> SEQUENCE: 8
accgagtcgc ctgatcagga gctcca                                         26

<210> SEQ ID NO 9
<211> LENGTH: 24
<212> TYPE: DNA

```
<213> ORGANISM: Artificial Sequence
<220> FEATURE:
<223> OTHER INFORMATION: Synthetic construct

<400> SEQUENCE: 9
gagctcctga tcaggcgact cggt                                              24

<210> SEQ ID NO 10
<211> LENGTH: 27
<212> TYPE: DNA
<213> ORGANISM: Artificial Sequence
<220> FEATURE:
<223> OTHER INFORMATION: Synthetic construct

<400> SEQUENCE: 10
cgctcatttc tcttccggcc tctgtgt                                           27

<210> SEQ ID NO 11
<211> LENGTH: 27
<212> TYPE: DNA
<213> ORGANISM: Artificial Sequence
<220> FEATURE:
<223> OTHER INFORMATION: Synthetic construct

<400> SEQUENCE: 11
cagaggccgg aagagaaatg agcggcc                                           27

<210> SEQ ID NO 12
<211> LENGTH: 24
<212> TYPE: DNA
<213> ORGANISM: Artificial Sequence
<220> FEATURE:
<223> OTHER INFORMATION: Synthetic construct

<400> SEQUENCE: 12
tcggatgtcg acagcgacct caac                                              24

<210> SEQ ID NO 13
<211> LENGTH: 24
<212> TYPE: DNA
<213> ORGANISM: Artificial Sequence
<220> FEATURE:
<223> OTHER INFORMATION: Synthetic construct

<400> SEQUENCE: 13
gtgttgaggt cgctgtcgac atcc                                              24

<210> SEQ ID NO 14
<211> LENGTH: 27
<212> TYPE: DNA
<213> ORGANISM: Artificial Sequence
<220> FEATURE:
<223> OTHER INFORMATION: Synthetic Construct

<400> SEQUENCE: 14
cagaggtcgg ttcgctacag cgacctc                                           27

<210> SEQ ID NO 15
<211> LENGTH: 27
<212> TYPE: DNA
<213> ORGANISM: Artificial Sequence
<220> FEATURE:
<223> OTHER INFORMATION: Synthetic construct

<400> SEQUENCE: 15
gtcgctgtag cgaaccgacc tctgacc                                           27
```

<210> SEQ ID NO 16
<211> LENGTH: 32
<212> TYPE: DNA
<213> ORGANISM: Artificial Sequence
<220> FEATURE:
<223> OTHER INFORMATION: Synthetic construct

<400> SEQUENCE: 16
cagaggtcgc atgtctacag ccacctcaac ac                                    32

<210> SEQ ID NO 17
<211> LENGTH: 33
<212> TYPE: DNA
<213> ORGANISM: Artificial Sequence
<220> FEATURE:
<223> OTHER INFORMATION: Synthetic construct

<400> SEQUENCE: 17
tgttgaggtg gctgtagaca tgcgacctct gac                                   33

<210> SEQ ID NO 18
<211> LENGTH: 29
<212> TYPE: DNA
<213> ORGANISM: Artificial Sequence
<220> FEATURE:
<223> OTHER INFORMATION: Synthetic construct

<400> SEQUENCE: 18
gatgtctaca gcaacctcaa cacacagag                                        29

<210> SEQ ID NO 19
<211> LENGTH: 29
<212> TYPE: DNA
<213> ORGANISM: Artificial Sequence
<220> FEATURE:
<223> OTHER INFORMATION: Synthetic construct

<400> SEQUENCE: 19
ctgtgtgttg aggttgctgt agacatccg                                        29

<210> SEQ ID NO 20
<211> LENGTH: 28
<212> TYPE: DNA
<213> ORGANISM: Artificial Sequence
<220> FEATURE:
<223> OTHER INFORMATION: Synthetic construct

<400> SEQUENCE: 20
accgagtcgc cttgtcagga gctccagg                                         28

<210> SEQ ID NO 21
<211> LENGTH: 29
<212> TYPE: DNA
<213> ORGANISM: Artificial Sequence
<220> FEATURE:
<223> OTHER INFORMATION: Synthetic construct

<400> SEQUENCE: 21
tggagctcct gacaaggcga ctcggtctc                                        29

<210> SEQ ID NO 22
<211> LENGTH: 29
<212> TYPE: DNA
<213> ORGANISM: Artificial Sequence
<220> FEATURE:

<223> OTHER INFORMATION: Synthetic construct

<400> SEQUENCE: 22
gtcggatgtc tgcagcgacc tcaacacac                                    29

<210> SEQ ID NO 23
<211> LENGTH: 28
<212> TYPE: DNA
<213> ORGANISM: Artificial Sequence
<220> FEATURE:
<223> OTHER INFORMATION: Synthetic construct

<400> SEQUENCE: 23
gttgaggtcg ctgcagacat ccgacctc                                     28

<210> SEQ ID NO 24
<211> LENGTH: 29
<212> TYPE: DNA
<213> ORGANISM: Artificial Sequence
<220> FEATURE:
<223> OTHER INFORMATION: Synthetic construct

<400> SEQUENCE: 24
gatgtctaca gcgactacaa cacacagag                                    29

<210> SEQ ID NO 25
<211> LENGTH: 28
<212> TYPE: DNA
<213> ORGANISM: Artificial Sequence
<220> FEATURE:
<223> OTHER INFORMATION: Synthetic construct

<400> SEQUENCE: 25
gcctctgtgt gttgtagtcg ctgtagac                                     28

<210> SEQ ID NO 26
<211> LENGTH: 28
<212> TYPE: DNA
<213> ORGANISM: Artificial Sequence
<220> FEATURE:
<223> OTHER INFORMATION: Synthetic construct

<400> SEQUENCE: 26
gtctacagcg acctcaaaac acagaggc                                     28

<210> SEQ ID NO 27
<211> LENGTH: 28
<212> TYPE: DNA
<213> ORGANISM: Artificial Sequence
<220> FEATURE:
<223> OTHER INFORMATION: Synthetic construct

<400> SEQUENCE: 27
cggcctctgt gttttgaggt cgctgtag                                     28

<210> SEQ ID NO 28
<211> LENGTH: 57
<212> TYPE: PRT
<213> ORGANISM: Artificial Sequence
<220> FEATURE:
<223> OTHER INFORMATION: Synthetic construct

<400> SEQUENCE: 28

Ile Ala Leu Ala Val Tyr Phe Leu Gly Arg Leu Val Pro Arg Gly Arg
1               5                   10                  15

Gly Ala Ala Glu Ala Ala Thr Arg Lys Gln Arg Ile Thr Glu Thr Glu
            20                  25                  30

Ser Pro Tyr Gln Glu Leu Gln Gly Gln Arg Ser Val Val Tyr Ser Asp
        35                  40                  45

Leu Asn Thr Gln Arg Pro Tyr Tyr Lys
    50                  55

<210> SEQ ID NO 29
<211> LENGTH: 57
<212> TYPE: PRT
<213> ORGANISM: Artificial Sequence
<220> FEATURE:
<223> OTHER INFORMATION: Synthetic construct

<400> SEQUENCE: 29

Ile Ala Leu Ala Val Tyr Phe Leu Gly Arg Leu Val Pro Arg Gly Arg
1               5                   10                  15

Gly Ala Ala Glu Ala Ala Thr Arg Lys Gln Arg Ile Thr Glu Thr Glu
            20                  25                  30

Ser Pro Glu Gln Glu Leu Gln Gly Gln Arg Ser Asp Val Glu Ser Asp
        35                  40                  45

Leu Asn Thr Gln Arg Pro Tyr Glu Lys
    50                  55

<210> SEQ ID NO 30
<211> LENGTH: 57
<212> TYPE: PRT
<213> ORGANISM: Artificial Sequence
<220> FEATURE:
<223> OTHER INFORMATION: Synthetic construct

<400> SEQUENCE: 30

Ile Ala Leu Ala Val Tyr Phe Leu Gly Arg Leu Val Pro Arg Gly Arg
1               5                   10                  15

Gly Ala Ala Glu Ala Ala Thr Arg Lys Gln Arg Ile Thr Glu Thr Glu
            20                  25                  30

Ser Pro Asp Gln Glu Leu Gln Gly Gln Arg Ser Asp Val Tyr Ser Asp
        35                  40                  45

Leu Asn Thr Gln Arg Pro Tyr Tyr Lys
    50                  55

<210> SEQ ID NO 31
<211> LENGTH: 57
<212> TYPE: PRT
<213> ORGANISM: Artificial Sequence
<220> FEATURE:
<223> OTHER INFORMATION: Synthetic construct

<400> SEQUENCE: 31

Ile Ala Leu Ala Val Tyr Phe Leu Gly Arg Leu Val Pro Arg Gly Arg
1               5                   10                  15

Gly Ala Ala Glu Ala Ala Thr Arg Lys Gln Arg Ile Thr Glu Thr Glu
            20                  25                  30

Ser Pro Glu Gln Glu Leu Gln Gly Gln Arg Ser Asp Val Glu Ser Asp
        35                  40                  45

Leu Asn Thr Gln Arg Pro Glu Glu Lys
    50                  55

<210> SEQ ID NO 32
<211> LENGTH: 57
<212> TYPE: PRT

```
<213> ORGANISM: Artificial Sequence
<220> FEATURE:
<223> OTHER INFORMATION: Synthetic construct

<400> SEQUENCE: 32

Ile Ala Leu Ala Val Tyr Phe Leu Gly Arg Leu Val Pro Arg Gly Arg
1               5                   10                  15

Gly Ala Ala Glu Ala Ala Thr Arg Lys Gln Arg Ile Thr Glu Thr Glu
            20                  25                  30

Ser Pro Asp Gln Glu Leu Gln Gly Gln Arg Ser Asp Val Asp Ser Asp
        35                  40                  45

Leu Asn Thr Gln Arg Pro Tyr Tyr Lys
    50                  55

<210> SEQ ID NO 33
<211> LENGTH: 57
<212> TYPE: PRT
<213> ORGANISM: Artificial Sequence
<220> FEATURE:
<223> OTHER INFORMATION: Synthetic construct

<400> SEQUENCE: 33

Ile Ala Leu Ala Val Tyr Phe Leu Gly Arg Leu Val Pro Arg Gly Arg
1               5                   10                  15

Gly Ala Ala Glu Ala Ala Thr Arg Lys Gln Arg Ile Thr Glu Thr Glu
            20                  25                  30

Ser Pro Tyr Gln Glu Leu Gln Gly Gln Arg Ser Val Arg Tyr Ser Asp
        35                  40                  45

Leu Asn Thr Gln Arg Pro Tyr Tyr Lys
    50                  55

<210> SEQ ID NO 34
<211> LENGTH: 57
<212> TYPE: PRT
<213> ORGANISM: Artificial Sequence
<220> FEATURE:
<223> OTHER INFORMATION: Synthetic construct

<400> SEQUENCE: 34

Ile Ala Leu Ala Val Tyr Phe Leu Gly Arg Leu Val Pro Arg Gly Arg
1               5                   10                  15

Gly Ala Ala Glu Ala Ala Thr Arg Lys Gln Arg Ile Thr Glu Thr Glu
            20                  25                  30

Ser Pro Tyr Gln Glu Leu Gln Gly Gln Arg His Asp Val Tyr Ser His
        35                  40                  45

Leu Asn Thr Gln Arg Pro Tyr Tyr Lys
    50                  55

<210> SEQ ID NO 35
<211> LENGTH: 57
<212> TYPE: PRT
<213> ORGANISM: Artificial Sequence
<220> FEATURE:
<223> OTHER INFORMATION: Synthetic construct

<400> SEQUENCE: 35

Ile Ala Leu Ala Val Tyr Phe Leu Gly Arg Leu Val Pro Arg Gly Arg
1               5                   10                  15

Gly Ala Ala Glu Ala Ala Thr Arg Lys Gln Arg Ile Thr Glu Thr Glu
            20                  25                  30

Ser Pro Tyr Gln Glu Leu Gln Gly Gln Arg Ser Asp Val Tyr Ser Asn
```

-continued

```
                35                  40                  45
Leu Asn Thr Gln Arg Pro Tyr Tyr Lys
    50                  55

<210> SEQ ID NO 36
<211> LENGTH: 57
<212> TYPE: PRT
<213> ORGANISM: Artificial Sequence
<220> FEATURE:
<223> OTHER INFORMATION: Synthetic construct

<400> SEQUENCE: 36

Ile Ala Leu Ala Val Tyr Phe Leu Gly Arg Leu Val Pro Arg Gly Arg
1               5                   10                  15

Gly Ala Ala Glu Ala Ala Thr Arg Lys Gln Arg Ile Thr Glu Thr Glu
            20                  25                  30

Ser Pro Cys Gln Glu Leu Gln Gly Gln Arg Ser Asp Val Tyr Ser Asp
        35                  40                  45

Leu Asn Thr Gln Arg Pro Tyr Tyr Lys
    50                  55

<210> SEQ ID NO 37
<211> LENGTH: 57
<212> TYPE: PRT
<213> ORGANISM: Artificial Sequence
<220> FEATURE:
<223> OTHER INFORMATION: Synthetic construct

<400> SEQUENCE: 37

Ile Ala Leu Ala Val Tyr Phe Leu Gly Arg Leu Val Pro Arg Gly Arg
1               5                   10                  15

Gly Ala Ala Glu Ala Ala Thr Arg Lys Gln Arg Ile Thr Glu Thr Glu
            20                  25                  30

Ser Pro Tyr Gln Glu Leu Gln Gly Gln Arg Ser Asp Val Cys Ser Asp
        35                  40                  45

Leu Asn Thr Gln Arg Pro Tyr Tyr Lys
    50                  55

<210> SEQ ID NO 38
<211> LENGTH: 57
<212> TYPE: PRT
<213> ORGANISM: Artificial Sequence
<220> FEATURE:
<223> OTHER INFORMATION: Synthetic construct

<400> SEQUENCE: 38

Ile Ala Leu Ala Val Tyr Phe Leu Gly Arg Leu Val Pro Arg Gly Arg
1               5                   10                  15

Gly Ala Ala Glu Ala Ala Thr Arg Lys Gln Arg Ile Thr Glu Thr Glu
            20                  25                  30

Ser Pro Tyr Gln Glu Leu Gln Gly Gln Arg Ser Asp Val Tyr Ser Asp
        35                  40                  45

Tyr Asn Thr Gln Arg Pro Tyr Tyr Lys
    50                  55

<210> SEQ ID NO 39
<211> LENGTH: 57
<212> TYPE: PRT
<213> ORGANISM: Artificial Sequence
<220> FEATURE:
<223> OTHER INFORMATION: Synthetic construct
```

```
<400> SEQUENCE: 39

Ile Ala Leu Ala Val Tyr Phe Leu Gly Arg Leu Val Pro Arg Gly Arg
1               5                   10                  15

Gly Ala Ala Glu Ala Ala Thr Arg Lys Gln Arg Ile Thr Glu Thr Glu
                20                  25                  30

Ser Pro Tyr Gln Glu Leu Gln Gly Gln Arg Ser Asp Val Tyr Ser Asp
            35                  40                  45

Leu Lys Thr Gln Arg Pro Tyr Tyr Lys
    50                  55

<210> SEQ ID NO 40
<211> LENGTH: 57
<212> TYPE: PRT
<213> ORGANISM: Artificial Sequence
<220> FEATURE:
<223> OTHER INFORMATION: Synthetic construct

<400> SEQUENCE: 40

Ile Ala Leu Ala Val Tyr Phe Leu Gly Arg Leu Val Pro Arg Gly Arg
1               5                   10                  15

Gly Ala Ala Glu Ala Ala Thr Arg Lys Gln Arg Ile Thr Glu Thr Glu
                20                  25                  30

Ser Pro Tyr Gln Glu Leu Gln Gly Gln Arg Ser Asp Val Ala Ser Asp
            35                  40                  45

Leu Asn Thr Gln Arg Pro Tyr Tyr Lys
    50                  55
```

DAP12 CONSTRUCTS AND THEIR USE TO ENHANCE DC VACCINES AND IMMUNOTHERAPIES

This Application claims the benefit of U.S. Provisional Application No. 63/152,378, filed on Feb. 23, 2021, which is incorporated herein by reference in its entirety.

REFERENCE TO SEQUENCE LISTING

The sequence listing submitted on Feb. 12, 2024, as an TXT file entitled "10110-281US1 ST25.txt" created on Feb. 12, 2024, and having a file size of 13,676 bytes is hereby incorporated by reference pursuant to 37 C.F.R. § 1.52 (e) (5).

This invention was made with government support under Grant No. K01CA187020 and P30CA076292 awarded by National Institutes of Health. The government has certain rights in the invention.

I. BACKGROUND

Dendritic cells (DCs) mediate the critical interface between innate and adaptive immunity to both microbes and neoplasia. These professional antigen presenting cells (APC) possess the unique capacity to cross-present exogenous antigens derived from tumors to generate both primary and secondary anti-tumor cytolytic responses. In particular, they play a critical role in the development of novel therapeutic strategies against cancer as DCs are among the most potent APCs of the immune system. Hence they represent a feasible, safe and promising tool in therapeutic vaccination against cancer with minimal side effects and, in some cases, high effectiveness. This last point involves the stage of activation and maturation of the DCs used, making this a critical step for DC vaccine development and one of the major hurdles in their design. In the early stage, immature DCs respond to activating stimuli through a diverse repertoire of stimulatory receptors which direct the maturation, migration, and secretion of critical pro-inflammatory mediators. However, immature cells, from which most DC vaccine therapies are derived, are not migratory or anti-tumoral preventing the migration of tumor-specific cells to the tumor site and elicitation of an effective response. This is partly due to the reduced upregulation or incomplete activation of stimulatory receptors critical for proper DC activation. What are needed are new methods and compositions that can activate DC cells and enhance immune responses.

II. SUMMARY

Disclosed are methods and compositions related to modified DAP12 peptides, polypeptides, or proteins.

In one aspect, disclosed herein are modified 12-kilodalton DNAX activating protein (DAP12) comprising one or more substitutions in the cytoplasmic domain of DAP12 as represented by SEQ ID NO: 1 (such as, for example a substitution at a residue corresponding to residues 91, 99, 100, 101, 102, 104, 105, 106, 111, or 112 of DAP12, including, but not limited to a D100V substitution; a Y91E substitution; a S99H substitution; a D100H substitution; a Y102C substitution; a Y102E substitution; a Y102D substitution; a V101R substitution; a D104H substitution; a Y111E substitution; a Y111D substitution; a Y112D substitution; a Y112E substitution; a Y91D substitution; a D104N substitution; a Y91C substitution; a L105Y substitution; and/or a N106K substitution and/or any combination thereof, including, but not limited to a Y91E, Y102E, and Y112E substitution; a Y91E, Y102E, Y111E, and Y112E substitution; a Y91D and Y102D substitution; a D100V and V101R substitution; or a S99H and a D104H substitution).

Also disclosed herein are modified DAP12 of any preceding aspect, wherein the one or more substitutions occur in the ITAM sequence (such as, for example, one or more substitutions occurs at a residue corresponding to residues 91, 99, 100, 101, 102, 104, and/or 105 of DAP12 as represented by SEQ ID NO: 1).

In one aspect, disclosed herein are modified DAP12 of any preceding aspect, wherein the one or more substitutions mimic phosphorylation, including, but not limited to modified DAP12 wherein the one or more substitutions comprise a Y91E, Y91D, Y102D, Y102E, Y111D, Y111E, Y112D, and/or Y112E substitution of DAP12 as represented by SEQ ID NO: 1.

Also disclosed herein are modified DAP12 of any preceding aspect, wherein the one or more substitutions block activation, including, but not limited modified DAP12 wherein the one or more substitutions comprise a Y91C and/or Y102C substitution of DAP12 as represented by SEQ ID NO:1.

In one aspect, disclosed herein are modified DAP12 of any preceding aspect, wherein the one or more substitutions allow normal binding with rapid dissociation, including, but not limited modified DAP12 wherein the one or more substitutions comprise a D100V or D100H substitution of DAP12 as represented by SEQ ID NO: 1.

Also disclosed herein are modified DAP12 of any preceding aspect, wherein the one or more substitutions disrupt the ITAM interaction, including, but not limited modified DAP12 wherein the one or more substitutions comprise a V101R substitution of DAP12 as represented by SEQ ID NO: 1.

In one aspect, disclosed herein are vectors (such as, for example an adenoviral vector) comprising the modified DAP12 of any preceding aspect. In some aspects, the DAP12 is under control of a constitutive promoter.

Also disclosed herein are dendritic cells comprising the modified DAP12 or vector comprising the modified DAP12 of any preceding aspect.

In one aspect disclosed herein are methods of treating, decreasing, reducing, inhibiting, ameliorating and/or preventing a cancer and/or metastasis in a subject comprising administering to the subject the modified DAP12, vector, or dendritic cell of any preceding aspect. For example, disclosed herein are methods of treating, decreasing, reducing, inhibiting, ameliorating and/or preventing a cancer and/or metastasis in a subject comprising administering to the subject a modified DAP12 comprising one or more substitutions in the cytoplasmic domain of DAP12 as represented by SEQ ID NO: 1 (such as, for example a substitution at a residue corresponding to residues 91, 99, 100, 101, 102, 104, 105, 106, 111, or 112 of DAP12, including, but not limited to D100V substitution; a Y91E substitution; a S99H substitution; a D100H substitution; a Y102C substitution; a Y102E substitution; a Y102D substitution; a V101R substitution; a D104H substitution; a Y111E substitution; a Y111D substitution; a Y112D substitution; a Y112E substitution; a Y91D substitution; a D104N substitution; a Y91C substitution; a L105Y substitution; and/or a N106K substitution and/or any combination thereof, including, but not limited to a Y91E, Y102E, and Y112E substitution; a Y91E, Y102E, Y111E, and Y112E substitution; a Y91D and Y102D substitution; a D100V and V101R substitution; or a S99H and a D104H substitution); a vector (such as, for example an adenoviral vector) comprising the modified DAP12 of any preceding aspect; or a dendritic cells comprising the modified DAP12 of any of or vector of any preceding aspect. In one aspect, the method can further comprise administering to the subject a dendritic cell (such as, for example, an autologous dendritic cell or a dendritic cell from an allogenic source), including, but not limited to a dendritic cell comprising a modified DAP12 (for example, a dendritic cell that has been transfected with the modified DAP12 or a vector encoding said modified DAP12) ex vivo.

Also disclosed herein are methods of treating, decreasing, reducing, inhibiting, ameliorating and/or preventing a cancer and/or metastasis of any preceding aspect, further comprising administering to a subject an anti-cancer immunotherapy. In one aspect, disclosed herein are methods of treating, decreasing, reducing, inhibiting, ameliorating and/or preventing a cancer and/or metastasis wherein the anti-cancer immunotherapy is administered to the subject at least 5, 10, 15, 20, 25, 30, 35, 40, 45, 50, 55, 60, 65, 70, 75, 80, 85, 90 minutes, 2, 3, 4, 5, 6, 7, 8, 9, 10, 11, 12, 13, 14, 15, 16, 17, 18, 19, 20, 21, 22, 23, 24, 25, 26, 27, 28, 29, 30, 32, 35, 36, 40, 42, 45, 48 hours, 3, 4, 5, 6, 7, 8, 9, 10, 11, 12, 13, 14, 15, 16, 17, 18, 19, 20, 21, 22, 23, 24, 25, 26, 27, 28, 29, 30, 31, 45, 58, 59, 60, 61 days, 3, 4, 5, 6, 7, 8, 9, 10, 11, 12 months following administration of the modified DAP12.

In one aspect, disclosed herein are methods of promoting activation of dendritic cells comprising contacting a dendritic cell with the modified DAP12 or vector of any preceding aspect.

Also disclosed herein are methods of inducing maturation of dendritic cells comprising contacting a dendritic cell with the modified DAP12 or vector of any preceding aspect.

In one aspect, disclosed herein are methods of activating T cells comprising contacting the T cells with the modified DAP12, vector, or the dendritic cell of any preceding aspect.

Also disclosed herein are methods of stimulating the proliferation of T cells comprising contacting the T cells with the modified DAP12, vector, or the dendritic cell of any preceding aspect.

In one aspect, disclosed herein are methods of enhancing an anti-cancer immunotherapy in a subject comprising administering to the subject the modified DAP12, vector, or dendritic cell of any preceding aspect at least 5, 10, 15, 20, 25, 30, 35, 40, 45, 50, 55, 60, 65, 70, 75, 80, 85, 90 minutes, 2, 3, 4, 5, 6, 7, 8, 9, 10, 11, 12, 13, 14, 15, 16, 17, 18, 19, 20, 21, 22, 23, 24, 25, 26, 27, 28, 29, 30, 32, 35, 36, 40, 42, 45, 48 hours, 3, 4, 5, 6, 7, 8, 9, 10, 11, 12, 13, 14, 15, 16, 17, 18, 19, 20, 21, 22, 23, 24, 25, 26, 27, 28, 29, 30, 31, 45, 58, 59, 60, 61 days, 3, 4, 5, 6, 7, 8, 9, 10, 11, 12 months prior to administration of the anti-cancer immunotherapy.

Also disclosed herein are methods of inducing SYK activation in monocyte derived dendritic cells (Mo-DC) comprising contacting the Mo-DC with the modified DAP12 and/or the vector of any preceding aspect.

III. BRIEF DESCRIPTION OF THE DRAWINGS

The accompanying drawings, which are incorporated in and constitute a part of this specification, illustrate several embodiments and together with the description illustrate the disclosed compositions and methods.

Figure 1C:
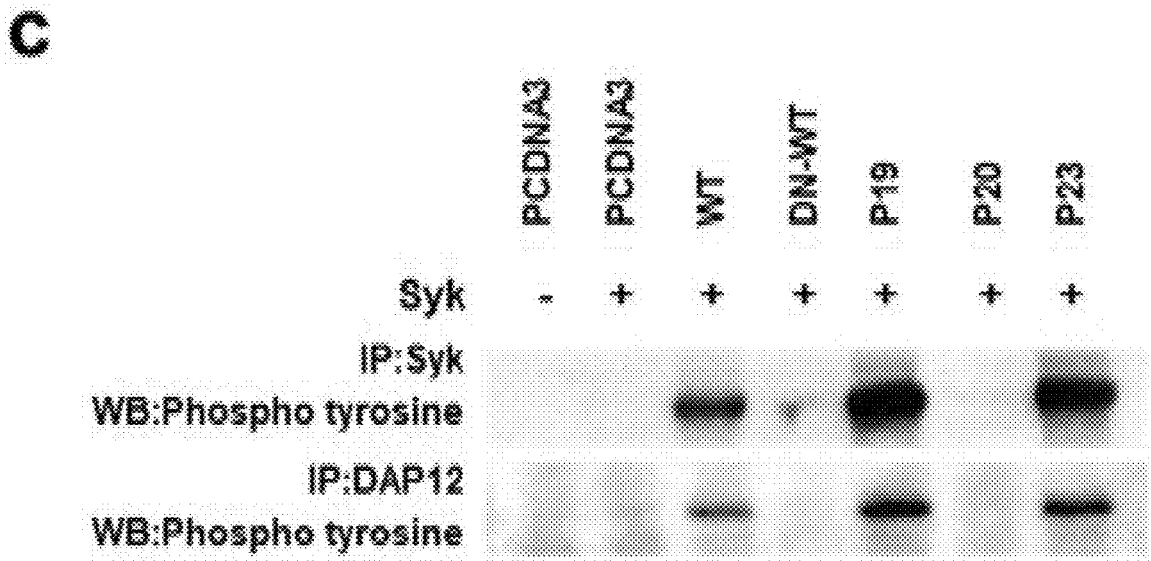
Figures 1D, 1E:
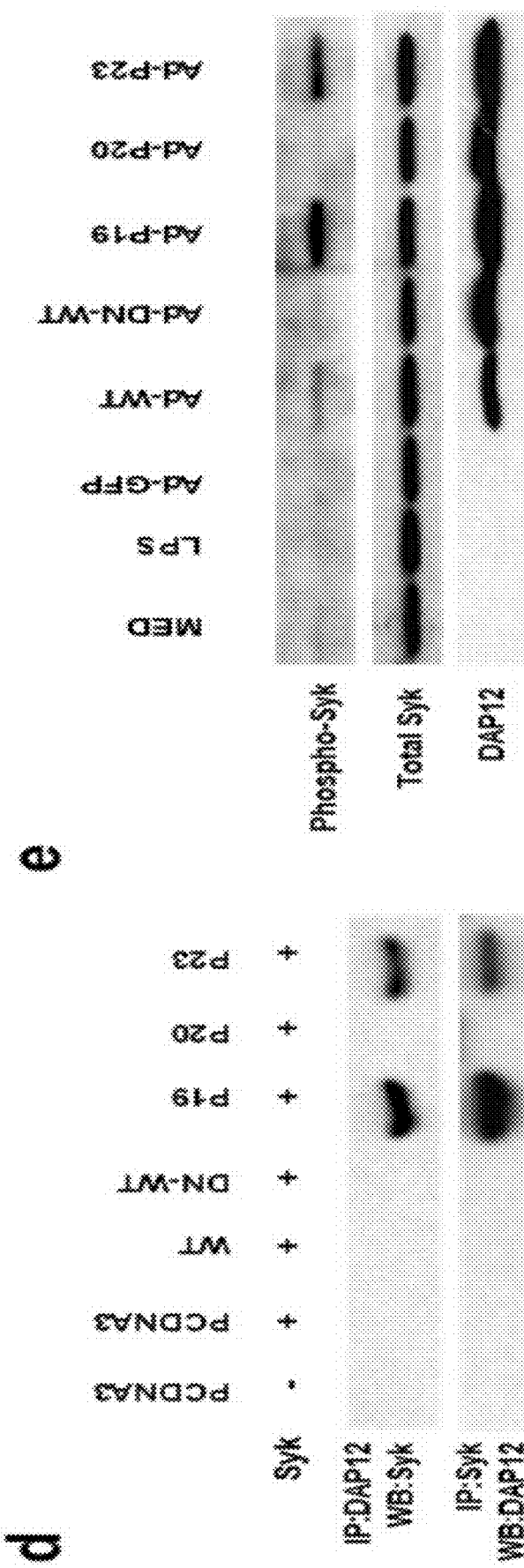

FIGS. 1A, 1B, 1C, 1D, and 1E show that constitutively active DAP12 associates with and activates Syk in AD293 cells: FIG. 1A shows a schematic representation of DAP12 (showing residues 91-113 of SEQ ID NO: 1) and a sequence alignment of the wildtype sequence SEQ ID NO:1) and mutations described herein (dnDAP12 (SEQ ID NO: 40) P7 (SEQ ID NO: 28), P8 (SEQ ID NO: 29), P9 (SEQ ID NO: 30), P10 (SEQ ID NO: 31), P11 (SEQ ID NO: 32), P17 (SEQ ID NO: 33), P18 (SEQ ID NO: 34), P19 (SEQ ID NO: 35), P20 (SEQ ID NO: 36), P21 (SEQ ID NO: 37), P22 (SEQ ID NO: 38), and P23 (SEQ ID NO: 39)); (1B) Immunoblot analysis of Syk tyrosine phosphorylation in Syk-overexpressing-AD293 cells transfected with wild-type (WT), dominant negative (dn) DAP12 or mutant DAP12 (P7, P8, P9, P10, P11, P17, P18, P19, P20, P21, P22 and P23) and detected by a pan-phospho-Tyrosine antibody (4G10). Cross-linking of TREM1 in WT DAP12 transfected cells serves as a positive control for Syk activation; (1C) AD293 cells were co-transfected with pcDNA3-Syk and either WT or mutant DAP12 (P19, P20 and P23) were IP for Syk or DAP12 and WB with anti-phospho-Tyrosine antibody; (1D) Co-immunoprecipitation of DAP12 and Syk. IP, of either Syk or DAP12, to assess the association of DAP12 and Syk respectively. FIG. 1E shows human MoDCs were transduced with Ad constructs containing either: GFP, WT DAP12, DN-WT, P19, P20, P23, or LPS (2 µg/mL) for 48 prior to WB for Syk Tyr525/526, total Syk or DAP12. Untreated cells (MED) or LPS treated cells are also shown.

Figure 2:
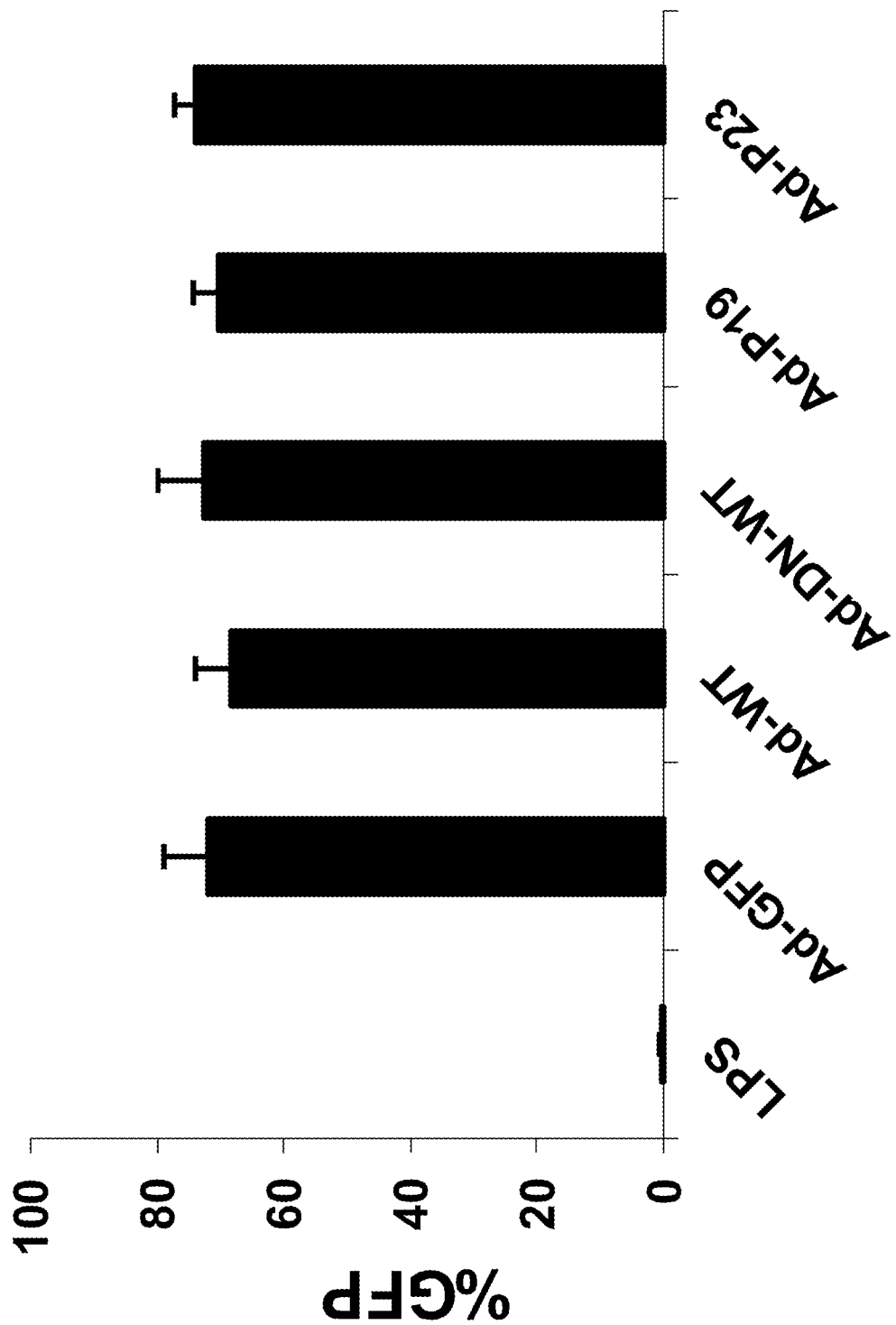

FIG. 2 shows flow cytometric analysis of GFP expression in transduced primary Mo-DC transduced with adenovirus as shown. LPS is the positive control for the experiment not transduced.

Figure 3A:
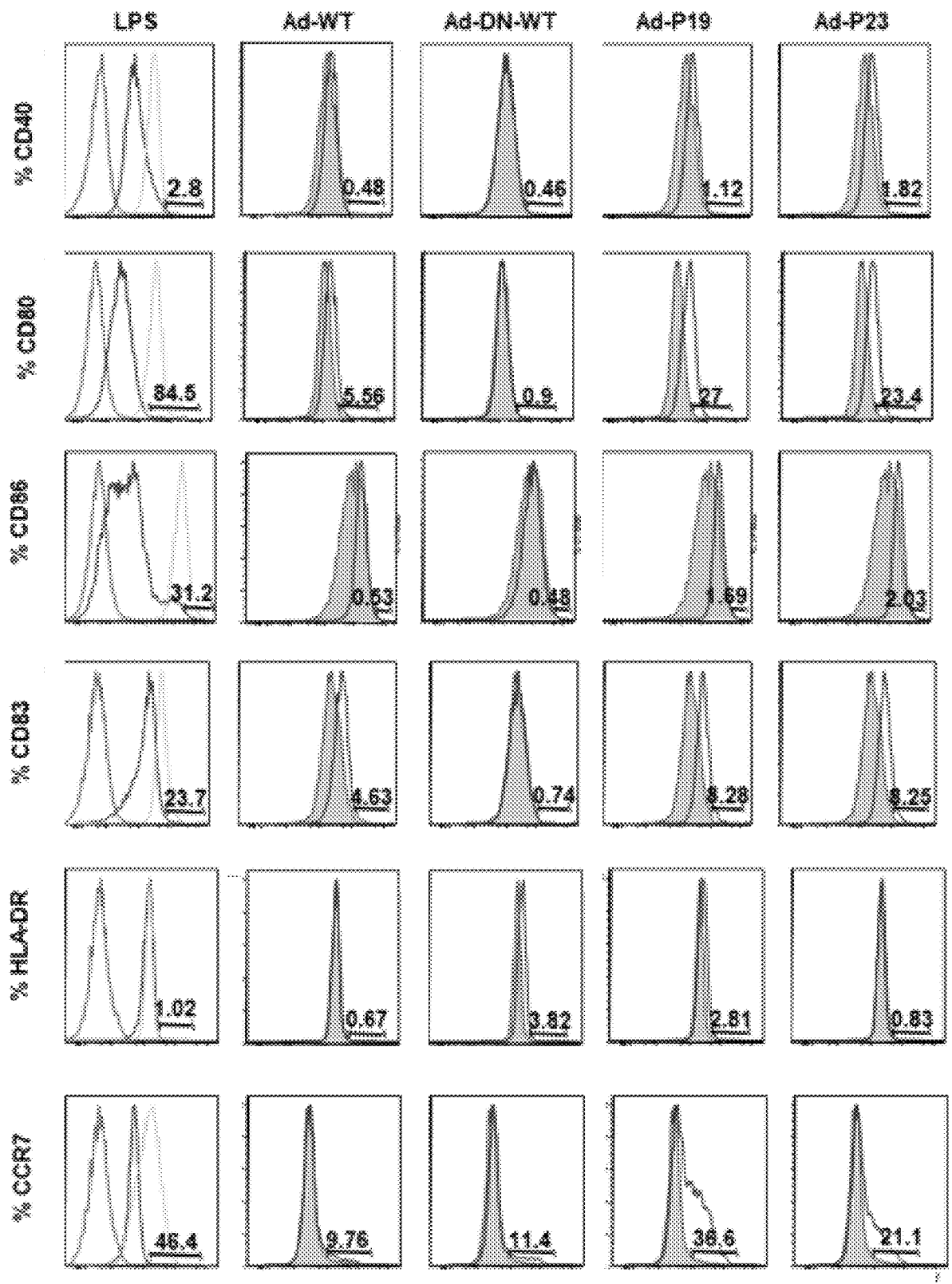
Figure 3B:
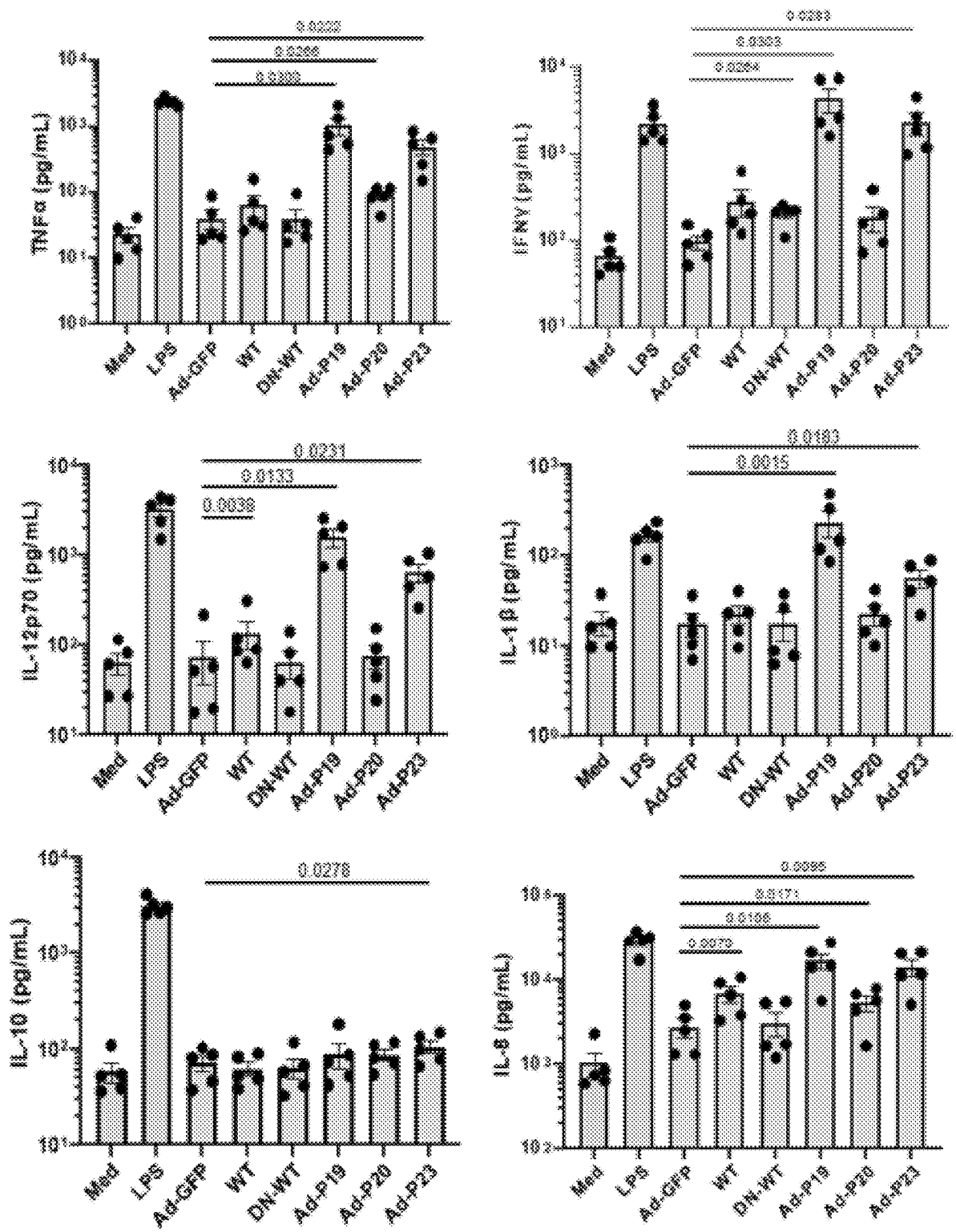

FIGS. 3A and 3B show phenotypic characterization of DC differentiation and cytokine profile after transduction with DAP12 mutants. FIG. 3A shows flow cytometric analysis of five-day Mo-DCs were treated with Ad-GFP, Ad-WT, Ad-DN-WT, Ad-P19, Ad-P23, or LPS (2 µg/mL) for 48 h for changes in CD40, CD80, CD86, CD83, HLA-DR and CCR7. Each experimental construct was compared to the empty-vector control, filled histograms, and infected cells were gated on GFP prior to analysis. In LPS histograms, red denotes unstained cells, blue isotype and green is stain as labeled. In subsequent histograms filled histograms are isotype and open are marker of interest as labeled. FIG. 3B shows supernatants from experiment "a" were analyzed by TNF-α, IFN-γ, IL-8, IL-1β, IL-12p70, or IL-10 specific ELISA. Results are expressed as mean value±SEM of 5 independent experiments. Significance was assessed by comparing against Ad-GFP transfected cells via paired student t test (shown) or ANOVA in Table 4. Analyzed data is shown in light blue and medium (MED) and LPS serve as other negative and positive controls respectively (shown in grey).

Figure 4:
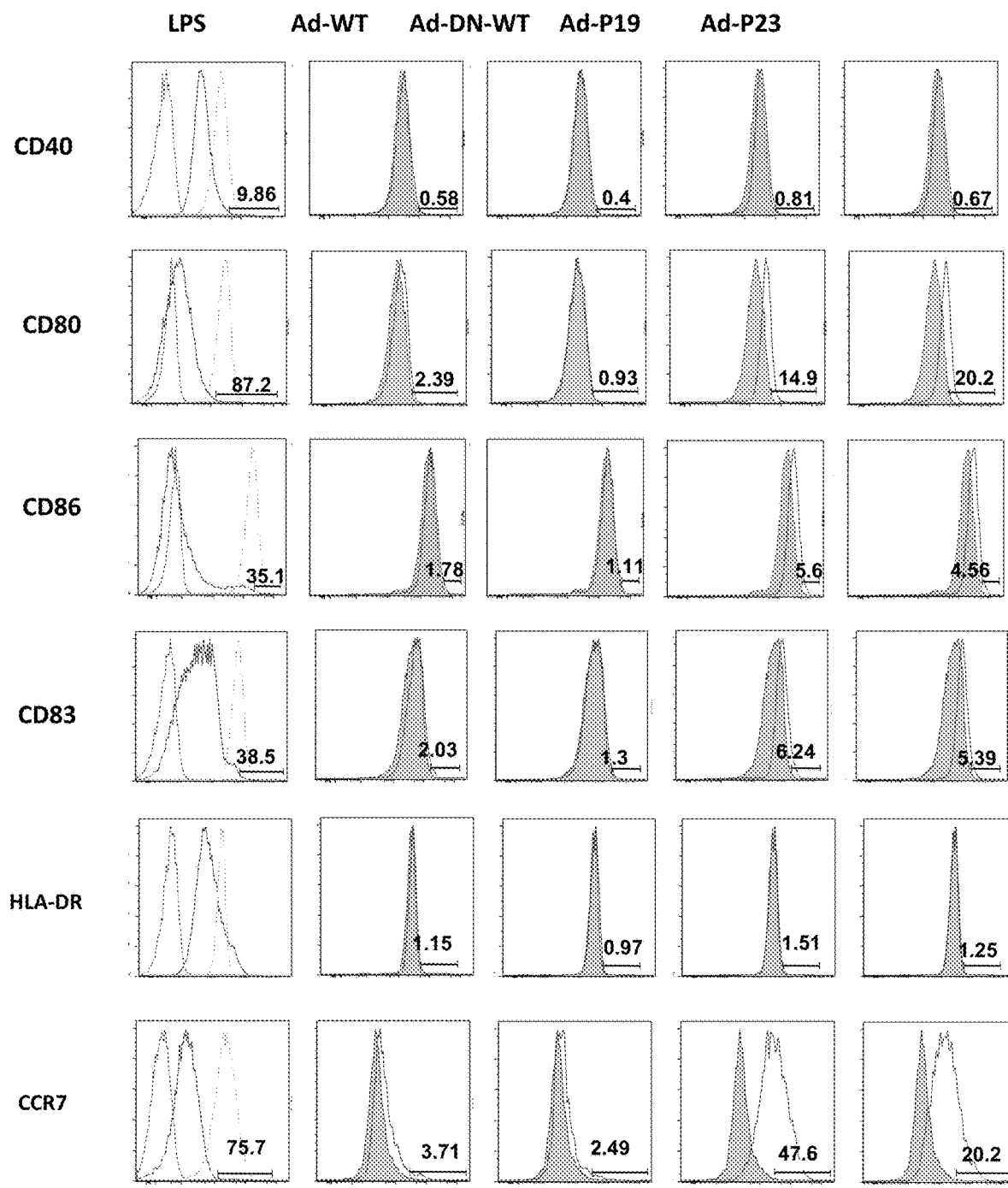

FIG. 4 shows flow cytometric analysis of Mo-DCs treated with Ad-GFP, Ad-WT, Ad-DN-WT, Ad-P19, Ad-P23, or LPS (2 µg/mL) for 24 h for changes in CD40, CD80, CD86, CD83, HLA-DR and CCR7. Each experimental construct was compared to the empty-vector control, filled histograms, and infected cells were gated on GFP prior to analysis FIGS. 5A, 5B, 5C, and 5D show that P19 and P23 enhance the migration and activation of Mo-DCs to CCL19 in vitro. (a) Migration assay of Mo-DC (5×104 cells in 50 µl, top chamber) stimulated with LPS alone (positive control) or in the presence of Ad-GFP, Ad-P19, Ad-P23, Ad-DAP12 or Ad-DN-DAP12 in a micro-chemotaxis chamber. The bottom chambers were filled with serum-free medium with or without CCL19 (100 ng/mL). DC migration rates were determined by counting Diff-Quick stained cells trapped in the filter. The figure represents the fold difference were the experimental control is Med (1) and the background controls is CCL19 untreated cells. (b) Mo-DCs as in "a" were pulsed with K562 lysates, treated with mitomycin c and co-cultured with PBMC (2.0×105 cells/well). After stimulation, 51Cr-labeled target K562 tumor cells were used in a cytotoxicity (51Cr-release) assay at an effector:target ratio of 20 to 1. (c) The specific proliferation of CD8+ T cells in experiment in "b" by BrdU incorporation via flow cytometry. (d) Proliferation of total CD3+ T cells was measured by Brdu incorporation (representative figure of n=3). Student t-test analysis is shown and ANOVA analysis p values are in Table 4.

Figure 6A:
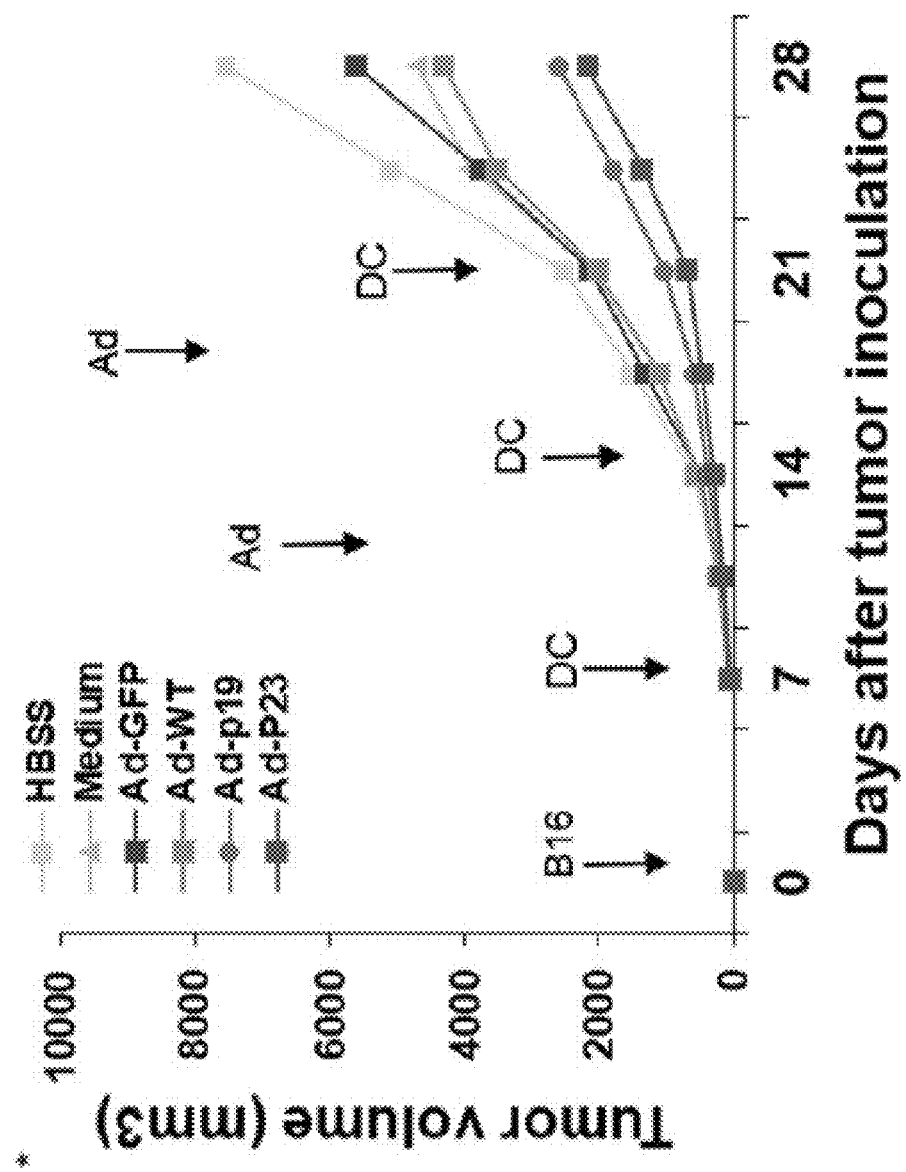
Figure 6B:
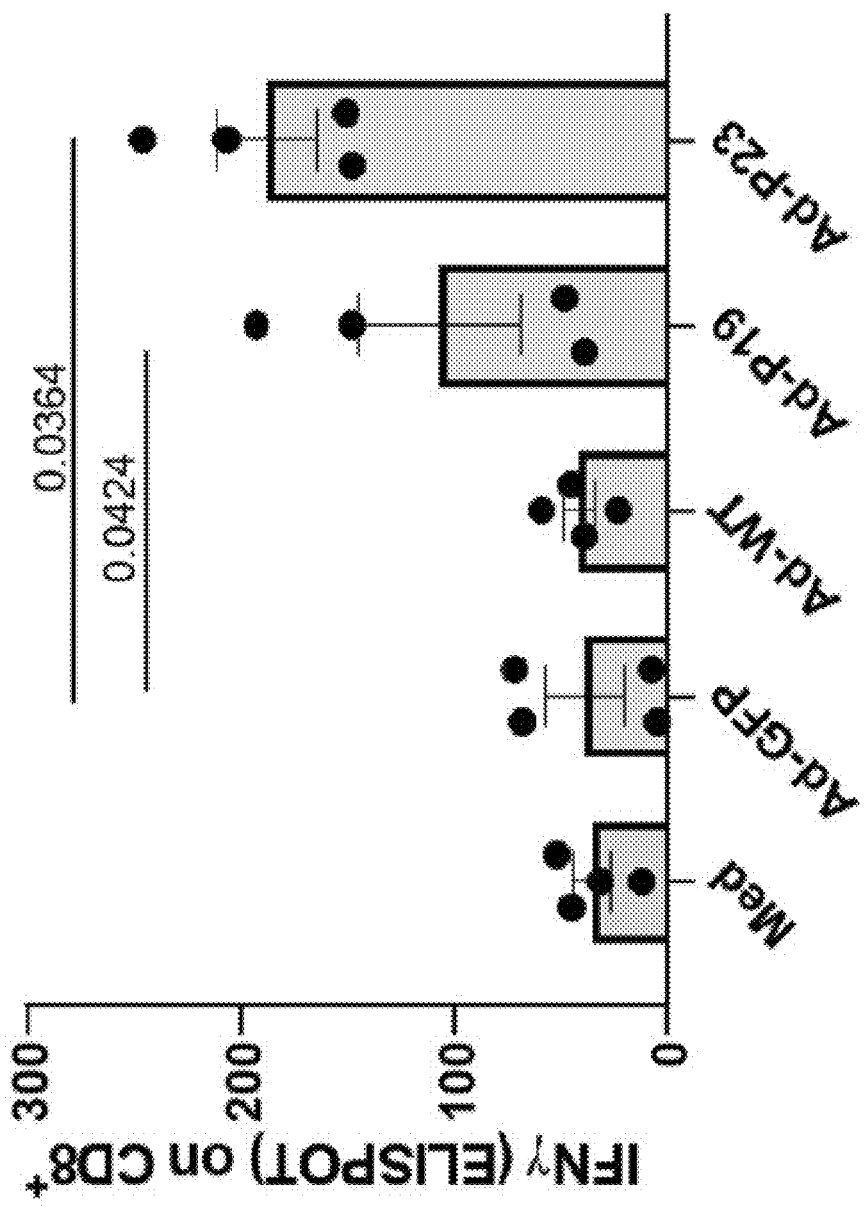
Figure 6C:
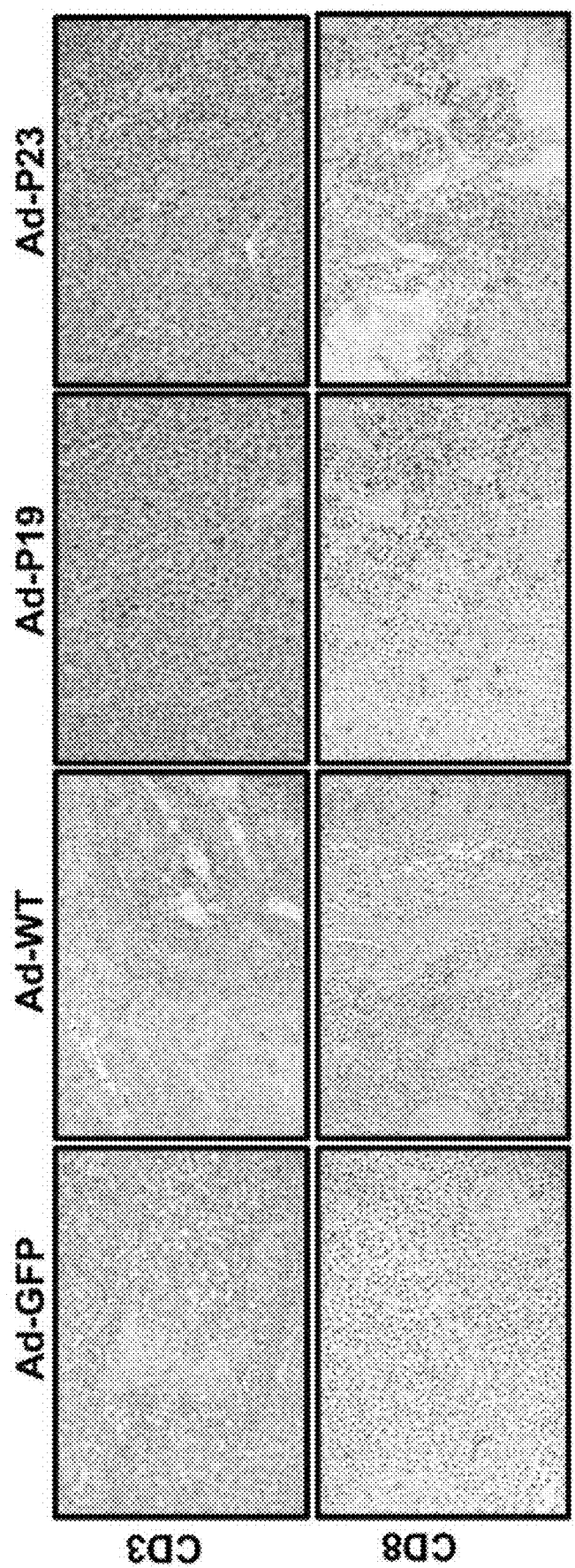

FIGS. 6A, 6B, and 6C show suppression of tumor growth induced by intratumoral administration of Ad-P23-modified DCs. FIG. 6A shows that tumor volume increases (mm3, measured twice per week) in murine melanoma model of B16 cells (2.5×105) implanted subcutaneously in syngeneic C57BL/6 mice (n=7/group) that received intratumoral transduced bone marrow DC (Medium-MED, untreated-, Ad-GFP, Ad-WT, Ad-P19 and Ad-P23, 5×106 cells per injection) on day 8 and weekly thereafter. Paired student t test was analyzed against all controls (HBSS, Medium, Ad-GFP, blue lines) and WT DAP12 (Ad-WT, green line). Ad-P19 and AdP23 (red lines) were significant against all after the 14-day time point (p<0.05). FIG. 6B shows EliSpot detection of IFNγ secretion from CD8+ T cells isolated from splenocytes of B16 murine melanoma model as in "a" sacrificed on day 28. The number of spots per 3×105 CD8+ T cells is shown and p values were calculated using paired Student's t test. FIG. 6C shows immunohistochemical staining revealed that the number of tumor-infiltrating CD3+ T cells (top panels) and CD8+ T cells (bottom panels) in the group of mice treated with Ad-P19/DC or Ad-P23/DC was significantly greater than that in the group of mice treated with Ad-GFP/DC, Ad-WT/DC or DC alone. Panels are representative of samples from 7 mice per group with similar staining profiles and images are displayed at ×200 magnification. Calculated p values of student t-test are in Table 5 and ANOVA in FIG. 7b by calculating the AUC.

Figure 7A:
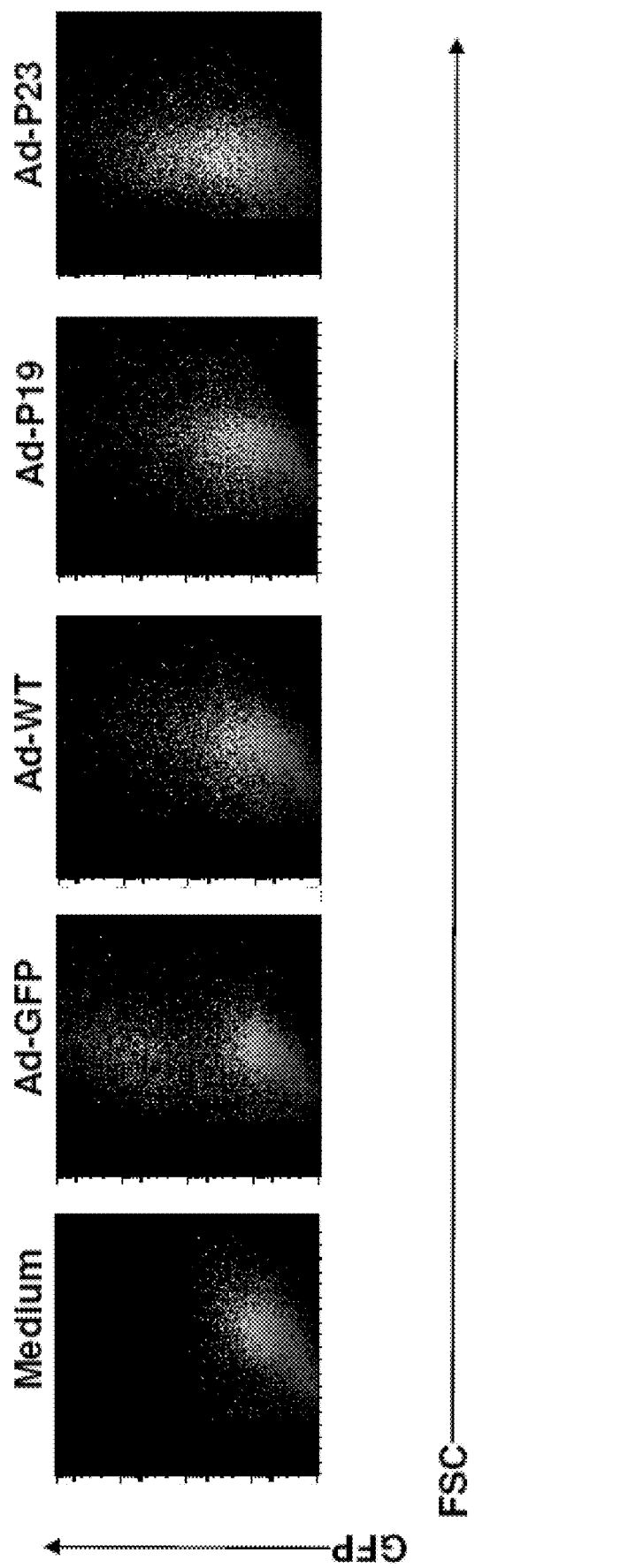

FIG. 7A shows GFP expression flow cytometric analysis of bone marrow DCs from animal experiment in FIG. 4 transfected with Nothing (medium), Ad-GFP, Ad-WT, Ad-P19, and Ad-P23 (representative figure).

Figure 7B:
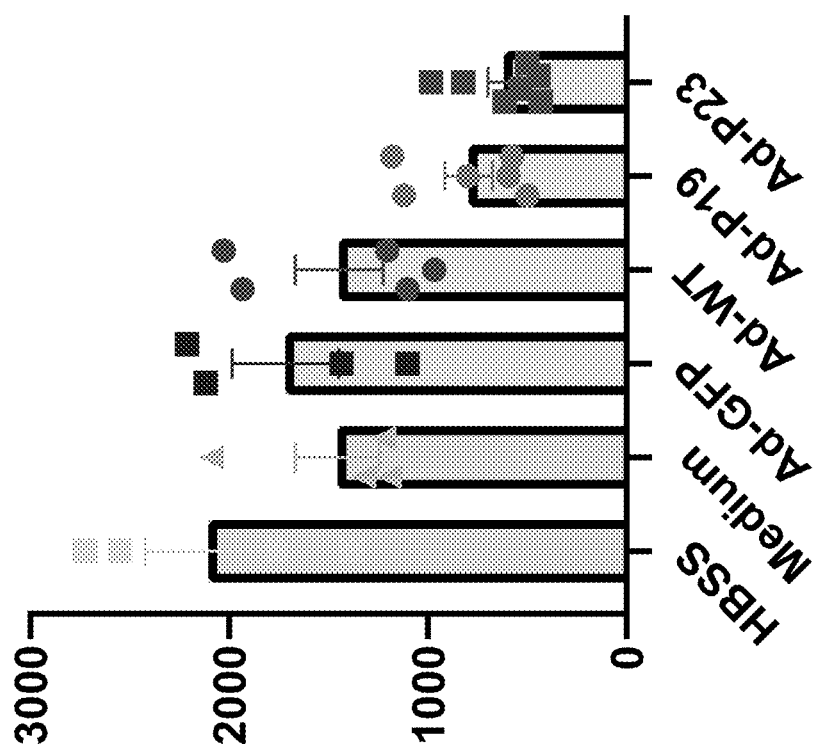

FIG. 7B shows a representation of calculation of area under the curve (AUC) for animals as in "a". The significance was measured with ANOVA (shown) against Ad-GFP as control). The AUC was performed with animals that survived to the end of the study.

IV. DETAILED DESCRIPTION

Before the present compounds, compositions, articles, devices, and/or methods are disclosed and described, it is to be understood that they are not limited to specific synthetic methods or specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

A. Definitions

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to and 15 are considered disclosed as well as between 10 and 15. It is also understood that each unit between two particular units are also disclosed. For example, if 10 and 15 are disclosed, then 11, 12, 13, and 14 are also disclosed.

In this specification and in the claims which follow, reference will be made to a number of terms which shall be defined to have the following meanings:

"Optional" or "optionally" means that the subsequently described event or circumstance may or may not occur, and that the description includes instances where said event or circumstance occurs and instances where it does not.

An "increase" can refer to any change that results in a greater amount of a symptom, disease, composition, condition or activity. An increase can be any individual, median, or average increase in a condition, symptom, activity, composition in a statistically significant amount. Thus, the increase can be a 1, 2, 3, 4, 5, 6, 7, 8, 9, 10, 15, 20, 25, 30, 35, 40, 45, 50, 55, 60, 65, 70, 75, 80, 85, 90, 95, or 100% increase so long as the increase is statistically significant.

A "decrease" can refer to any change that results in a smaller amount of a symptom, disease, composition, condition, or activity. A substance is also understood to decrease the genetic output of a gene when the genetic output of the gene product with the substance is less relative to the output of the gene product without the substance. Also for example, a decrease can be a change in the symptoms of a disorder such that the symptoms are less than previously observed. A decrease can be any individual, median, or average decrease in a condition, symptom, activity, composition in a statistically significant amount. Thus, the decrease can be a 1, 2, 3, 4, 5, 6, 7, 8, 9, 10, 15, 20, 25, 30, 35, 40, 45, 50, 55, 60, 65, 70, 75, 80, 85, 90, 95, or 100% decrease so long as the decrease is statistically significant.

"Inhibit," "inhibiting," and "inhibition" mean to decrease an activity, response, condition, disease, or other biological parameter. This can include but is not limited to the complete ablation of the activity, response, condition, or disease. This may also include, for example, a 10% reduction in the activity, response, condition, or disease as compared to the native or control level. Thus, the reduction can be a 10, 20, 30, 40, 50, 60, 70, 80, 90, 100%, or any amount of reduction in between as compared to native or control levels.

By "reduce" or other forms of the word, such as "reducing" or "reduction," is meant lowering of an event or characteristic (e.g., tumor growth). It is understood that this is typically in relation to some standard or expected value, in other words it is relative, but that it is not always necessary for the standard or relative value to be referred to. For example, "reduces tumor growth" means reducing the rate of growth of a tumor relative to a standard or a control.

By "prevent" or other forms of the word, such as "preventing" or "prevention," is meant to stop a particular event or characteristic, to stabilize or delay the development or progression of a particular event or characteristic, or to minimize the chances that a particular event or characteristic will occur. Prevent does not require comparison to a control as it is typically more absolute than, for example, reduce. As used herein, something could be reduced but not prevented, but something that is reduced could also be prevented. Likewise, something could be prevented but not reduced, but something that is prevented could also be reduced. It is understood that where reduce or prevent are used, unless specifically indicated otherwise, the use of the other word is also expressly disclosed.

The term "subject" refers to any individual who is the target of administration or treatment. The subject can be a vertebrate, for example, a mammal. In one aspect, the subject can be human, non-human primate, bovine, equine, porcine, canine, or feline. The subject can also be a guinea pig, rat, hamster, rabbit, mouse, or mole. Thus, the subject can be a human or veterinary patient. The term "patient" refers to a subject under the treatment of a clinician, e.g., physician.

The term "therapeutically effective" refers to the amount of the composition used is of sufficient quantity to ameliorate one or more causes or symptoms of a disease or disorder. Such amelioration only requires a reduction or alteration, not necessarily elimination.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

"Biocompatible" generally refers to a material and any metabolites or degradation products thereof that are generally non-toxic to the recipient and do not cause significant adverse effects to the subject.

"Comprising" is intended to mean that the compositions, methods, etc. include the recited elements, but do not exclude others. "Consisting essentially of" when used to define compositions and methods, shall mean including the recited elements, but excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions provided and/or claimed in this disclosure. Embodiments defined by each of these transition terms are within the scope of this disclosure.

A "control" is an alternative subject or sample used in an experiment for comparison purposes. A control can be "positive" or "negative."

"Effective amount" of an agent refers to a sufficient amount of an agent to provide a desired effect. The amount of agent that is "effective" will vary from subject to subject, depending on many factors such as the age and general condition of the subject, the particular agent or agents, and the like. Thus, it is not always possible to specify a quantified "effective amount." However, an appropriate "effective amount" in any subject case may be determined by one of ordinary skill in the art using routine experimentation. Also, as used herein, and unless specifically stated otherwise, an "effective amount" of an agent can also refer to an amount covering both therapeutically effective amounts and prophylactically effective amounts. An "effective amount" of an agent necessary to achieve a therapeutic effect may vary according to factors such as the age, sex, and weight of the subject. Dosage regimens can be adjusted to provide the optimum therapeutic response. For example, several divided doses may be administered daily or the dose may be proportionally reduced as indicated by the exigencies of the therapeutic situation.

A "pharmaceutically acceptable" component can refer to a component that is not biologically or otherwise undesirable, i.e., the component may be incorporated into a pharmaceutical formulation provided by the disclosure and administered to a subject as described herein without causing significant undesirable biological effects or interacting in a deleterious manner with any of the other components of the formulation in which it is contained. When used in reference to administration to a human, the term generally implies the component has met the required standards of toxicological and manufacturing testing or that it is included on the Inactive Ingredient Guide prepared by the U.S. Food and Drug Administration.

"Pharmaceutically acceptable carrier" (sometimes referred to as a "carrier") means a carrier or excipient that is useful in preparing a pharmaceutical or therapeutic composition that is generally safe and non-toxic and includes a carrier that is acceptable for veterinary and/or human pharmaceutical or therapeutic use. The terms "carrier" or "pharmaceutically acceptable carrier" can include, but are not limited to, phosphate buffered saline solution, water, emulsions (such as an oil/water or water/oil emulsion) and/or various types of wetting agents. As used herein, the term "carrier" encompasses, but is not limited to, any excipient, diluent, filler, salt, buffer, stabilizer, solubilizer, lipid, stabilizer, or other material well known in the art for use in pharmaceutical formulations and as described further herein.

"Pharmacologically active" (or simply "active"), as in a "pharmacologically active" derivative or analog, can refer to a derivative or analog (e.g., a salt, ester, amide, conjugate, metabolite, isomer, fragment, etc.) having the same type of pharmacological activity as the parent compound and approximately equivalent in degree.

"Therapeutic agent" refers to any composition that has a beneficial biological effect. Beneficial biological effects include both therapeutic effects, e.g., treatment of a disorder or other undesirable physiological condition, and prophylactic effects, e.g., prevention of a disorder or other undesirable physiological condition (e.g., a non-immunogenic cancer). The terms also encompass pharmaceutically acceptable, pharmacologically active derivatives of beneficial agents specifically mentioned herein, including, but not limited to, salts, esters, amides, proagents, active metabolites, isomers, fragments, analogs, and the like. When the terms "therapeutic agent" is used, then, or when a particular agent is specifically identified, it is to be understood that the term includes the agent per se as well as pharmaceutically acceptable, pharmacologically active salts, esters, amides, proagents, conjugates, active metabolites, isomers, fragments, analogs, etc.

"Therapeutically effective amount" or "therapeutically effective dose" of a composition (e.g. a composition comprising an agent) refers to an amount that is effective to achieve a desired therapeutic result. In some embodiments, a desired therapeutic result is the control of type I diabetes. In some embodiments, a desired therapeutic result is the control of obesity. Therapeutically effective amounts of a given therapeutic agent will typically vary with respect to factors such as the type and severity of the disorder or disease being treated and the age, gender, and weight of the subject. The term can also refer to an amount of a therapeutic agent, or a rate of delivery of a therapeutic agent (e.g., amount over time), effective to facilitate a desired therapeutic effect, such as pain relief. The precise desired therapeutic effect will vary according to the condition to be treated, the tolerance of the subject, the agent and/or agent formulation to be administered (e.g., the potency of the therapeutic agent, the concentration of agent in the formulation, and the like), and a variety of other factors that are appreciated by those of ordinary skill in the art. In some instances, a desired biological or medical response is achieved following administration of multiple dosages of the composition to the subject over a period of days, weeks, or years.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

B. Compositions

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular modified DAP12 is disclosed and discussed and a number of modifications that can be made to a number of molecules including the modified DAP12 are discussed, specifically contemplated is each and every combination and permutation of modified DAP12 and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

Many stimulatory receptors (such as TREM, Siglec-H, and SIRP-β) associate with Immune-receptor tyrosine-based activation motif (ITAM)-containing adapter molecules through their negatively charged residues in the transmembrane domain to transduce their pro-inflammatory signals to the nucleus. One such ITAM-containing adaptor molecule is DAP12 (12-kilodalton DNAX activating protein, also known as TYROBP and KARAP) which is expressed by Natural Killer (NK) cells and myeloid cells, including granulocytes, monocytes, macrophages and DCs. DAP12 mediates signaling for numerous activating cell-surface receptors expressed by these cells. This relatively small 113 amino acid protein maintains a membrane domain and a cytoplasmic tail, containing the canonical ITAM motif $YxxL/Ix_{6-8}YxxL/I$ (where x represents any amino acid), and where the tyrosine residues within the ITAM domain are both necessary and sufficient for the induction of intracellular signals. Signaling occurs from ligand induced clustering followed by phosphorylation, often by Src family kinases, of the tyrosine residues of the ITAM motifs. Phosphorylated ITAMs create SH2 docking sites, initiating ZAP-70 and Syk kinase signaling to multiple downstream mediators ultimately leading to cellular activation. Functionally, this signaling cascade culminates in antigen directed anti-tumor cytotoxic responses and the regulation of innate and inflammatory cytokine production. Studies have demonstrated that crosslinking of DAP12-associated complexes can lead to myeloid cell activation as determined by enhanced $Ca^{2+}$ influx, MAP kinase activation, and secretion of cytokines and chemokines. Importantly, DAP12 mediated TREM2 signaling is now known to be critical for priming myeloid cell migration, survival, and co-stimulation of the resulting immune response. Furthermore, DAP12 has recently been linked to the cross-presentation pathway necessary for the uptake and presentation of antigens derived from apoptotic, necrotic, and conceivably neoplastic cells.

Given the crucial role of DAP12 in the inflammatory function of DCs, we hypothesized that we could take advantage of DAP12's initial signal through the use of a constitutively active form of DAP12 to promote antigen uptake, maturation, migration, and T cell stimulation leading to a more effective anti-tumor immune response. This strategy is meant to avoid accumulation of inactive immature monocyte-derived DCs (Mo-DCs), which could contribute to immune suppression, while inducing phenotypically functional DCs that can migrate to the tumor and induce an active immune response. This approach has been shown by us to be effective in activating accumulated suppressive immature myeloid populations in primary myelodysplastic syndrome (MDS) patient samples. Herein we fully characterize constitutively active DAP12 mutant constructs and the molecular signaling pathways demonstrating their function in primary Mo-DCs. This work confirms the important role of DAP12-induced maturation, migration, antigen uptake, and T cell stimulation on anti-tumor myeloid cells. Furthermore, we demonstrate here the beneficial anti-tumor immune responses in an in vivo murine tumor model treated with constitutively active DAP12 expressing Mo-DCs. This study provides a novel approach to induce stronger anti-tumor DCs ex vivo for their subsequent use as tumor immunotherapies.

In one aspect, disclosed herein are modified 12-kilodalton DNAX activating protein (DAP12) comprising one or more substitutions in the cytoplasmic domain of DAP12 (such as, for example a substitution at a residue corresponding to residues 91, 99, 100, 101, 102, 104, 105, 106, 111, or 112 of DAP12 as represented by SEQ ID NO: 1, including, but not limited to a D100V substitution; a Y91E substitution; a S99H substitution; a D100H substitution; a Y102C substitution; a Y102E substitution; a Y102D substitution; a V101R substitution; a D104H substitution; a Y111E substitution; a Y111D substitution; a Y112D substitution; a Y112E substitution; a Y91D substitution; a D104N substitution; a Y91C substitution; a L105Y substitution; and/or a N106K substitution and/or any combination thereof, including, but not limited to a Y91E, Y102E, and Y112E substitution; a Y91E, Y102E, Y111E, and Y112E substitution; a Y91D and Y102D substitution; a D100V and V101R substitution; or a S99H and a D104H substitution).

Also disclosed herein are modified DAP12, wherein the one or more substitutions occur in the ITAM sequence (such as, for example, one or more substitutions occurs at a residue corresponding to residues 91, 99, 100, 101, 102, 104, and/or 105 of DAP12). In one aspect, disclosed herein are modified DAP12, wherein the one or more substitutions mimic phosphorylation, including, but not limited to modified DAP12 wherein the one or more substitutions comprise a Y91E, Y91D, Y102D, Y102E, Y111D, Y111E, Y112D, and/or Y112E substitution.

Also disclosed herein are modified DAP12, wherein the one or more substitutions block activation, including, but not limited modified DAP12 wherein the one or more substitutions comprise a Y91C and/or Y102C substitution.

In one aspect, disclosed herein are modified DAP12, wherein the one or more substitutions allow normal binding with rapid dissociation, including, but not limited modified DAP12 wherein the one or more substitutions comprise a D100V or D100H substitution.

Also disclosed herein are modified DAP12, wherein the one or more substitutions disrupt the ITAM interaction, including, but not limited modified DAP12 wherein the one or more substitutions comprise a V101R substitution.

1. Homology/Identity (Version 1)

It is understood that one way to define any known variants and derivatives or those that might arise, of the disclosed genes and proteins herein is through defining the variants and derivatives in terms of homology to specific known sequences. Specifically disclosed are variants of these and other genes and proteins herein disclosed which have at least, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 percent homology to the stated sequence. Those of skill in the art readily understand how to determine the homology of two proteins or nucleic acids, such as genes. For example, the homology can be calculated after aligning the two sequences so that the homology is at its highest level.

Another way of calculating homology can be performed by published algorithms. Optimal alignment of sequences for comparison may be conducted by the local homology algorithm of Smith and Waterman Adv. Appl. Math. 2: 482 (1981), by the homology alignment algorithm of Needleman and Wunsch, J. MoL Biol. 48: 443 (1970), by the search for similarity method of Pearson and Lipman, Proc. Natl. Acad. Sci. U.S.A. 85: 2444 (1988), by computerized implementations of these algorithms (GAP, BESTFIT, FASTA, and TFASTA in the Wisconsin Genetics Software Package, Genetics Computer Group, 575 Science Dr., Madison, WI), or by inspection.

The same types of homology can be obtained for nucleic acids by for example the algorithms disclosed in Zuker, M. Science 244:48-52, 1989, Jaeger et al. Proc. Natl. Acad. Sci. USA 86:7706-7710, 1989, Jaeger et al. Methods Enzymol. 183:281-306, 1989 which are herein incorporated by reference for at least material related to nucleic acid alignment.

2. Peptides a) Protein Variants

As discussed herein there are numerous variants of the DAP12 protein that are known and herein contemplated. Protein variants and derivatives are well understood to those of skill in the art and in can involve amino acid sequence modifications. For example, amino acid sequence modifications typically fall into one or more of three classes: substitutional, insertional or deletional variants. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Immunogenic fusion protein derivatives, such as those described in the examples, are made by fusing a polypeptide sufficiently large to confer immunogenicity to the target sequence by cross-linking in vitro or by recombinant cell culture transformed with DNA encoding the fusion. Deletions are characterized by the removal of one or more amino acid residues from the protein sequence. Typically, no more than about from 2 to 6 residues are deleted at any one site within the protein molecule. These variants ordinarily are prepared by site specific mutagenesis of nucleotides in the DNA encoding the protein, thereby producing DNA encoding the variant, and thereafter expressing the DNA in recombinant cell culture. Techniques for making substitution mutations at predetermined sites in DNA having a known sequence are well known, for example M13 primer mutagenesis and PCR mutagenesis. Amino acid substitutions are typically of single residues, but can occur at a number of different locations at once; insertions usually will be on the order of about from 1 to 10 amino acid residues; and deletions will range about from 1 to 30 residues. Deletions or insertions preferably are made in adjacent pairs, i.e. a deletion of 2 residues or insertion of 2 residues. Substitutions, deletions, insertions or any combination thereof may be combined to arrive at a final construct. The mutations must not place the sequence out of reading frame and preferably will not create complementary regions that could produce secondary mRNA structure. Substitutional variants are those in which at least one residue has been removed and a different residue inserted in its place. Such substitutions generally are made in accordance with the following Tables 1 and 2 and are referred to as conservative substitutions.

TABLE 1

| Amino Acid Abbreviations | | |
|---|---|---|
| Amino Acid | Abbreviations | |
| Alanine | Ala | A |
| allosoleucine | AIle | |
| Arginine | Arg | R |
| asparagine | Asn | N |
| aspartic acid | Asp | D |
| Cysteine | Cys | C |

TABLE 1-continued

Amino Acid Abbreviations

| Amino Acid | Abbreviations | |
|---|---|---|
| glutamic acid | Glu | E |
| Glutamine | Gln | Q |
| Glycine | Gly | G |
| Histidine | His | H |
| Isolelucine | Ile | I |
| Leucine | Leu | L |
| Lysine | Lys | K |
| phenylalanine | Phe | F |
| proline | Pro | P |
| pyroglutamic acid | pGlu | |
| Serine | Ser | S |
| Threonine | Thr | T |
| Tyrosine | Tyr | Y |
| Tryptophan | Trp | W |
| Valine | Val | V |

TABLE 2

Amino Acid Substitutions
Original Residue Exemplary Conservative
Substitutions, others are known in the art.

| Ala | Ser |
|---|---|
| Arg | Lys; Gln |
| Asn | Gln; His |
| Asp | Glu |
| Cys | Ser |
| Gln | Asn, Lys |
| Glu | Asp |
| Gly | Pro |
| His | Asn; Gln |
| Ile | Leu; Val |
| Leu | Ile; Val |
| Lys | Arg; Gln |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Substantial changes in function or immunological identity are made by selecting substitutions that are less conservative than those in Table 2, i.e., selecting residues that differ more significantly in their effect on maintaining (a) the structure of the polypeptide backbone in the area of the substitution, for example as a sheet or helical conformation, (b) the charge or hydrophobicity of the molecule at the target site or (c) the bulk of the side chain. The substitutions which in general are expected to produce the greatest changes in the protein properties will be those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine, in this case, (e) by increasing the number of sites for sulfation and/or glycosylation.

For example, the replacement of one amino acid residue with another that is biologically and/or chemically similar is known to those skilled in the art as a conservative substitution. For example, a conservative substitution would be replacing one hydrophobic residue for another, or one polar residue for another. The substitutions include combinations such as, for example, Gly, Ala; Val, Ile, Leu; Asp, Glu; Asn, Gln; Ser, Thr; Lys, Arg; and Phe, Tyr. Such conservatively substituted variations of each explicitly disclosed sequence are included within the mosaic polypeptides provided herein.

Substitutional or deletional mutagenesis can be employed to insert sites for N-glycosylation (Asn-X-Thr/Ser) or O-glycosylation (Ser or Thr). Deletions of cysteine or other labile residues also may be desirable. Deletions or substitutions of potential proteolysis sites, e.g. Arg, is accomplished for example by deleting one of the basic residues or substituting one by glutaminyl or histidyl residues.

Certain post-translational derivatizations are the result of the action of recombinant host cells on the expressed polypeptide. Glutaminyl and asparaginyl residues are frequently post-translationally deamidated to the corresponding glutamyl and asparyl residues. Alternatively, these residues are deamidated under mildly acidic conditions. Other post-translational modifications include hydroxylation of proline and lysine, phosphorylation of hydroxyl groups of seryl or threonyl residues, methylation of the o-amino groups of lysine, arginine, and histidine side chains (T. E. Creighton, Proteins: Structure and Molecular Properties, W. H. Freeman & Co., San Francisco pp 79-86 [1983]), acetylation of the N-terminal amine and, in some instances, amidation of the C-terminal carboxyl.

It is understood that one way to define the variants and derivatives of the disclosed proteins herein is through defining the variants and derivatives in terms of homology/identity to specific known sequences. Specifically disclosed are variants of these and other proteins herein disclosed which have at least, 70% or 75% or 80% or 85% or 90% or 95% homology to the stated sequence. Those of skill in the art readily understand how to determine the homology of two proteins. For example, the homology can be calculated after aligning the two sequences so that the homology is at its highest level.

Another way of calculating homology can be performed by published algorithms. Optimal alignment of sequences for comparison may be conducted by the local homology algorithm of Smith and Waterman *Adv. Appl. Math.* 2: 482 (1981), by the homology alignment algorithm of Needleman and Wunsch, *J. MoL Biol.* 48: 443 (1970), by the search for similarity method of Pearson and Lipman, *Proc. Natl. Acad. Sci. U.S.A.* 85: 2444 (1988), by computerized implementations of these algorithms (GAP, BESTFIT, FASTA, and TFASTA in the Wisconsin Genetics Software Package, Genetics Computer Group, 575 Science Dr., Madison, WI), or by inspection.

The same types of homology can be obtained for nucleic acids by for example the algorithms disclosed in Zuker, M. Science 244:48-52, 1989, Jaeger et al. *Proc. Natl. Acad. Sci. USA* 86:7706-7710, 1989, Jaeger et al. *Methods Enzymol.* 183:281-306, 1989.

It is understood that the description of conservative mutations and homology can be combined together in any combination, such as embodiments that have at least 70% homology to a particular sequence wherein the variants are conservative mutations.

As this specification discusses various proteins and protein sequences it is understood that the nucleic acids that can encode those protein sequences are also disclosed. This would include all degenerate sequences related to a specific protein sequence, i.e. all nucleic acids having a sequence that encodes one particular protein sequence as well as all nucleic acids, including degenerate nucleic acids, encoding the disclosed variants and derivatives of the protein sequences. Thus, while each particular nucleic acid sequence may not be written out herein, it is understood that each and every sequence is in fact disclosed and described herein through the disclosed protein sequence.

It is understood that there are numerous amino acid and peptide analogs which can be incorporated into the disclosed compositions. For example, there are numerous D amino acids or amino acids which have a different functional substituent then the amino acids shown in Table 1 and Table 2. The opposite stereo isomers of naturally occurring peptides are disclosed, as well as the stereo isomers of peptide analogs. These amino acids can readily be incorporated into polypeptide chains by charging tRNA molecules with the amino acid of choice and engineering genetic constructs that utilize, for example, amber codons, to insert the analog amino acid into a peptide chain in a site specific way.

Molecules can be produced that resemble peptides, but which are not connected via a natural peptide linkage. For example, linkages for amino acids or amino acid analogs can include $CH_2NH$—, —$CH_2S$—, —$CH_2$—$CH_2$—, —CH=CH— (cis and trans), —$COCH_2$—, —CH(OH) $CH_2$—, and —$CHH_2SO$— (These and others can be found in Spatola, A. F. in *Chemistry and Biochemistry of Amino Acids, Peptides, and Proteins*, B. Weinstein, eds., Marcel Dekker, New York, p. 267 (1983); Spatola, A. F., *Vega Data* (March 1983), Vol. 1, Issue 3, Peptide Backbone Modifications (general review); Morley, Trends Pharm Sci (1980) pp. 463-468; Hudson, D. et al., Int J Pept Prot Res 14:177-185 (1979) (—$CH_2NH$—, $CH_2CH_2$—); Spatola et al. *Life Sci* 38:1243-1249 (1986) (—CH $H_2$—S); Hann *J. Chem. Soc Perkin Trans*. I 307-314 (1982) (—CH—CH—, cis and trans); Almquist et al. J. Med. Chem. 23:1392-1398 (1980) (—$COCH_2$—); Jennings-White et al. Tetrahedron Lett 23:2533 (1982) (—$COCH_2$—); Szelke et al. European Appln, EP 45665 CA (1982): 97:39405 (1982) (—CH(OH) $CH_2$—); Holladay et al. *Tetrahedron*. Lett 24:4401-4404 (1983) (—$C(OH)CH_2$—); and Hruby *Life Sci* 31:189-199 (1982) (—$CH_2$—S—); each of which is incorporated herein by reference. A particularly preferred non-peptide linkage is —$CH_2NH$—. It is understood that peptide analogs can have more than one atom between the bond atoms, such as b-alanine, g-aminobutyric acid, and the like.

Amino acid analogs and analogs and peptide analogs often have enhanced or desirable properties, such as, more economical production, greater chemical stability, enhanced pharmacological properties (half-life, absorption, potency, efficacy, etc.), altered specificity (e.g., a broad-spectrum of biological activities), reduced antigenicity, and others.

D-amino acids can be used to generate more stable peptides, because D amino acids are not recognized by peptidases and such. Systematic substitution of one or more amino acids of a consensus sequence with a D-amino acid of the same type (e.g., D-lysine in place of L-lysine) can be used to generate more stable peptides. Cysteine residues can be used to cyclize or attach two or more peptides together. This can be beneficial to constrain peptides into particular conformations.

3. Delivery of the Compositions to Cells

There are a number of compositions and methods which can be used to deliver nucleic acids to cells, either in vitro or in vivo. These methods and compositions can largely be broken down into two classes: viral based delivery systems and non-viral based delivery systems. For example, the nucleic acids can be delivered through a number of direct delivery systems such as, electroporation, lipofection, calcium phosphate precipitation, plasmids, viral vectors, viral nucleic acids, phage nucleic acids, phages, cosmids, or via transfer of genetic material in cells or carriers such as cationic liposomes. Appropriate means for transfection, including viral vectors, chemical transfectants, or physicomechanical methods such as electroporation and direct diffusion of DNA, are described by, for example, Wolff, J. A., et al., *Science,* 247, 1465-1468, (1990); and Wolff, J. A. *Nature,* 352, 815-818, (1991). Such methods are well known in the art and readily adaptable for use with the compositions and methods described herein. In certain cases, the methods will be modified to specifically function with large DNA molecules. Further, these methods can be used to target certain diseases and cell populations by using the targeting characteristics of the carrier. In one aspect, disclosed herein are vectors (such as, for example an adenoviral vector) comprising any of the modified DAP12 disclosed herein (such as, for example, a modified DAP12 comprising a D100V substitution; a Y91E substitution; a S99H substitution; a D100H substitution; a Y102C substitution; a Y102E substitution; a Y102D substitution; a V101R substitution; a D104H substitution; a Y111E substitution; a Y111D substitution; a Y112D substitution; a Y112E substitution; a Y91D substitution; a D104N substitution; a Y91C substitution; a L105Y substitution; and/or a N106K substitution and/or any combination thereof, including, but not limited to a Y91E, Y102E, and Y112E substitution; a Y91E, Y102E, Y111E, and Y112E substitution; a Y91D and Y102D substitution; a D100V and V101R substitution; or a S99H and a D104H substitution). In one aspect disclosed herein are dendritic cells comprising any of the modified DAP12 or vectors comprising said modified DAP12 disclosed herein (such as, for example, a modified DAP12 comprising a D100V substitution; a Y91E substitution; a S99H substitution; a D100H substitution; a Y102C substitution; a Y102E substitution; a Y102D substitution; a V101R substitution; a D104H substitution; a Y111E substitution; a Y111D substitution; a Y112D substitution; a Y112E substitution; a Y91D substitution; a D104N substitution; a Y91C substitution; a L105Y substitution; and/or a N106K substitution and/or any combination thereof, including, but not limited to a Y91E, Y102E, and Y112E substitution; a Y91E, Y102E, Y111E, and Y112E substitution; a Y91D and Y102D substitution; a D100V and V101R substitution; or a S99H and a D104H substitution).

a) Nucleic Acid Based Delivery Systems

Transfer vectors can be any nucleotide construction used to deliver genes into cells (e.g., a plasmid), or as part of a general strategy to deliver genes, e.g., as part of recombinant retrovirus or adenovirus (Ram et al. Cancer Res. 53:83-88, (1993)).

As used herein, plasmid or viral vectors are agents that transport the disclosed modified DAP12 (or nucleic acid encoding said modified DAP12) into the cell without degradation and include a promoter yielding expression of the gene in the cells into which it is delivered. Viral vectors are, for example, Adenovirus, Adeno-associated virus, Herpes virus, Vaccinia virus, Polio virus, AIDS virus, neuronal trophic virus, Sindbis and other RNA viruses, including these viruses with the HIV backbone. Also preferred are any viral families which share the properties of these viruses which make them suitable for use as vectors. Retroviruses include Murine Maloney Leukemia virus, MMLV, and retroviruses that express the desirable properties of MMLV as a vector. Retroviral vectors are able to carry a larger genetic payload, i.e., a transgene or marker gene, than other viral vectors, and for this reason are a commonly used vector. However, they are not as useful in non-proliferating cells.

Adenovirus vectors are relatively stable and easy to work with, have high titers, and can be delivered in aerosol formulation, and can transfect non-dividing cells. Pox viral vectors are large and have several sites for inserting genes, they are thermostable and can be stored at room temperature. A preferred embodiment is a viral vector which has been engineered so as to suppress the immune response of the host organism, elicited by the viral antigens. Preferred vectors of this type will carry coding regions for Interleukin 8 or 10.

Viral vectors can have higher transaction (ability to introduce genes) abilities than chemical or physical methods to introduce genes into cells. Typically, viral vectors contain, nonstructural early genes, structural late genes, an RNA polymerase III transcript, inverted terminal repeats necessary for replication and encapsidation, and promoters to control the transcription and replication of the viral genome. When engineered as vectors, viruses typically have one or more of the early genes removed and a gene or gene/promotor cassette is inserted into the viral genome in place of the removed viral DNA. Constructs of this type can carry up to about 8 kb of foreign genetic material. The necessary functions of the removed early genes are typically supplied by cell lines which have been engineered to express the gene products of the early genes in trans.

(1) Retroviral Vectors

A retrovirus is an animal virus belonging to the virus family of Retroviridae, including any types, subfamilies, genus, or tropisms. Retroviral vectors, in general, are described by Verma, I. M., Retroviral vectors for gene transfer.

A retrovirus is essentially a package which has packed into it nucleic acid cargo. The nucleic acid cargo carries with it a packaging signal, which ensures that the replicated daughter molecules will be efficiently packaged within the package coat. In addition to the package signal, there are a number of molecules which are needed in cis, for the replication, and packaging of the replicated virus. Typically a retroviral genome, contains the gag, pol, and env genes which are involved in the making of the protein coat. It is the gag, pol, and env genes which are typically replaced by the foreign DNA that it is to be transferred to the target cell. Retrovirus vectors typically contain a packaging signal for incorporation into the package coat, a sequence which signals the start of the gag transcription unit, elements necessary for reverse transcription, including a primer binding site to bind the tRNA primer of reverse transcription, terminal repeat sequences that guide the switch of RNA strands during DNA synthesis, a purine rich sequence 5' to the 3' LTR that serve as the priming site for the synthesis of the second strand of DNA synthesis, and specific sequences near the ends of the LTRs that enable the insertion of the DNA state of the retrovirus to insert into the host genome. The removal of the gag, pol, and env genes allows for about 8 kb of foreign sequence to be inserted into the viral genome, become reverse transcribed, and upon replication be packaged into a new retroviral particle. This amount of nucleic acid is sufficient for the delivery of a one to many genes depending on the size of each transcript. It is preferable to include either positive or negative selectable markers along with other genes in the insert.

Since the replication machinery and packaging proteins in most retroviral vectors have been removed (gag, pol, and env), the vectors are typically generated by placing them into a packaging cell line. A packaging cell line is a cell line which has been transfected or transformed with a retrovirus that contains the replication and packaging machinery, but lacks any packaging signal. When the vector carrying the DNA of choice is transfected into these cell lines, the vector containing the gene of interest is replicated and packaged into new retroviral particles, by the machinery provided in cis by the helper cell. The genomes for the machinery are not packaged because they lack the necessary signals.

(2) Adenoviral Vectors

The construction of replication-defective adenoviruses has been described (Berkner et al., *J. Virology* 61:1213-1220 (1987); Massie et al., *Mol. Cell. Biol.* 6:2872-2883 (1986); Haj-Ahmad et al., *J. Virology* 57:267-274 (1986); Davidson et al., *J. Virology* 61:1226-1239 (1987); Zhang "Generation and identification of recombinant adenovirus by liposome-mediated transfection and PCR analysis" *BioTechniques* 15:868-872 (1993)). The benefit of the use of these viruses as vectors is that they are limited in the extent to which they can spread to other cell types, since they can replicate within an initial infected cell, but are unable to form new infectious viral particles. Recombinant adenoviruses have been shown to achieve high efficiency gene transfer after direct, in vivo delivery to airway epithelium, hepatocytes, vascular endothelium, CNS parenchyma and a number of other tissue sites (Morsy, *J. Clin. Invest.* 92:1580-1586 (1993); Kirshenbaum, *J. Clin. Invest.* 92:381-387 (1993); Roessler, *J. Clin. Invest.* 92:1085-1092 (1993); Moullier, *Nature Genetics* 4:154-159 (1993); La Salle, *Science* 259:988-990 (1993); Gomez-Foix, *J. Biol. Chem.* 267:25129-25134 (1992); Rich, *Human Gene Therapy* 4:461-476 (1993); Zabner, *Nature Genetics* 6:75-83 (1994); Guzman, *Circulation Research* 73:1201-1207 (1993); Bout, *Human Gene Therapy* 5:3-10 (1994); Zabner, *Cell* 75:207-216 (1993); Caillaud, *Eur. J. Neuroscience* 5:1287-1291 (1993); and Ragot, *J. Gen. Virology* 74:501-507 (1993)). Recombinant adenoviruses achieve gene transduction by binding to specific cell surface receptors, after which the virus is internalized by receptor-mediated endocytosis, in the same manner as wild type or replication-defective adenovirus (Chardonnet and Dales, *Virology* 40:462-477 (1970); Brown and Burlingham, *J. Virology* 12:386-396 (1973); Svensson and Persson, *J. Virology* 55:442-449 (1985); Seth, et al., *J. Virol.* 51:650-655 (1984); Seth, et al., *Mol. Cell. Biol.* 4:1528-1533 (1984); Varga et al., *J. Virology* 65:6061-6070 (1991); Wickham et al., *Cell* 73:309-319 (1993)).

A viral vector can be one based on an adenovirus which has had the E1 gene removed and these virons are generated in a cell line such as the human 293 cell line. In another preferred embodiment both the E1 and E3 genes are removed from the adenovirus genome.

(3) Adeno-Associated Viral Vectors

Another type of viral vector is based on an adeno-associated virus (AAV). This defective parvovirus is a preferred vector because it can infect many cell types and is nonpathogenic to humans. AAV type vectors can transport about 4 to 5 kb and wild type AAV is known to stably insert into chromosome 19 (such as, for example at AAV integration site 1 (AAVS1)). Vectors which contain this site-specific integration property are preferred. An especially preferred embodiment of this type of vector is the P4.1 C vector produced by Avigen, San Francisco, CA, which can contain the herpes simplex virus thymidine kinase gene, HSV-tk, and/or a marker gene, such as the gene encoding the green fluorescent protein, GFP.

In another type of AAV virus, the AAV contains a pair of inverted terminal repeats (ITRs) which flank at least one cassette containing a promoter which directs cell-specific expression operably linked to a heterologous gene. Heterologous in this context refers to any nucleotide sequence or gene which is not native to the AAV or B19 parvovirus.

Typically the AAV and B19 coding regions have been deleted, resulting in a safe, noncytotoxic vector. The AAV ITRs, or modifications thereof, confer infectivity and site-specific integration, but not cytotoxicity, and the promoter directs cell-specific expression. U.S. Pat. No. 6,261,834 is herein incorporated by reference for material related to the AAV vector.

The disclosed vectors thus provide DNA molecules which are capable of integration into a mammalian chromosome without substantial toxicity.

The inserted genes in viral and retroviral usually contain promoters, and/or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and may contain upstream elements and response elements.

(4) Large Payload Viral Vectors

Molecular genetic experiments with large human herpesviruses have provided a means whereby large heterologous DNA fragments can be cloned, propagated and established in cells permissive for infection with herpesviruses (Sun et al., *Nature genetics* 8: 33-41, 1994; Cotter and Robertson, *Curr Opin Mol Ther* 5: 633-644, 1999). These large DNA viruses (herpes simplex virus (HSV) and Epstein-Barr virus (EBV), have the potential to deliver fragments of human heterologous DNA >150 kb to specific cells. EBV recombinants can maintain large pieces of DNA in the infected B-cells as episomal DNA. Individual clones carried human genomic inserts up to 330 kb appeared genetically stable The maintenance of these episomes requires a specific EBV nuclear protein, EBNA1, constitutively expressed during infection with EBV. Additionally, these vectors can be used for transfection, where large amounts of protein can be generated transiently in vitro. Herpesvirus amplicon systems are also being used to package pieces of DNA >220 kb and to infect cells that can stably maintain DNA as episomes.

Other useful systems include, for example, replicating and host-restricted non-replicating vaccinia virus vectors.

b) Non-Nucleic Acid Based Systems

The disclosed compositions can be delivered to the target cells in a variety of ways. For example, the compositions can be delivered through electroporation, or through lipofection, or through calcium phosphate precipitation. The delivery mechanism chosen will depend in part on the type of cell targeted and whether the delivery is occurring for example in vivo or in vitro.

Thus, the compositions can comprise, in addition to the disclosed modified DAP12 or vectors for example, lipids such as liposomes, such as cationic liposomes (e.g., DOTMA, DOPE, DC-cholesterol) or anionic liposomes. Liposomes can further comprise proteins to facilitate targeting a particular cell, if desired. Administration of a composition comprising a compound and a cationic liposome can be administered to the blood afferent to a target organ or inhaled into the respiratory tract to target cells of the respiratory tract. Regarding liposomes, see, e.g., Brigham et al. *Am. J. Resp. Cell. Mol. Biol.* 1:95-100 (1989); Felgner et al. *Proc. Natl. Acad. Sci USA* 84:7413-7417 (1987); U.S. Pat. No. 4,897,355. Furthermore, the compound can be administered as a component of a microcapsule that can be targeted to specific cell types, such as macrophages, or where the diffusion of the compound or delivery of the compound from the microcapsule is designed for a specific rate or dosage.

In the methods described above which include the administration and uptake of exogenous DNA into the cells of a subject (i.e., gene transduction or transfection), delivery of the compositions to cells can be via a variety of mechanisms. As one example, delivery can be via a liposome, using commercially available liposome preparations such as LIPOFECTIN, LIPOFECTAMINE (GIBCO-BRL, Inc., Gaithersburg, MD), SUPERFECT (Qiagen, Inc. Hilden, Germany) and TRANSFECTAM (Promega Biotec, Inc., Madison, WI), as well as other liposomes developed according to procedures standard in the art. In addition, the disclosed nucleic acid or vector can be delivered in vivo by electroporation, the technology for which is available from Genetronics, Inc. (San Diego, CA) as well as by means of a SONOPORATION machine (ImaRx Pharmaceutical Corp., Tucson, AZ).

The materials may be in solution, suspension (for example, incorporated into microparticles, liposomes, or cells). These may be targeted to a particular cell type via antibodies, receptors, or receptor ligands. The following references are examples of the use of this technology to target specific proteins to tumor tissue (Senter, et al., *Bioconjugate Chem.*, 2:447-451, (1991); Bagshawe, K. D., *Br. J. Cancer*, 60:275-281, (1989); Bagshawe, et al., *Br. J. Cancer*, 58:700-703, (1988); Senter, et al., *Bioconjugate Chem.*, 4:3-9, (1993); Battelli, et al., *Cancer Immunol. Immunother.*, 35:421-425, (1992); Pietersz and McKenzie, *Immunolog. Reviews*, 129:57-80, (1992); and Roffler, et al., *Biochem. Pharmacol*, 42:2062-2065, (1991)). These techniques can be used for a variety of other specific cell types. Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., *Cancer Research*, 49:6214-6220, (1989); and Litzinger and Huang, *Biochimica et Biophysica Acta*, 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, *DNA and Cell Biology* 10:6, 399-409 (1991)).

Nucleic acids that are delivered to cells which are to be integrated into the host cell genome, typically contain integration sequences. These sequences are often viral related sequences, particularly when viral based systems are used. These viral intergration systems can also be incorporated into nucleic acids which are to be delivered using a non-nucleic acid based system of deliver, such as a liposome, so that the nucleic acid contained in the delivery system can become integrated into the host genome.

Other general techniques for integration into the host genome include, for example, systems designed to promote homologous recombination with the host genome. These systems typically rely on sequence flanking the nucleic acid to be expressed that has enough homology with a target sequence within the host cell genome that recombination between the vector nucleic acid and the target nucleic acid takes place, causing the delivered nucleic acid to be integrated into the host genome. These systems and the methods necessary to promote homologous recombination are known to those of skill in the art.

c) In Vivo/Ex Vivo

As described above, the compositions can be administered in a pharmaceutically acceptable carrier and can be delivered to the subject=s cells in vivo and/or ex vivo by a variety of mechanisms well known in the art (e.g., uptake of naked DNA, liposome fusion, intramuscular injection of DNA via a gene gun, endocytosis and the like).

If ex vivo methods are employed, cells or tissues can be removed and maintained outside the body according to standard protocols well known in the art. The compositions can be introduced into the cells via any gene transfer mechanism, such as, for example, calcium phosphate mediated gene delivery, electroporation, microinjection or proteoliposomes. The transduced cells can then be infused (e.g., in a pharmaceutically acceptable carrier) or homotopically transplanted back into the subject per standard methods for the cell or tissue type. Standard methods are known for transplantation or infusion of various cells into a subject.

4. Expression Systems

The nucleic acids that are delivered to cells typically contain expression controlling systems. For example, the inserted genes in viral and retroviral systems usually contain promoters, and/or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and may contain upstream elements and response elements.

a) Viral Promoters and Enhancers

Preferred promoters controlling transcription from vectors in mammalian host cells may be obtained from various sources, for example, the genomes of viruses such as: polyoma, Simian Virus 40 (SV40), adenovirus, retroviruses, hepatitis-B virus and most preferably cytomegalovirus, or from heterologous mammalian promoters, e.g. beta actin promoter. The early and late promoters of the SV40 virus are conveniently obtained as an SV40 restriction fragment which also contains the SV40 viral origin of replication (Fiers et al., *Nature,* 273: 113 (1978)). The immediate early promoter of the human cytomegalovirus is conveniently obtained as a HindIII E restriction fragment (Greenway, P. J. et al., *Gene* 18: 355-360 (1982)). Of course, promoters from the host cell or related species also are useful herein.

Enhancer generally refers to a sequence of DNA that functions at no fixed distance from the transcription start site and can be either 5' (Laimins, L. et al., *Proc. Natl. Acad. Sci.* 78: 993 (1981)) or 3' (Lusky, M. L., et al., *Mol. Cell Bio.* 3: 1108 (1983)) to the transcription unit. Furthermore, enhancers can be within an intron (Banerji, J. L. et al., *Cell* 33: 729 (1983)) as well as within the coding sequence itself (Osborne, T. F., et al., *Mol. Cell Bio.* 4: 1293 (1984)). They are usually between 10 and 300 bp in length, and they function in cis. Enhancers function to increase transcription from nearby promoters. Enhancers also often contain response elements that mediate the regulation of transcription. Promoters can also contain response elements that mediate the regulation of transcription. Enhancers often determine the regulation of expression of a gene. While many enhancer sequences are now known from mammalian genes (globin, elastase, albumin, -fetoprotein and insulin), typically one will use an enhancer from a eukaryotic cell virus for general expression. Preferred examples are the SV40 enhancer on the late side of the replication origin (bp 100-270), the cytomegalovirus early promoter enhancer, the polyoma enhancer on the late side of the replication origin, and adenovirus enhancers.

The promotor and/or enhancer may be specifically activated either by light or specific chemical events which trigger their function. Systems can be regulated by reagents such as tetracycline and dexamethasone. There are also ways to enhance viral vector gene expression by exposure to irradiation, such as gamma irradiation, or alkylating chemotherapy drugs.

In certain embodiments the promoter and/or enhancer region can act as a constitutive promoter and/or enhancer to maximize expression of the region of the transcription unit to be transcribed. In certain constructs the promoter and/or enhancer region be active in all eukaryotic cell types, even if it is only expressed in a particular type of cell at a particular time. A preferred promoter of this type is the CMV promoter (650 bases). Other preferred promoters are SV40 promoters, cytomegalovirus (full length promoter), and retroviral vector LTR. In some aspects, the DAP12 is under control of a constitutive promoter.

It has been shown that all specific regulatory elements can be cloned and used to construct expression vectors that are selectively expressed in specific cell types such as melanoma cells. The glial fibrillary acetic protein (GFAP) promoter has been used to selectively express genes in cells of glial origin.

Expression vectors used in eukaryotic host cells (yeast, fungi, insect, plant, animal, human or nucleated cells) may also contain sequences necessary for the termination of transcription which may affect mRNA expression. These regions are transcribed as polyadenylated segments in the untranslated portion of the mRNA encoding tissue factor protein. The 3' untranslated regions also include transcription termination sites. It is preferred that the transcription unit also contains a polyadenylation region. One benefit of this region is that it increases the likelihood that the transcribed unit will be processed and transported like mRNA. The identification and use of polyadenylation signals in expression constructs is well established. It is preferred that homologous polyadenylation signals be used in the transgene constructs. In certain transcription units, the polyadenylation region is derived from the SV40 early polyadenylation signal and consists of about 400 bases. It is also preferred that the transcribed units contain other standard sequences alone or in combination with the above sequences improve expression from, or stability of, the construct.

b) Markers

The viral vectors can include nucleic acid sequence encoding a marker product. This marker product is used to determine if the gene has been delivered to the cell and once delivered is being expressed. Preferred marker genes are the *E. Coli* lacZ gene, which encodes ß-galactosidase, and green fluorescent protein.

In some embodiments the marker may be a selectable marker. Examples of suitable selectable markers for mammalian cells are dihydrofolate reductase (DHFR), thymidine kinase, neomycin, neomycin analog G418, hydromycin, and puromycin. When such selectable markers are successfully transferred into a mammalian host cell, the transformed mammalian host cell can survive if placed under selective pressure. There are two widely used distinct categories of selective regimes. The first category is based on a cell's metabolism and the use of a mutant cell line which lacks the ability to grow independent of a supplemented media. Two examples are: CHO DHFR− cells and mouse LTK− cells. These cells lack the ability to grow without the addition of such nutrients as thymidine or hypoxanthine. Because these cells lack certain genes necessary for a complete nucleotide synthesis pathway, they cannot survive unless the missing nucleotides are provided in a supplemented media. An alternative to supplementing the media is to introduce an intact DHFR or TK gene into cells lacking the respective genes, thus altering their growth requirements. Individual cells which were not transformed with the DHFR or TK gene will not be capable of survival in non-supplemented media.

The second category is dominant selection which refers to a selection scheme used in any cell type and does not require the use of a mutant cell line. These schemes typically use a drug to arrest growth of a host cell. Those cells which have a novel gene would express a protein conveying drug resistance and would survive the selection. Examples of such dominant selection use the drugs neomycin, (Southern P. and Berg, P., *J. Molec. Appl. Genet.* 1: 327 (1982)), mycophenolic acid, (Mulligan, R. C. and Berg, P. *Science* 209: 1422 (1980)) or hygromycin, (Sugden, B. et al., *Mol. Cell. Biol.* 5: 410-413 (1985)). The three examples employ bacterial genes under eukaryotic control to convey resistance to the appropriate drug G418 or neomycin (geneticin), xgpt (mycophenolic acid) or hygromycin, respectively. Others include the neomycin analog G418 and puramycin.

5. Immunoassays and Fluorochromes

The steps of various useful immunodetection methods have been described in the scientific literature, such as, e.g., Maggio et al., Enzyme-Immunoassay, (1987) and Nakamura, et al., Enzyme Immunoassays: Heterogeneous and Homogeneous Systems, Handbook of Experimental Immunology, Vol. 1: Immunochemistry, 27.1-27.20 (1986), each of which is incorporated herein by reference in its entirety and specifically for its teaching regarding immunodetection methods. Immunoassays, in their most simple and direct sense, are binding assays involving binding between antibodies and antigen. Many types and formats of immunoassays are known and all are suitable for detecting the disclosed biomarkers. Examples of immunoassays are enzyme linked immunosorbent assays (ELISAs), radioimmunoassays (RIA), radioimmune precipitation assays (RIPA), immunobead capture assays, Western blotting, dot blotting, gel-shift assays, Flow cytometry, protein arrays, multiplexed bead arrays, magnetic capture, in vivo imaging, fluorescence resonance energy transfer (FRET), and fluorescence recovery/localization after photobleaching (FRAP/FLAP).

In general, immunoassays involve contacting a sample suspected of containing a molecule of interest (such as the disclosed biomarkers) with an antibody to the molecule of interest or contacting an antibody to a molecule of interest (such as antibodies to the disclosed biomarkers) with a molecule that can be bound by the antibody, as the case may be, under conditions effective to allow the formation of immunocomplexes. Contacting a sample with the antibody to the molecule of interest or with the molecule that can be bound by an antibody to the molecule of interest under conditions effective and for a period of time sufficient to allow the formation of immune complexes (primary immune complexes) is generally a matter of simply bringing into contact the molecule or antibody and the sample and incubating the mixture for a period of time long enough for the antibodies to form immune complexes with, i.e., to bind to, any molecules (e.g., antigens) present to which the antibodies can bind. In many forms of immunoassay, the sample-antibody composition, such as a tissue section, ELISA plate, dot blot or Western blot, can then be washed to remove any non-specifically bound antibody species, allowing only those antibodies specifically bound within the primary immune complexes to be detected.

Immunoassays can include methods for detecting or quantifying the amount of a molecule of interest (such as the disclosed biomarkers or their antibodies) in a sample, which methods generally involve the detection or quantitation of any immune complexes formed during the binding process. In general, the detection of immunocomplex formation is well known in the art and can be achieved through the application of numerous approaches. These methods are generally based upon the detection of a label or marker, such as any radioactive, fluorescent, biological or enzymatic tags or any other known label.

As used herein, a label can include a fluorescent dye, a member of a binding pair, such as biotin/streptavidin, a metal (e.g., gold), or an epitope tag that can specifically interact with a molecule that can be detected, such as by producing a colored substrate or fluorescence. Substances suitable for detectably labeling proteins include fluorescent dyes (also known herein as fluorochromes and fluorophores) and enzymes that react with colorometric substrates (e.g., horseradish peroxidase). The use of fluorescent dyes is generally preferred in the practice of the invention as they can be detected at very low amounts. Furthermore, in the case where multiple antigens are reacted with a single array, each antigen can be labeled with a distinct fluorescent compound for simultaneous detection. Labeled spots on the array are detected using a fluorimeter, the presence of a signal indicating an antigen bound to a specific antibody.

Fluorophores are compounds or molecules that luminesce. Typically fluorophores absorb electromagnetic energy at one wavelength and emit electromagnetic energy at a second wavelength. Representative fluorophores include, but are not limited to, 1,5 IAEDANS; 1,8-ANS; 4-Methylumbelliferone; 5-carboxy-2,7-dichlorofluorescein; 5-Carboxyfluorescein (5-FAM); 5-Carboxynapthofluorescein; 5-Carboxytetramethylrhodamine (5-TAMRA); 5-Hydroxy Tryptamine (5-HAT); 5-ROX (carboxy-X-rhodamine); 6-Carboxyrhodamine 6G; 6-CR 6G; 6-JOE; 7-Amino-4-methylcoumarin; 7-Aminoactinomycin D (7-AAD); 7-Hydroxy-4-I methylcoumarin; 9-Amino-6-chloro-2-methoxyacridine (ACMA); ABQ; Acid Fuchsin; Acridine Orange; Acridine Red; Acridine Yellow; Acriflavin; Acriflavin Feulgen SITSA; Aequorin (Photoprotein); AFPs—AutoFluorescent Protein—(Quantum Biotechnologies) see sgGFP, sgBFP; Alexa Fluor 350™; Alexa Fluor 430™; Alexa Fluor 488™; Alexa Fluor 532™; Alexa Fluor 546™; Alexa Fluor 568™; Alexa Fluor 594™; Alexa Fluor 633™; Alexa Fluor 647™; Alexa Fluor 660™; Alexa Fluor 680™; Alizarin Complexon; Alizarin Red; Allophycocyanin (APC); AMC, AMCA-S; Aminomethylcoumarin (AMCA); AMCA-X; Aminoactinomycin D; Aminocoumarin; Anilin Blue; Anthrocyl stearate; APC-Cy7; APTRA-BTC; APTS; Astrazon Brilliant Red 4G; Astrazon Orange R; Astrazon Red 6B; Astrazon Yellow 7 GLL; Atabrine; ATTO-TAG™ CBQCA; ATTO-TAG™ FQ; Auramine; Aurophosphine G; Aurophosphine; BAO 9 (Bisaminophenyloxadiazole);

BCECF (high pH); BCECF (low pH); Berberine Sulphate; Beta Lactamase; BFP blue shifted GFP (Y66H); Blue Fluorescent Protein; BFP/GFP FRET; Bimane; Bisbenzemide; Bisbenzimide (Hoechst); bis-BTC; Blancophor FFG; Blancophor SV; BOBO™-1; BOBO™-3; Bodipy492/515; Bodipy493/503; Bodipy500/510; Bodipy; 505/515; Bodipy 530/550; Bodipy 542/563; Bodipy 558/568; Bodipy 564/570; Bodipy 576/589; Bodipy 581/591; Bodipy 630/650-X; Bodipy 650/665-X; Bodipy 665/676; Bodipy Fl; Bodipy FL ATP; Bodipy Fl-Ceramide; Bodipy R6G SE; Bodipy TMR; Bodipy TMR-X conjugate; Bodipy TMR-X, SE; Bodipy TR; Bodipy TR ATP; Bodipy TR-X SE; BO-PRO™-1; BO-PRO™-3; Brilliant Sulphoflavin FF; BTC; BTC-5N; Calcein; Calcein Blue; Calcium Crimson-; Calcium Green; Calcium Green-1 $Ca^{2+}$ Dye; Calcium Green-2 $Ca^{2+}$; Calcium Green-5N $Ca^{2+}$; Calcium Green-C18 $Ca^{2+}$; Calcium Orange; Calcofluor White; Carboxy-X-rhodamine (5-ROX); Cascade Blue™; Cascade Yellow; Catecholamine; CCF2 (GeneBlazer); CFDA; CFP (Cyan Fluorescent Protein); CFP/YFP FRET; Chlorophyll; Chromomycin A; Chromomycin A; CL-NERF; CMFDA; Coelenterazine; Coelenterazine cp; Coelenterazine f; Coelenterazine fcp; Coelenterazine h; Coelenterazine hcp; Coelenterazine ip; Coelenterazine n; Coelenterazine O; Coumarin Phalloidin; C-phycocyanine; CPM I Methylcoumarin; CTC; CTC Formazan; Cy2™; Cy3.1 8; Cy3.5™; Cy3™; Cy5.1 8; Cy5.5™; Cy5™; Cy7™; Cyan GFP; cyclic AMP Fluorosensor (FiCRhR); Dabcyl; Dansyl; Dansyl Amine; Dansyl Cadaverine; Dansyl Chloride; Dansyl DHPE; Dansyl fluoride; DAPI; Dapoxyl; Dapoxyl 2; Dapoxyl 3'DCFDA; DCFH (Dichlorodihydrofluorescein Diacetate); DDAO; DHR (Dihydorhodamine 123); Di-4-ANEPPS; Di-8-ANEPPS (non-ratio); DiA (4-Di 16-ASP); Dichlorodihydrofluorescein Diacetate (DCFH); DiD-Lipophilic Tracer; DiD (DiIC18(5)); DIDS; Dihydrohodamine 123 (DHR); DiI (DiIC18(3)); I Dinitrophenol; DiO (DiOC18(3)); DiR; DiR (DiIC18(7)); DM-NERF (high pH); DNP; Dopamine; DsRed; DTAF; DY-630-NHS; DY-635-NHS; EBFP; ECFP; EGFP; ELF 97; Eosin; Erythrosin; Erythrosin ITC; Ethidium Bromide; Ethidium homodimer-1 (EthD-1); Euchrysin; EukoLight; Europium (111) chloride; EYFP; Fast Blue; FDA; Feulgen (Pararosaniline); FIF (Formaldehyd Induced Fluorescence); FITC; Flazo Orange; Fluo-3; Fluo-4; Fluorescein (FITC); Fluorescein Diacetate; Fluoro-Emerald; Fluoro-Gold (Hydroxystilbamidine); Fluor-Ruby; FluorX; FM 1-43™; FM 4-46; Fura Red™ (high pH); Fura Red™/Fluo-3; Fura-2; Fura-2/BCECF; Genacryl Brilliant Red B; Genacryl Brilliant Yellow 10GF; Genacryl Pink 3G; Genacryl Yellow 5GF; GeneBlazer; (CCF2); GFP (S65T); GFP red shifted (rsGFP); GFP wild type' non-UV excitation (wtGFP); GFP wild type, UV excitation (wtGFP); GFPuv; Gloxalic Acid; Granular blue; Haematoporphyrin; Hoechst 33258; Hoechst 33342; Hoechst 34580; HPTS; Hydroxycoumarin; Hydroxystilbamidine (FluoroGold); Hydroxytryptamine; Indo-1, high calcium; Indo-1 low calcium; Indodicarbocyanine (DiD); Indotricarbocyanine (DiR); Intrawhite Cf; JC-1; JO JO-1; JO-PRO-1; LaserPro; Laurodan; LDS 751 (DNA); LDS 751 (RNA); Leucophor PAF; Leucophor SF; Leucophor WS; Lissamine Rhodamine; Lissamine Rhodamine B; Calcein/Ethidium homodimer; LOLO-1; LO-PRO-1; Lucifer Yellow; Lyso Tracker Blue; Lyso Tracker Blue-White; Lyso Tracker Green; Lyso Tracker Red; Lyso Tracker Yellow; LysoSensor Blue; LysoSensor Green; LysoSensor Yellow/Blue; Mag Green; Magdala Red (Phloxin B); Mag-Fura Red; Mag-Fura-2; Mag-Fura-5; Mag-lndo-1; Magnesium Green; Magnesium Orange; Malachite Green; Marina Blue; I Maxilon Brilliant Flavin 10 GFF; Maxilon Brilliant Flavin 8 GFF; Merocyanin; Methoxycoumarin; Mitotracker Green FM; Mitotracker Orange; Mitotracker Red; Mitramycin; Monobromobimane; Monobromobimane (mBBr-GSH); Monochlorobimane; MPS (Methyl Green Pyronine Stilbene); NBD; NBD Amine; Nile Red; Nitrobenzoxedidole; Noradrenaline; Nuclear Fast Red; i Nuclear Yellow; Nylosan Brilliant lavin E8G; Oregon Green™; Oregon Green™ 488; Oregon Green™ 500; Oregon Green™ 514; Pacific Blue; Pararosaniline (Feulgen); PBFI; PE-Cy5; PE-Cy7; PerCP; PerCP-Cy5.5; PE-TexasRed (Red 613); Phloxin B (Magdala Red); Phorwite AR; Phorwite BKL; Phorwite Rev; Phorwite RPA; Phosphine 3R; PhotoResist; Phycoerythrin B [PE]; Phycoerythrin R [PE]; PKH26 (Sigma); PKH67; PMIA; Pontochrome Blue Black; POPO-1; POPO-3; PO-PRO-1; PO-I PRO-3; Primuline; Procion Yellow; Propidium lodid (Pl); PyMPO; Pyrene; Pyronine; Pyronine B; Pyrozal Brilliant Flavin 7GF; QSY 7; Quinacrine Mustard; Resorufin; RH 414; Rhod-2; Rhodamine; Rhodamine 110; Rhodamine 123; Rhodamine 5 GLD; Rhodamine 6G; Rhodamine B; Rhodamine B 200; Rhodamine B extra; Rhodamine BB; Rhodamine BG; Rhodamine Green; Rhodamine Phallicidine; Rhodamine: Phalloidine; Rhodamine Red; Rhodamine WT; Rose Bengal; R-phycocyanine; R-phycoerythrin (PE); rsGFP; S65A; S65C; S65L; S65T; Sapphire GFP; SBFI; Serotonin; Sevron Brilliant Red 2B; Sevron Brilliant Red 4G; Sevron I Brilliant Red B; Sevron Orange; Sevron Yellow L; sgBFP™ (super glow BFP); sgGFP™ (super glow GFP); SITS (Primuline; Stilbene Isothiosulphonic Acid); SNAFL calcein; SNAFL-1; SNAFL-2; SNARF calcein; SNARF1; Sodium Green; SpectrumAqua; SpectrumGreen; SpectrumOrange; Spectrum Red; SPQ (6-methoxy-N-(3 sulfopropyl) quinolinium); Stilbene; Sulphorhodamine B and C; Sulphorhodamine Extra; SYTO 11; SYTO 12; SYTO 13; SYTO 14; SYTO 15; SYTO 16; SYTO 17; SYTO 18; SYTO 20; SYTO 21; SYTO 22; SYTO 23; SYTO 24; SYTO 25; SYTO 40; SYTO 41; SYTO 42; SYTO 43; SYTO 44; SYTO 45; SYTO 59; SYTO 60; SYTO 61; SYTO 62; SYTO 63; SYTO 64; SYTO 80; SYTO 81; SYTO 82; SYTO 83; SYTO 84; SYTO 85; SYTOX Blue; SYTOX Green; SYTOX Orange; Tetracycline; Tetramethylrhodamine (TRITC); Texas Red™; Texas Red-X™ conjugate; Thiadicarbocyanine (DiSC3); Thiazine Red R; Thiazole Orange; Thioflavin 5; Thioflavin S; Thioflavin TON; Thiolyte; Thiozole Orange; Tinopol CBS (Calcofluor White); TIER; TO-PRO-1; TO-PRO-3; TO-PRO-5; TOTO-1; TOTO-3; TriColor (PE-Cy5); TRITC TetramethylRodaminelsoThioCyanate; True Blue; Tru Red; Ultralite; Uranine B; Uvitex SFC; wt GFP; WW 781; X-Rhodamine; XRITC; Xylene Orange; Y66F; Y66H; Y66W; Yellow GFP; YFP; YO-PRO-1; YO-PRO 3; YOYO-1; YOYO-3; Sybr Green; Thiazole orange (interchelating dyes); semiconductor nanoparticles such as quantum dots; or caged fluorophore (which can be activated with light or other electromagnetic energy source), or a combination thereof.

A modifier unit such as a radionuclide can be incorporated into or attached directly to any of the compounds described herein by halogenation. Examples of radionuclides useful in this embodiment include, but are not limited to, tritium, iodine-125, iodine-131, iodine-123, iodine-124, astatine-210, carbon-11, carbon-14, nitrogen-13, fluorine-18. In another aspect, the radionuclide can be attached to a linking group or bound by a chelating group, which is then attached to the compound directly or by means of a linker. Examples of radionuclides useful in the aspect include, but are not limited to, Tc-99m, Re-186, Ga-68, Re-188, Y-90, Sm-153, Bi-212, Cu-67, Cu-64, and Cu-62. Radiolabeling techniques such as these are routinely used in the radiopharmaceutical industry.

The radiolabeled compounds are useful as imaging agents to diagnose neurological disease (e.g., a neurodegenerative disease) or a mental condition or to follow the progression or treatment of such a disease or condition in a mammal (e.g., a human). The radiolabeled compounds described herein can be conveniently used in conjunction with imaging techniques such as positron emission tomography (PET) or single photon emission computerized tomography (SPECT).

Labeling can be either direct or indirect. In direct labeling, the detecting antibody (the antibody for the molecule of interest) or detecting molecule (the molecule that can be bound by an antibody to the molecule of interest) include a label. Detection of the label indicates the presence of the detecting antibody or detecting molecule, which in turn indicates the presence of the molecule of interest or of an antibody to the molecule of interest, respectively. In indirect labeling, an additional molecule or moiety is brought into contact with, or generated at the site of, the immunocomplex. For example, a signal-generating molecule or moiety such as an enzyme can be attached to or associated with the detecting antibody or detecting molecule. The signal-generating molecule can then generate a detectable signal at the site of the immunocomplex. For example, an enzyme, when supplied with suitable substrate, can produce a visible or detectable product at the site of the immunocomplex. ELISAs use this type of indirect labeling.

As another example of indirect labeling, an additional molecule (which can be referred to as a binding agent) that can bind to either the molecule of interest or to the antibody (primary antibody) to the molecule of interest, such as a second antibody to the primary antibody, can be contacted with the immunocomplex. The additional molecule can have a label or signal-generating molecule or moiety. The additional molecule can be an antibody, which can thus be termed a secondary antibody. Binding of a secondary antibody to the primary antibody can form a so-called sandwich with the first (or primary) antibody and the molecule of interest. The immune complexes can be contacted with the labeled, secondary antibody under conditions effective and for a period of time sufficient to allow the formation of secondary immune complexes. The secondary immune complexes can then be generally washed to remove any non-specifically bound labeled secondary antibodies, and the remaining label in the secondary immune complexes can then be detected. The additional molecule can also be or include one of a pair of molecules or moieties that can bind to each other, such as the biotin/avadin pair. In this mode, the detecting antibody or detecting molecule should include the other member of the pair.

Other modes of indirect labeling include the detection of primary immune complexes by a two step approach. For example, a molecule (which can be referred to as a first binding agent), such as an antibody, that has binding affinity for the molecule of interest or corresponding antibody can be used to form secondary immune complexes, as described above. After washing, the secondary immune complexes can be contacted with another molecule (which can be referred to as a second binding agent) that has binding affinity for the first binding agent, again under conditions effective and for a period of time sufficient to allow the formation of immune complexes (thus forming tertiary immune complexes). The second binding agent can be linked to a detectable label or signal-generating molecule or moiety, allowing detection of the tertiary immune complexes thus formed. This system can provide for signal amplification.

Immunoassays that involve the detection of as substance, such as a protein or an antibody to a specific protein, include label-free assays, protein separation methods (i.e., electrophoresis), solid support capture assays, or in vivo detection. Label-free assays are generally diagnostic means of determining the presence or absence of a specific protein, or an antibody to a specific protein, in a sample. Protein separation methods are additionally useful for evaluating physical properties of the protein, such as size or net charge. Capture assays are generally more useful for quantitatively evaluating the concentration of a specific protein, or antibody to a specific protein, in a sample. Finally, in vivo detection is useful for evaluating the spatial expression patterns of the substance, i.e., where the substance can be found in a subject, tissue or cell.

Provided that the concentrations are sufficient, the molecular complexes ([Ab-Ag]n) generated by antibody-antigen interaction are visible to the naked eye, but smaller amounts may also be detected and measured due to their ability to scatter a beam of light. The formation of complexes indicates that both reactants are present, and in immunoprecipitation assays a constant concentration of a reagent antibody is used to measure specific antigen ([Ab-Ag]n), and reagent antigens are used to detect specific antibody ([Ab-Ag]n). If the reagent species is previously coated onto cells (as in hemagglutination assay) or very small particles (as in latex agglutination assay), "clumping" of the coated particles is visible at much lower concentrations. A variety of assays based on these elementary principles are in common use, including Ouchterlony immunodiffusion assay, rocket immunoelectrophoresis, and immunoturbidometric and nephelometric assays. The main limitations of such assays are restricted sensitivity (lower detection limits) in comparison to assays employing labels and, in some cases, the fact that very high concentrations of analyte can actually inhibit complex formation, necessitating safeguards that make the procedures more complex. Some of these Group 1 assays date right back to the discovery of antibodies and none of them have an actual "label" (e.g. Ag-enz). Other kinds of immunoassays that are label free depend on immunosensors, and a variety of instruments that can directly detect antibody-antigen interactions are now commercially available. Most depend on generating an evanescent wave on a sensor surface with immobilized ligand, which allows continuous monitoring of binding to the ligand. Immunosensors allow the easy investigation of kinetic interactions and, with the advent of lower-cost specialized instruments, may in the future find wide application in immunoanalysis.

The use of immunoassays to detect a specific protein can involve the separation of the proteins by electophoresis. Electrophoresis is the migration of charged molecules in solution in response to an electric field. Their rate of migration depends on the strength of the field; on the net charge, size and shape of the molecules and also on the ionic strength, viscosity and temperature of the medium in which the molecules are moving. As an analytical tool, electrophoresis is simple, rapid and highly sensitive. It is used analytically to study the properties of a single charged species, and as a separation technique.

Generally the sample is run in a support matrix such as paper, cellulose acetate, starch gel, agarose or polyacrylamide gel. The matrix inhibits convective mixing caused by heating and provides a record of the electrophoretic run: at the end of the run, the matrix can be stained and used for scanning, autoradiography or storage. In addition, the most commonly used support matrices—agarose and polyacrylamide—provide a means of separating molecules by size, in that they are porous gels. A porous gel may act as a sieve by retarding, or in some cases completely obstructing, the movement of large macromolecules while allowing smaller molecules to migrate freely. Because dilute agarose gels are generally more rigid and easy to handle than polyacrylamide of the same concentration, agarose is used to separate larger macromolecules such as nucleic acids, large proteins and protein complexes. Polyacrylamide, which is easy to handle and to make at higher concentrations, is used to separate most proteins and small oligonucleotides that require a small gel pore size for retardation.

Proteins are amphoteric compounds; their net charge therefore is determined by the pH of the medium in which they are suspended. In a solution with a pH above its isoelectric point, a protein has a net negative charge and migrates towards the anode in an electrical field. Below its isoelectric point, the protein is positively charged and migrates towards the cathode. The net charge carried by a protein is in addition independent of its size—i.e., the charge carried per unit mass (or length, given proteins and nucleic acids are linear macromolecules) of molecule differs from protein to protein. At a given pH therefore, and under non-denaturing conditions, the electrophoretic separation of proteins is determined by both size and charge of the molecules.

Sodium dodecyl sulphate (SDS) is an anionic detergent which denatures proteins by "wrapping around" the polypeptide backbone—and SDS binds to proteins fairly specifically in a mass ratio of 1.4:1. In so doing, SDS confers a negative charge to the polypeptide in proportion to its length. Further, it is usually necessary to reduce disulphide bridges in proteins (denature) before they adopt the random-coil configuration necessary for separation by size; this is done with 2-mercaptoethanol or dithiothreitol (DTT). In denaturing SDS-PAGE separations therefore, migration is determined not by intrinsic electrical charge of the polypeptide, but by molecular weight.

Determination of molecular weight is done by SDS-PAGE of proteins of known molecular weight along with the protein to be characterized. A linear relationship exists between the logarithm of the molecular weight of an SDS-denatured polypeptide, or native nucleic acid, and its Rf. The Rf is calculated as the ratio of the distance migrated by the molecule to that migrated by a marker dye-front. A simple way of determining relative molecular weight by electrophoresis (Mr) is to plot a standard curve of distance migrated vs. log 10MW for known samples, and read off the log Mr of the sample after measuring distance migrated on the same gel.

In two-dimensional electrophoresis, proteins are fractionated first on the basis of one physical property, and, in a second step, on the basis of another. For example, isoelectric focusing can be used for the first dimension, conveniently carried out in a tube gel, and SDS electrophoresis in a slab gel can be used for the second dimension. One example of a procedure is that of O'Farrell, P. H., High Resolution Two-dimensional Electrophoresis of Proteins, J. Biol. Chem. 250:4007-4021 (1975), herein incorporated by reference in its entirety for its teaching regarding two-dimensional electrophoresis methods. Other examples include but are not limited to, those found in Anderson, L and Anderson, N G, High resolution two-dimensional electrophoresis of human plasma proteins, Proc. Natl. Acad. Sci. 74:5421-5425 (1977), Ornstein, L., Disc electrophoresis, L. Ann. N.Y. Acad. Sci. 121:321349 (1964), each of which is herein incorporated by reference in its entirety for teachings regarding electrophoresis methods. Laemmli, U. K., Cleavage of structural proteins during the assembly of the head of bacteriophage T4, Nature 227:680 (1970), which is herein incorporated by reference in its entirety for teachings regarding electrophoresis methods, discloses a discontinuous system for resolving proteins denatured with SDS. The leading ion in the Laemmli buffer system is chloride, and the trailing ion is glycine. Accordingly, the resolving gel and the stacking gel are made up in Tris-HCl buffers (of different concentration and pH), while the tank buffer is Tris-glycine. All buffers contain 0.1% SDS.

One example of an immunoassay that uses electrophoresis that is contemplated in the current methods is Western blot analysis. Western blotting or immunoblotting allows the determination of the molecular mass of a protein and the measurement of relative amounts of the protein present in different samples. Detection methods include chemiluminescence and chromagenic detection. Standard methods for Western blot analysis can be found in, for example, D. M. Bollag et al., *Protein Methods* (2d edition 1996) and E. Harlow & D. Lane, *Antibodies, a Laboratory Manual* (1988), U.S. Pat. No. 4,452,901, each of which is herein incorporated by reference in their entirety for teachings regarding Western blot methods. Generally, proteins are separated by gel electrophoresis, usually SDS-PAGE. The proteins are transferred to a sheet of special blotting paper, e.g., nitrocellulose, though other types of paper, or membranes, can be used. The proteins retain the same pattern of separation they had on the gel. The blot is incubated with a generic protein (such as milk proteins) to bind to any remaining sticky places on the nitrocellulose. An antibody is then added to the solution which is able to bind to its specific protein.

The attachment of specific antibodies to specific immobilized antigens can be readily visualized by indirect enzyme immunoassay techniques, usually using a chromogenic substrate (e.g. alkaline phosphatase or horseradish peroxidase) or chemiluminescent substrates. Other possibilities for probing include the use of fluorescent or radioisotope labels (e.g., fluorescein, $^{125}$I). Probes for the detection of antibody binding can be conjugated anti-immunoglobulins, conjugated staphylococcal Protein A (binds IgG), or probes to biotinylated primary antibodies (e.g., conjugated avidin/streptavidin).

The power of the technique lies in the simultaneous detection of a specific protein by means of its antigenicity, and its molecular mass. Proteins are first separated by mass in the SDS-PAGE, then specifically detected in the immunoassay step. Thus, protein standards (ladders) can be run simultaneously in order to approximate molecular mass of the protein of interest in a heterogeneous sample.

The gel shift assay or electrophoretic mobility shift assay (EMSA) can be used to detect the interactions between DNA binding proteins and their cognate DNA recognition sequences, in both a qualitative and quantitative manner. Exemplary techniques are described in Ornstein L., Disc electrophoresis-I: Background and theory, Ann. NY Acad. Sci. 121:321-349 (1964), and Matsudiara, P T and D R Burgess, SDS microslab linear gradient polyacrylamide gel electrophoresis, Anal. Biochem. 87:386-396 (1987), each of which is herein incorporated by reference in its entirety for teachings regarding gel-shift assays.

In a general gel-shift assay, purified proteins or crude cell extracts can be incubated with a labeled (e.g., $^{32}$P-radiolabeled) DNA or RNA probe, followed by separation of the complexes from the free probe through a nondenaturing polyacrylamide gel. The complexes migrate more slowly through the gel than unbound probe. Depending on the activity of the binding protein, a labeled probe can be either double-stranded or single-stranded. For the detection of DNA binding proteins such as transcription factors, either purified or partially purified proteins, or nuclear cell extracts can be used. For detection of RNA binding proteins, either purified or partially purified proteins, or nuclear or cytoplasmic cell extracts can be used. The specificity of the DNA or RNA binding protein for the putative binding site is established by competition experiments using DNA or RNA fragments or oligonucleotides containing a binding site for the protein of interest, or other unrelated sequence. The differences in the nature and intensity of the complex formed in the presence of specific and nonspecific competitor allows identification of specific interactions. Refer to Promega, Gel Shift Assay FAQ.

Gel shift methods can include using, for example, colloidal forms of COOMASSIE (Imperial Chemicals Industries, Ltd) blue stain to detect proteins in gels such as polyacrylamide electrophoresis gels. Such methods are described, for example, in Neuhoff et al., Electrophoresis 6:427-448 (1985), and Neuhoff et al., Electrophoresis 9:255-262 (1988), each of which is herein incorporated by reference in its entirety for teachings regarding gel shift methods. In addition to the conventional protein assay methods referenced above, a combination cleaning and protein staining composition is described in U.S. Pat. No. 5,424,000, herein incorporated by reference in its entirety for its teaching regarding gel shift methods. The solutions can include phosphoric, sulfuric, and nitric acids, and Acid Violet dye.

Radioimmune Precipitation Assay (RIPA) is a sensitive assay using radiolabeled antigens to detect specific antibodies in serum. The antigens are allowed to react with the serum and then precipitated using a special reagent such as, for example, protein A sepharose beads. The bound radiolabeled immunoprecipitate is then commonly analyzed by gel electrophoresis. Radioimmunoprecipitation assay (RIPA) is often used as a confirmatory test for diagnosing the presence of HIV antibodies. RIPA is also referred to in the art as Farr Assay, Precipitin Assay, Radioimmune Precipitin Assay; Radioimmunoprecipitation Analysis; Radioimmunoprecipitation Analysis, and Radioimmunoprecipitation Analysis.

While the above immunoassays that utilize electrophoresis to separate and detect the specific proteins of interest allow for evaluation of protein size, they are not very sensitive for evaluating protein concentration. However, also contemplated are immunoassays wherein the protein or antibody specific for the protein is bound to a solid support (e.g., tube, well, bead, or cell) to capture the antibody or protein of interest, respectively, from a sample, combined with a method of detecting the protein or antibody specific for the protein on the support. Examples of such immunoassays include Radioimmunoassay (RIA), Enzyme-Linked Immunosorbent Assay (ELISA), Flow cytometry, protein array, multiplexed bead assay, and magnetic capture.

Radioimmunoassay (RIA) is a classic quantitative assay for detection of antigen-antibody reactions using a radioactively labeled substance (radioligand), either directly or indirectly, to measure the binding of the unlabeled substance to a specific antibody or other receptor system. Radioimmunoassay is used, for example, to test hormone levels in the blood without the need to use a bioassay. Non-immunogenic substances (e.g., haptens) can also be measured if coupled to larger carrier proteins (e.g., bovine gamma-globulin or human serum albumin) capable of inducing antibody formation. RIA involves mixing a radioactive antigen (because of the ease with which iodine atoms can be introduced into tyrosine residues in a protein, the radioactive isotopes $^{125}$I or $^{131}$I are often used) with antibody to that antigen. The antibody is generally linked to a solid support, such as a tube or beads. Unlabeled or "cold" antigen is then adding in known quantities and measuring the amount of labeled antigen displaced. Initially, the radioactive antigen is bound to the antibodies. When cold antigen is added, the two compete for antibody binding sites—and at higher concentrations of cold antigen, more binds to the antibody, displacing the radioactive variant. The bound antigens are separated from the unbound ones in solution and the radioactivity of each used to plot a binding curve. The technique is both extremely sensitive, and specific.

Enzyme-Linked Immunosorbent Assay (ELISA), or more generically termed EIA (Enzyme ImmunoAssay), is an immunoassay that can detect an antibody specific for a protein. In such an assay, a detectable label bound to either an antibody-binding or antigen-binding reagent is an enzyme. When exposed to its substrate, this enzyme reacts in such a manner as to produce a chemical moiety which can be detected, for example, by spectrophotometric, fluorometric or visual means. Enzymes which can be used to detectably label reagents useful for detection include, but are not limited to, horseradish peroxidase, alkaline phosphatase, glucose oxidase, β-galactosidase, ribonuclease, urease, catalase, malate dehydrogenase, staphylococcal nuclease, asparaginase, yeast alcohol dehydrogenase, alpha.-glycerophosphate dehydrogenase, triose phosphate isomerase, glucose-6-phosphate dehydrogenase, glucoamylase and acetylcholinesterase.

Variations of ELISA techniques are know to those of skill in the art. In one variation, antibodies that can bind to proteins can be immobilized onto a selected surface exhibiting protein affinity, such as a well in a polystyrene microtiter plate. Then, a test composition suspected of containing a marker antigen can be added to the wells. After binding and washing to remove non-specifically bound immunocomplexes, the bound antigen can be detected. Detection can be achieved by the addition of a second antibody specific for the target protein, which is linked to a detectable label. This type of ELISA is a simple "sandwich ELISA." Detection also can be achieved by the addition of a second antibody, followed by the addition of a third antibody that has binding affinity for the second antibody, with the third antibody being linked to a detectable label.

Another variation is a competition ELISA. In competition ELISA's, test samples compete for binding with known amounts of labeled antigens or antibodies. The amount of reactive species in the sample can be determined by mixing the sample with the known labeled species before or during incubation with coated wells. The presence of reactive species in the sample acts to reduce the amount of labeled species available for binding to the well and thus reduces the ultimate signal.

Regardless of the format employed, ELISAs have certain features in common, such as coating, incubating or binding, washing to remove non-specifically bound species, and detecting the bound immunecomplexes. Antigen or antibodies can be linked to a solid support, such as in the form of plate, beads, dipstick, membrane or column matrix, and the sample to be analyzed applied to the immobilized antigen or antibody. In coating a plate with either antigen or antibody, one will generally incubate the wells of the plate with a solution of the antigen or antibody, either overnight or for a specified period of hours. The wells of the plate can then be washed to remove incompletely adsorbed material. Any remaining available surfaces of the wells can then be "coated" with a nonspecific protein that is antigenically neutral with regard to the test antisera. These include bovine serum albumin (BSA), casein and solutions of milk powder. The coating allows for blocking of nonspecific adsorption sites on the immobilizing surface and thus reduces the background caused by nonspecific binding of antisera onto the surface.

In ELISAs, a secondary or tertiary detection means rather than a direct procedure can also be used. Thus, after binding of a protein or antibody to the well, coating with a non-reactive material to reduce background, and washing to remove unbound material, the immobilizing surface is contacted with the control clinical or biological sample to be tested under conditions effective to allow immunecomplex (antigen/antibody) formation. Detection of the immunecomplex then requires a labeled secondary binding agent or a secondary binding agent in conjunction with a labeled third binding agent.

Enzyme-Linked Immunospot Assay (ELISPOT) is an immunoassay that can detect an antibody specific for a protein or antigen. In such an assay, a detectable label bound to either an antibody-binding or antigen-binding reagent is an enzyme. When exposed to its substrate, this enzyme reacts in such a manner as to produce a chemical moiety which can be detected, for example, by spectrophotometric, fluorometric or visual means. Enzymes which can be used to detectably label reagents useful for detection include, but are not limited to, horseradish peroxidase, alkaline phosphatase, glucose oxidase, β-galactosidase, ribonuclease, urease, catalase, malate dehydrogenase, staphylococcal nuclease, asparaginase, yeast alcohol dehydrogenase, alpha.-glycerophosphate dehydrogenase, triose phosphate isomerase, glucose-6-phosphate dehydrogenase, glucoamylase and acetylcholinesterase. In this assay a nitrocellulose microtiter plate is coated with antigen. The test sample is exposed to the antigen and then reacted similarly to an ELISA assay. Detection differs from a traditional ELISA in that detection is determined by the enumeration of spots on the nitrocellulose plate. The presence of a spot indicates that the sample reacted to the antigen. The spots can be counted and the number of cells in the sample specific for the antigen determined.

"Under conditions effective to allow immunecomplex (antigen/antibody) formation" means that the conditions include diluting the antigens and antibodies with solutions such as BSA, bovine gamma globulin (BGG) and phosphate buffered saline (PBS)/Tween so as to reduce non-specific binding and to promote a reasonable signal to noise ratio.

The suitable conditions also mean that the incubation is at a temperature and for a period of time sufficient to allow effective binding. Incubation steps can typically be from about 1 minute to twelve hours, at temperatures of about 20° to 30° C., or can be incubated overnight at about 0° C. to about 10° C.

Following all incubation steps in an ELISA, the contacted surface can be washed so as to remove non-complexed material. A washing procedure can include washing with a solution such as PBS/Tween or borate buffer. Following the formation of specific immunecomplexes between the test sample and the originally bound material, and subsequent washing, the occurrence of even minute amounts of immunecomplexes can be determined.

To provide a detecting means, the second or third antibody can have an associated label to allow detection, as described above. This can be an enzyme that can generate color development upon incubating with an appropriate chromogenic substrate. Thus, for example, one can contact and incubate the first or second immunecomplex with a labeled antibody for a period of time and under conditions that favor the development of further immunecomplex formation (e.g., incubation for 2 hours at room temperature in a PBS-containing solution such as PBS-Tween).

After incubation with the labeled antibody, and subsequent to washing to remove unbound material, the amount of label can be quantified, e.g., by incubation with a chromogenic substrate such as urea and bromocresol purple or 2,2'-azido-di-(3-ethyl-benzothiazoline-6-sulfonic acid [ABTS] and $H_2O_2$, in the case of peroxidase as the enzyme label. Quantitation can then be achieved by measuring the degree of color generation, e.g., using a visible spectra spectrophotometer.

Protein arrays are solid-phase ligand binding assay systems using immobilized proteins on surfaces which include glass, membranes, microtiter wells, mass spectrometer plates, and beads or other particles. The assays are highly parallel (multiplexed) and often miniaturized (microarrays, protein chips). Their advantages include being rapid and automatable, capable of high sensitivity, economical on reagents, and giving an abundance of data for a single experiment. Bioinformatics support is important; the data handling demands sophisticated software and data comparison analysis. However, the software can be adapted from that used for DNA arrays, as can much of the hardware and detection systems.

One of the chief formats is the capture array, in which ligand-binding reagents, which are usually antibodies but can also be alternative protein scaffolds, peptides or nucleic acid aptamers, are used to detect target molecules in mixtures such as plasma or tissue extracts. In diagnostics, capture arrays can be used to carry out multiple immunoassays in parallel, both testing for several analytes in individual sera for example and testing many serum samples simultaneously. In proteomics, capture arrays are used to quantitate and compare the levels of proteins in different samples in health and disease, i.e. protein expression profiling. Proteins other than specific ligand binders are used in the array format for in vitro functional interaction screens such as protein-protein, protein-DNA, protein-drug, receptor-ligand, enzyme-substrate, etc. The capture reagents themselves are selected and screened against many proteins, which can also be done in a multiplex array format against multiple protein targets.

For construction of arrays, sources of proteins include cell-based expression systems for recombinant proteins, purification from natural sources, production in vitro by cell-free translation systems, and synthetic methods for peptides. Many of these methods can be automated for high throughput production. For capture arrays and protein function analysis, it is important that proteins should be correctly folded and functional; this is not always the case, e.g. where recombinant proteins are extracted from bacteria under denaturing conditions. Nevertheless, arrays of denatured proteins are useful in screening antibodies for cross-reactivity, identifying autoantibodies and selecting ligand binding proteins.

Protein arrays have been designed as a miniaturization of familiar immunoassay methods such as ELISA and dot blotting, often utilizing fluorescent readout, and facilitated by robotics and high throughput detection systems to enable multiple assays to be carried out in parallel. Commonly used physical supports include glass slides, silicon, microwells, nitrocellulose or PVDF membranes, and magnetic and other microbeads. While microdrops of protein delivered onto planar surfaces are the most familiar format, alternative architectures include CD centrifugation devices based on developments in microfluidics (Gyros, Monmouth Junction, NJ) and specialised chip designs, such as engineered microchannels in a plate (e.g., The Living Chip™, Biotrove, Woburn, MA) and tiny 3D posts on a silicon surface (Zyomyx, Hayward CA). Particles in suspension can also be used as the basis of arrays, providing they are coded for identification; systems include colour coding for microbeads (Luminex, Austin, TX; Bio-Rad Laboratories) and semiconductor nanocrystals (e.g., QDots™, Quantum Dot, Hayward, CA), and barcoding for beads (UltraPlex™, SmartBead Technologies Ltd, Babraham, Cambridge, UK) and multimetal microrods (e.g., Nanobarcodes™ particles, Nanoplex Technologies, Mountain View, CA). Beads can also be assembled into planar arrays on semiconductor chips (LEAPS technology, BioArray Solutions, Warren, NJ).

Immobilization of proteins involves both the coupling reagent and the nature of the surface being coupled to. A good protein array support surface is chemically stable before and after the coupling procedures, allows good spot morphology, displays minimal nonspecific binding, does not contribute a background in detection systems, and is compatible with different detection systems. The immobilization method used are reproducible, applicable to proteins of different properties (size, hydrophilic, hydrophobic), amenable to high throughput and automation, and compatible with retention of fully functional protein activity. Orientation of the surface-bound protein is recognized as an important factor in presenting it to ligand or substrate in an active state; for capture arrays the most efficient binding results are obtained with orientated capture reagents, which generally require site-specific labeling of the protein.

Both covalent and noncovalent methods of protein immobilization are used and have various pros and cons. Passive adsorption to surfaces is methodologically simple, but allows little quantitative or orientational control; it may or may not alter the functional properties of the protein, and reproducibility and efficiency are variable. Covalent coupling methods provide a stable linkage, can be applied to a range of proteins and have good reproducibility; however, orientation may be variable, chemical derivatization may alter the function of the protein and requires a stable interactive surface. Biological capture methods utilizing a tag on the protein provide a stable linkage and bind the protein specifically and in reproducible orientation, but the biological reagent must first be immobilized adequately and the array may require special handling and have variable stability.

Several immobilization chemistries and tags have been described for fabrication of protein arrays. Substrates for covalent attachment include glass slides coated with amino- or aldehyde-containing silane reagents. In the Versalinx™ system (Prolinx, Bothell, WA) reversible covalent coupling is achieved by interaction between the protein derivatised with phenyldiboronic acid, and salicylhydroxamic acid immobilized on the support surface. This also has low background binding and low intrinsic fluorescence and allows the immobilized proteins to retain function. Noncovalent binding of unmodified protein occurs within porous structures such as HydroGel™ (PerkinElmer, Wellesley, MA), based on a 3-dimensional polyacrylamide gel; this substrate is reported to give a particularly low background on glass microarrays, with a high capacity and retention of protein function. Widely used biological coupling methods are through biotin/streptavidin or hexahistidine/Ni interactions, having modified the protein appropriately. Biotin may be conjugated to a poly-lysine backbone immobilised on a surface such as titanium dioxide (Zyomyx) or tantalum pentoxide (Zeptosens, Witterswil, Switzerland).

Array fabrication methods include robotic contact printing, ink-jetting, piezoelectric spotting and photolithography. A number of commercial arrayers are available [e.g. Packard Biosciences] as well as manual equipment [V & P Scientific]. Bacterial colonies can be robotically gridded onto PVDF membranes for induction of protein expression in situ.

At the limit of spot size and density are nanoarrays, with spots on the nanometer spatial scale, enabling thousands of reactions to be performed on a single chip less than 1 mm square. BioForce Laboratories have developed nanoarrays with 1521 protein spots in 85 sq microns, equivalent to 25 million spots per sq cm, at the limit for optical detection; their readout methods are fluorescence and atomic force microscopy (AFM).

Fluorescence labeling and detection methods are widely used. The same instrumentation as used for reading DNA microarrays is applicable to protein arrays. For differential display, capture (e.g., antibody) arrays can be probed with fluorescently labeled proteins from two different cell states, in which cell lysates are directly conjugated with different fluorophores (e.g. Cy-3, Cy-5) and mixed, such that the color acts as a readout for changes in target abundance. Fluorescent readout sensitivity can be amplified 10-100 fold by tyramide signal amplification (TSA) (PerkinElmer Lifesciences). Planar waveguide technology (Zeptosens) enables ultrasensitive fluorescence detection, with the additional advantage of no intervening washing procedures. High sensitivity can also be achieved with suspension beads and particles, using phycoerythrin as label (Luminex) or the properties of semiconductor nanocrystals (Quantum Dot). A number of novel alternative readouts have been developed, especially in the commercial biotech arena. These include adaptations of surface plasmon resonance (HTS Biosystems, Intrinsic Bioprobes, Tempe, AZ), rolling circle DNA amplification (Molecular Staging, New Haven CT), mass spectrometry (Intrinsic Bioprobes; Ciphergen, Fremont, CA), resonance light scattering (Genicon Sciences, San Diego, CA) and atomic force microscopy [BioForce Laboratories].

Capture arrays form the basis of diagnostic chips and arrays for expression profiling. They employ high affinity capture reagents, such as conventional antibodies, single domains, engineered scaffolds, peptides or nucleic acid aptamers, to bind and detect specific target ligands in high throughput manner.

Antibody arrays have the required properties of specificity and acceptable background, and some are available commercially (BD Biosciences, San Jose, CA; Clontech, Mountain View, CA; BioRad; Sigma, St. Louis, MO). Antibodies for capture arrays are made either by conventional immunization (polyclonal sera and hybridomas), or as recombinant fragments, usually expressed in E. coli, after selection from phage or ribosome display libraries (Cambridge Antibody Technology, Cambridge, UK; BioInvent, Lund, Sweden; Affitech, Walnut Creek, CA; Biosite, San Diego, CA). In addition to the conventional antibodies, Fab and scFv fragments, single V-domains from camelids (VHH) or engineered human equivalents (Domantis, Waltham, MA) may also be useful in arrays.

The term "scaffold" refers to ligand-binding domains of proteins, which are engineered into multiple variants capable of binding diverse target molecules with antibody-like properties of specificity and affinity. The variants can be produced in a genetic library format and selected against individual targets by phage, bacterial or ribosome display. Such ligand-binding scaffolds or frameworks include 'Affibodies' based on *Staph. aureus* protein A (Affibody, Bromma, Sweden), 'Trinectins' based on fibronectins (Phylos, Lexington, MA) and 'Anticalins' based on the lipocalin structure (Pieris Proteolab, Freising-Weihenstephan, Germany). These can be used on capture arrays in a similar fashion to antibodies and may have advantages of robustness and ease of production.

Nonprotein capture molecules, notably the single-stranded nucleic acid aptamers which bind protein ligands with high specificity and affinity, are also used in arrays (SomaLogic, Boulder, CO). Aptamers are selected from libraries of oligonucleotides by the Selex™ procedure and their interaction with protein can be enhanced by covalent attachment, through incorporation of brominated deoxyuridine and UV-activated crosslinking (photoaptamers). Photocrosslinking to ligand reduces the crossreactivity of aptamers due to the specific steric requirements. Aptamers have the advantages of ease of production by automated oligonucleotide synthesis and the stability and robustness of DNA; on photoaptamer arrays, universal fluorescent protein stains can be used to detect binding.

Protein analytes binding to antibody arrays may be detected directly or via a secondary antibody in a sandwich assay. Direct labelling is used for comparison of different samples with different colours. Where pairs of antibodies directed at the same protein ligand are available, sandwich immunoassays provide high specificity and sensitivity and are therefore the method of choice for low abundance proteins such as cytokines; they also give the possibility of detection of protein modifications. Label-free detection methods, including mass spectrometry, surface plasmon resonance and atomic force microscopy, avoid alteration of ligand. What is required from any method is optimal sensitivity and specificity, with low background to give high signal to noise. Since analyte concentrations cover a wide range, sensitivity has to be tailored appropriately; serial dilution of the sample or use of antibodies of different affinities are solutions to this problem. Proteins of interest are frequently those in low concentration in body fluids and extracts, requiring detection in the pg range or lower, such as cytokines or the low expression products in cells.

An alternative to an array of capture molecules is one made through 'molecular imprinting' technology, in which peptides (e.g., from the C-terminal regions of proteins) are used as templates to generate structurally complementary, sequence-specific cavities in a polymerizable matrix; the cavities can then specifically capture (denatured) proteins that have the appropriate primary amino acid sequence (ProteinPrint™, Aspira Biosystems, Burlingame, CA).

Another methodology which can be used diagnostically and in expression profiling is the ProteinChip® array (Ciphergen, Fremont, CA), in which solid phase chromatographic surfaces bind proteins with similar characteristics of charge or hydrophobicity from mixtures such as plasma or tumour extracts, and SELDI-TOF mass spectrometry is used to detection the retained proteins.

Large-scale functional chips have been constructed by immobilizing large numbers of purified proteins and used to assay a wide range of biochemical functions, such as protein interactions with other proteins, drug-target interactions, enzyme-substrates, etc. Generally they require an expression library, cloned into *E. coli*, yeast or similar from which the expressed proteins are then purified, e.g. via a His tag, and immobilized. Cell free protein transcription/translation is a viable alternative for synthesis of proteins which do not express well in bacterial or other in vivo systems.

For detecting protein-protein interactions, protein arrays can be in vitro alternatives to the cell-based yeast two-hybrid system and may be useful where the latter is deficient, such as interactions involving secreted proteins or proteins with disulphide bridges. High-throughput analysis of biochemical activities on arrays has been described for yeast protein kinases and for various functions (protein-protein and protein-lipid interactions) of the yeast proteome, where a large proportion of all yeast open-reading frames was expressed and immobilised on a microarray. Large-scale 'proteome chips' promise to be very useful in identification of functional interactions, drug screening, etc. (Proteometrix, Branford, CT).

As a two-dimensional display of individual elements, a protein array can be used to screen phage or ribosome display libraries, in order to select specific binding partners, including antibodies, synthetic scaffolds, peptides and aptamers. In this way, 'library against library' screening can be carried out. Screening of drug candidates in combinatorial chemical libraries against an array of protein targets identified from genome projects is another application of the approach.

A multiplexed bead assay, such as, for example, the BD™ Cytometric Bead Array, is a series of spectrally discrete particles that can be used to capture and quantitate soluble analytes. The analyte is then measured by detection of a fluorescence-based emission and flow cytometric analysis. Multiplexed bead assay generates data that is comparable to ELISA based assays, but in a "multiplexed" or simultaneous fashion. Concentration of unknowns is calculated for the cytometric bead array as with any sandwich format assay, i.e. through the use of known standards and plotting unknowns against a standard curve. Further, multiplexed bead assay allows quantification of soluble analytes in samples never previously considered due to sample volume limitations. In addition to the quantitative data, powerful visual images can be generated revealing unique profiles or signatures that provide the user with additional information at a glance.

6. Pharmaceutical Carriers/Delivery of Pharmaceutical Products

As described above, the compositions can also be administered in vivo in a pharmaceutically acceptable carrier. By "pharmaceutically acceptable" is meant a material that is not biologically or otherwise undesirable, i.e., the material may be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

The compositions may be administered orally, parenterally (e.g., intravenously), by intramuscular injection, by intraperitoneal injection, transdermally, extracorporeally, topically or the like, including topical intranasal administration or administration by inhalant. As used herein, "topical intranasal administration" means delivery of the compositions into the nose and nasal passages through one or both of the nares and can comprise delivery by a spraying mechanism or droplet mechanism, or through aerosolization of the nucleic acid or vector. Administration of the compositions by inhalant can be through the nose or mouth via delivery by a spraying or droplet mechanism. Delivery can also be directly to any area of the respiratory system (e.g., lungs) via intubation. The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein.

The materials may be in solution, suspension (for example, incorporated into microparticles, liposomes, or cells). These may be targeted to a particular cell type via antibodies, receptors, or receptor ligands. The following references are examples of the use of this technology to target specific proteins to tumor tissue (Senter, et al., *Bioconjugate Chem.*, 2:447-451, (1991); Bagshawe, K. D., *Br. J. Cancer*, 60:275-281, (1989); Bagshawe, et al., *Br. J. Cancer*, 58:700-703, (1988); Senter, et al., *Bioconjugate Chem.*, 4:3-9, (1993); Battelli, et al., *Cancer Immunol. Immunother.*, 35:421-425, (1992); Pietersz and McKenzie, *Immunolog. Reviews*, 129:57-80, (1992); and Roffler, et al., *Biochem. Pharmacol*, 42:2062-2065, (1991)). Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., *Cancer Research*, 49:6214-6220, (1989); and Litzinger and Huang, *Biochimica et Biophysica Acta*, 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, *DNA and Cell Biology* 10:6, 399-409 (1991)).

a) Pharmaceutically Acceptable Carriers

The compositions, including antibodies, can be used therapeutically in combination with a pharmaceutically acceptable carrier.

Suitable carriers and their formulations are described in Remington: *The Science and Practice of Pharmacy* (19th ed.) ed. A. R. Gennaro, Mack Publishing Company, Easton, PA Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of composition being administered.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions may include carriers, thickeners, diluents, buffers, preservatives, surface active agents and the like in addition to the molecule of choice. Pharmaceutical compositions may also include one or more active ingredients such as antimicrobial agents, antiinflammatory agents, anesthetics, and the like.

The pharmaceutical composition may be administered in a number of ways depending on whether local or systemic treatment is desired, and on the area to be treated. Administration may be topically (including ophthalmically, vaginally, rectally, intranasally), orally, by inhalation, or parenterally, for example by intravenous drip, subcutaneous, intraperitoneal or intramuscular injection. The disclosed antibodies can be administered intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions can be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

b) Therapeutic Uses

Effective dosages and schedules for administering the compositions may be determined empirically, and making such determinations is within the skill in the art. The dosage ranges for the administration of the compositions are those large enough to produce the desired effect in which the symptoms of the disorder are effected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any counterindications. Dosage can vary, and can be administered in one or more dose administrations daily, for one or several days. Guidance can be found in the literature for appropriate dosages for given classes of pharmaceutical products. For example, guidance in selecting appropriate doses for antibodies can be found in the literature on therapeutic uses of antibodies, e.g., *Handbook of Monoclonal Antibodies*, Ferrone et al., eds., Noges Publications, Park Ridge, NJ, (1985) ch. 22 and pp. 303-357; Smith et al., *Antibodies in Human Diagnosis and Therapy*, Haber et al., eds., Raven Press, New York (1977) pp. 365-389. A typical daily dosage of the antibody used alone might range from about 1 μg/kg to up to 100 mg/kg of body weight or more per day, depending on the factors mentioned above.

C. Method of Enhancing Immune Responses, Immunotherapies, and Treating Cancer

It is understood and herein contemplated that DAP12 can enhance immune responses by promoting activation and/or inducing maturation of dendritic cells and/or inducing SYK activation in dendritic cells (such as, for example, monocyte derived dendritic cells (Mo-DC)) including but not limited to autologous derived dendritic cells or dendritic cells from an allogeneic source. Thus, in one aspect, disclosed herein are methods of promoting activation of dendritic cells, inducing maturation of dendritic cells, and/or inducing SYK activation in dendritic cells (including, but not limited to Mo-DC) comprising contacting a dendritic cell with any of the modified DAP12 or vectors disclosed herein. As noted herein, by promoting activation and/or maturation of dendritic cells and/or inducing SYK activation, cytokines are released that enhance T cell activation and/or proliferation. Accordingly, in one aspect, disclosed herein are methods of activating T cells and/or stimulating the proliferation of T cells comprising contacting the T cells with any of the modified DAP12, vectors, or dendritic cells disclosed herein. In one aspect the modified DAP12 can be transfected into dendritic cell ex vivo and the T cells can be contacted with the dendritic cell comprising the modified DAP12.

It is understood and herein contemplated that by enhancing endogenous immune responses, the immune system subject with a cancer is more capable of recognizing and mounting an immune response to the cancer. In one aspect disclosed herein are methods of treating, decreasing, reducing, inhibiting, ameliorating and/or preventing a cancer and/or metastasis in a subject comprising administering to the subject any of the modified DAP12, vectors, or dendritic cells disclosed herein. For example, disclosed herein are methods of treating, decreasing, reducing, inhibiting, ameliorating and/or preventing a cancer and/or metastasis in a subject comprising administering to the subject a modified DAP12 comprising one or more substitutions in the cytoplasmic domain of DAP12 (such as, for example a substitution at a residue corresponding to residues 91, 99, 100, 101, 102, 104, 105, 106, 111, or 112 of DAP12, including, but not limited to a D100V substitution; a Y91E substitution; a S99H substitution; a D100H substitution; a Y102C substitution; a Y102E substitution; a Y102D substitution; a V101R substitution; a D104H substitution; a Y111E substitution; a Y111D substitution; a Y112D substitution; a Y112E substitution; a Y91D substitution; a D104N substitution; a Y91C substitution; a L105Y substitution; and/or a N106K substitution and/or any combination thereof, including, but not limited to a Y91E, Y102E, and Y112E substitution; a Y91E, Y102E, Y111E, and Y112E substitution; a Y91D and Y102D substitution; a D100V and V101R substitution; or a S99H and a D104H substitution); a vector (such as, for example an adenoviral vector) comprising any of the modified DAP12 disclosed herein; or a dendritic cells comprising any of the modified DAP12 or vectors disclosed herein. In one aspect, the method can further comprise administering to the subject a dendritic cell (such as, for example, an autologous dendritic cell or a dendritic cell from an allogenic source), including, but not limited to a dendritic cell comprising a modified DAP12 (for example, a dendritic cell that has been transfected with the modified DAP12 or a vector encoding said modified DAP12) ex vivo.

The disclosed compositions can be used to treat any disease where uncontrolled cellular proliferation occurs such as cancers. A representative but non-limiting list of cancers that the disclosed compositions can be used to treat is the following: lymphoma, B cell lymphoma, T cell lymphoma, mycosis fungoides, Hodgkin's Disease, myeloid leukemia, bladder cancer, brain cancer, nervous system cancer, head and neck cancer, squamous cell carcinoma of head and neck, lung cancers such as small cell lung cancer and non-small cell lung cancer, neuroblastoma/glioblastoma, ovarian cancer, skin cancer, liver cancer, melanoma, squamous cell carcinomas of the mouth, throat, larynx, and lung, cervical cancer, cervical carcinoma, breast cancer, and epithelial cancer, renal cancer, genitourinary cancer, pulmonary cancer, esophageal carcinoma, head and neck carcinoma, large bowel cancer, hematopoietic cancers; testicular cancer; colon cancer, rectal cancer, prostatic cancer, or pancreatic cancer.

In one aspect, it is understood the treatment of cancer does not need to be limited to the administration of modified DAP12, vectors comprising a modified DAP12, or dendritic cells comprising said modified DAP12 or vectors, but can include the further administration of anti-cancer agents to treat, inhibit, reduce, decrease, ameliorate, and/or prevent a cancer or metastasis. Anti-cancer therapeutic agents (such as chemotherapeutics, immunotoxins, peptides, and antibodies) that can be used in the methods of treating, inhibiting, reducing, decreasing, ameliorating, and/or preventing a cancer and/or metastasis and in combination with any of the disclosed neoantigens or any CAR T cells, TIL, or MIL specific for said neoantigen can comprise any anti-cancer therapeutic agent known in the art, the including, but not limited to Abemaciclib, Abiraterone Acetate, ABITREXATE® (Methotrexate), ABRAXANE® (Paclitaxel Albumin-stabilized Nanoparticle Formulation), ABVD, ABVE, ABVE-PC, AC, AC-T, ADCETRIS® (Brentuximab Vedotin), ADE, Ado-Trastuzumab Emtansine, ADRIAMYCIN® (Doxorubicin Hydrochloride), Afatinib Dimaleate, AFINITOR® (Everolimus), AKYNZEO® (Netupitant and Palonosetron Hydrochloride), ALDARA® (Imiquimod), Aldesleukin, ALECENSA® (Alectinib), Alectinib, Alemtuzumab, ALIMTA® (Pemetrexed Disodium), ALIQOPA® (Copanlisib Hydrochloride), ALKERAN™ for Injection (Melphalan Hydrochloride), ALKERAN™ Tablets (Melphalan), Alexi ALOXI® (Palonosetron Hydrochloride), ALUNBRIG® (Brigatinib), AMBOCHLORIN® (Chlorambucil), AMBOCLORIN® (Chlorambucil), Amifostine, Aminolevulinic Acid, Anastrozole, Aprepitant, AREDIA® (Pamidronate Disodium), ARIMIDEX® (Anastrozole), AROMASIN® (Exemestane), ARRANON® (Nelarabine), Arsenic Trioxide, ARZERRA® (Ofatumumab), Asparaginase *Erwinia chrysanthemi*, Atezolizumab, AVASTIN® (Bevacizumab), Avelumab, Axitinib, Azacitidine, BAVENCIO® (Avelumab), BEACOPP, BECENUM® (Carmustine), BELEODAQ® (Belinostat), Belinostat, Bendamustine Hydrochloride, BEP, BESPONSA® (Inotuzumab Ozogamicin), Bevacizumab, Bexarotene, Bexxar BEXXAR® (Tositumomab and Iodine I 131 Tositumomab), Bicalutamide, BICNU® (Carmustine), Bleomycin, Blinatumomab, BLINCYTO® (Blinatumomab), Bortezomib, BOSULIF® (Bosutinib), Bosutinib, Brentuximab Vedotin, Brigatinib, BuMel, Busulfan, BUSULFEX® (Busulfan), Cabazitaxel, CABOMETYX® (Cabozantinib-S-Malate), Cabozantinib-S-Malate, CAF, CAMPATH® (Alemtuzumab), CAMPTOSAR® (Irinotecan Hydrochloride), Capecitabine, CAPOX, CARAC® (Fluorouracil—Topical), Carboplatin, CARBOPLATIN-TAXOL, Carfilzomib, CARMUBRIS® (Carmustine), Carmustine, Carmustine Implant, CASODEX® (Bicalutamide), CEM, Ceritinib, CERUBIDINE® (Daunorubicin Hydrochloride), CERVARIX® (Recombinant HPV Bivalent Vaccine), Cetuximab, CEV, Chlorambucil, CHLORAMBUCIL-PREDNISONE, CHOP, Cisplatin, Cladribine, CLAFEN® (Cyclophosphamide), Clofarabine, CLOFAREX® (Clofarabine), CLOLAR® (Clofarabine), CMF, Cobimetinib, COMETRIQ® (Cabozantinib-S-Malate), Copanlisib Hydrochloride, COPDAC, COPP, COPP-ABV, Cosmegen COSMEGEN® (Dactinomycin), COTELLIC® (Cobimetinib), Crizotinib, CVP, Cyclophosphamide, CYFOS® (Ifosfamide), CYRAMZA® (Ramucirumab), Cytarabine, Cytarabine Liposome, U CYTOSAR-UR (Cytarabine), CYTOXAN® (Cyclophosphamide), Dabrafenib, Dacarbazine, DACOGEN® (Decitabine), Dactinomycin, Daratumumab, DARZALEX® (Daratumumab), Dasatinib, Daunorubicin Hydrochloride, Daunorubicin Hydrochloride and Cytarabine Liposome, Decitabine, Defibrotide Sodium, DEFITELIO® (Defibrotide Sodium), Degarelix, Denileukin Diftitox, Denosumab, DEPOCYT® (Cytarabine Liposome), Dexamethasone, Dexrazoxane Hydrochloride, Dinutuximab, Docetaxel, DOXIL® (Doxorubicin Hydrochloride Liposome), Doxorubicin Hydrochloride, Doxorubicin Hydrochloride Liposome, DOX-SL® (Doxorubicin Hydrochloride Liposome), DTIC-DOME® (Dacarbazine), Durvalumab, EFUDEX® (Fluorouracil—Topical), ELITEK® (Rasburicase), ELLENCE® (Epirubicin Hydrochloride), Elotuzumab, ELOXATIN® (Oxaliplatin), Eltrombopag Olamine, EMEND® (Aprepitant), EMPLICITI® (Elotuzumab), Enasidenib Mesylate, Enzalutamide, Epirubicin Hydrochloride, EPOCH, ERBITUX® (Cetuximab), Eribulin Mesylate, ERIVEDGE® (Vismodegib), Erlotinib Hydrochloride, ERWINAZE® (Asparaginase *Erwinia chrysanthemi*), ETHYOL® (Amifostine), Etopophos ETOPOPHOS® (Etoposide Phosphate), Etoposide, Etoposide Phosphate, EVACET® (Doxorubicin Hydrochloride Liposome), Everolimus, EVISTA® (Raloxifene Hydrochloride), EVOMELA® (Melphalan Hydrochloride), Exemestane, 5-FU® (Fluorouracil Injection), 5-FU® (Fluorouracil—Topical), FARESTON® (Toremifene), FARYDAK® (Panobinostat), FASLODEX® (Fulvestrant), FEC, FEMARA® (Letrozole), Filgrastim, FLUDARA® (Fludarabine Phosphate), Fludarabine Phosphate, FLUOROPLEX® (Fluorouracil—Topical), Fluorouracil Injection, Fluorouracil—Topical, Flutamide, FOLEX® (Methotrexate), FOLEX PFS® (Methotrexate), FOLFIRI, FOLFIRI-BEVACIZUMAB, FOLFIRI-CETUXIMAB, FOLFIRINOX, FOLFOX, FOLOTYN® (Pralatrexate), FU-LV, Fulvestrant, Gardasil GARDASIL® (Recombinant HPV Quadrivalent Vaccine), GARDASIL 9® (Recombinant HPV Nonavalent Vaccine), GAZYVA® (Obinutuzumab), Gefitinib, Gemcitabine Hydrochloride, GEMCITABINE-CISPLATIN, GEMCITABINE-OXALIPLATIN, Gemtuzumab Ozogamicin, GEMZAR® (Gemcitabine Hydrochloride), GILOTRIF® (Afatinib Dimaleate), GLEEVEC® (Imatinib Mesylate), GLIADEL® (Carmustine Implant), GLIADEL WAFER® (Carmustine Implant), Glucarpidase, Goserelin Acetate, HALAVEN® (Eribulin Mesylate), HEMANGEOL® (Propranolol Hydrochloride), HERCEPTIN® (Trastuzumab), HPV Bivalent Vaccine, Recombinant, HPV Nonavalent Vaccine, Recombinant, HPV Quadrivalent Vaccine, Recombinant, HYCAMTIN® (Topotecan Hydrochloride), HYDREA® (Hydroxyurea), Hydroxyurea, Hyper-CVAD, IBRANCE® (Palbociclib), Ibritumomab Tiuxetan, Ibrutinib, ICE, ICLUSIG® (Ponatinib Hydrochloride), IDAMYCIN® (Idarubicin Hydrochloride), Idarubicin Hydrochloride, Idelalisib, IDHIFA® (Enasidenib Mesylate), IFEX® (Ifosfamide), Ifosfamide, IFOSFAMIDUM® (Ifosfamide), IL-2 (Aldesleukin), Imatinib Mesylate, IMBRUVICA® (Ibrutinib), IMFINZI® (Durvalumab), Imiquimod, IMLYGIC® (Talimogene Laherparepvec), INLYTA® (Axitinib), Inotuzumab Ozogamicin, Interferon Alfa-2b, Recombinant, Interleukin-2 (Aldesleukin), INTRON A® (Recombinant Interferon Alfa-2b), Iodine I 131 Tositumomab and Tositumomab, Ipilimumab, IRESSA® (Gefitinib), Irinotecan Hydrochloride, Irinotecan Hydrochloride Liposome, ISTODAX® (Romidepsin), Ixabepilone, Ixazomib Citrate, IXEMPRA® (Ixabepilone), JAKAFI® (Ruxolitinib Phosphate), JEB, JEVTANA® (Cabazitaxel), KADCYLA® (Ado-Trastuzumab Emtansine), KEOXIFENE® (Raloxifene Hydrochloride), KEPIVANCE® (Palifermin), KEYTRUDA® (Pembrolizumab), KISQALI® (Ribociclib), KYMRIAH® (Tisagenlecleucel), KYPROLIS® (Carfilzomib), Lanreotide Acetate, Lapatinib Ditosylate, LARTRUVO® (Olaratumab), Lenalidomide, Lenvatinib Mesylate, LENVIMA® (Lenvatinib Mesylate), Letrozole, Leucovorin Calcium, LEUKERAN® (Chlorambucil), Leuprolide Acetate, LEUSTATIN® (Cladribine), LEVULAN® (Aminolevulinic Acid), LINFOLIZIN® (Chlorambucil), LIPODOX® (Doxorubicin Hydrochloride Liposome), Lomustine, LONSURF® (Trifluridine and Tipiracil Hydrochloride), LUPRON® (Leuprolide Acetate), LUPRON DEPOT® (Leuprolide Acetate), LUPRON DEPOT-PED® (Leuprolide Acetate), LYNPARZA® (Olaparib), MARQIBO® (Vincristine Sulfate Liposome), MATULANE® (Procarbazine Hydrochloride), Mechlorethamine Hydrochloride, Megestrol Acetate, MEKINIST® (Trametinib), Melphalan, Melphalan Hydrochloride, Mercaptopurine, Mesna, MESNEX® (Mesna), METHAZOLASTONE® (Temozolomide), Methotrexate, METHOTREXATE LPF® (Methotrexate), Methylnaltrexone Bromide, MEXATE®

(Methotrexate), MEXATE-AQ® (Methotrexate), Midostaurin, Mitomycin C, Mitoxantrone Hydrochloride, MITOZYTREX® (Mitomycin C), MOPP, MOZOBIL® (Plerixafor), MUSTARGEN® (Mechlorethamine Hydrochloride), MUTAMYCIN® (Mitomycin C), MYLERAN® (Busulfan), MYLOSAR® (Azacitidine), MYLOTARG® (Gemtuzumab Ozogamicin), NANOPARTICLE PACLITAXEL® (Paclitaxel Albumin-stabilized Nanoparticle Formulation), NAVELBINE® (Vinorelbine Tartrate), Necitumumab, Nelarabine, NEOSAR® (Cyclophosphamide), Neratinib Maleate, NERLYNX® (Neratinib Maleate), Netupitant and Palonosetron Hydrochloride, NEULASTA® (Pegfilgrastim), NEUPOGEN® (Filgrastim), Nexavar NEXAVAR® (Sorafenib Tosylate), NILANDRON® (Nilutamide), Nilotinib, Nilutamide, NINLARO® (Ixazomib Citrate), Niraparib Tosylate Monohydrate, Nivolumab, NOLVADEX® (Tamoxifen Citrate), NPLATE® (Romiplostim), Obinutuzumab, ODOMZO® (Sonidegib), OEPA, Ofatumumab, OFF, Olaparib, Olaratumab, Omacetaxine Mepesuccinate, ONCASPAR® (Pegaspargase), Ondansetron Hydrochloride, ONIVYDE® (Irinotecan Hydrochloride Liposome), Ontak ONTAK® (Denileukin Diftitox), OPDIVO® (Nivolumab), OPPA, Osimertinib, Oxaliplatin, Paclitaxel, Paclitaxel Albumin-stabilized Nanoparticle Formulation, PAD, Palbociclib, Palifermin, Palonosetron Hydrochloride, Palonosetron Hydrochloride and Netupitant, Pamidronate Disodium, Panitumumab, Panobinostat, PARAPLAT® (Carboplatin), PARAPLATIN® (Carboplatin), Pazopanib Hydrochloride, PCV, PEB, Pegaspargase, Pegfilgrastim, Peginterferon Alfa-2b, PEG-INTRON® (Peginterferon Alfa-2b), Pembrolizumab, Pemetrexed Disodium, PERJETA® (Pertuzumab), Pertuzumab, PLATINOL® (Cisplatin), PLATINOL-AQ® (Cisplatin), Plerixafor, Pomalidomide, POMALYST® (Pomalidomide), Ponatinib Hydrochloride, PORTRAZZA® (Necitumumab), Pralatrexate, Prednisone, Procarbazine Hydrochloride, PROLEUKIN® (Aldesleukin), PROLIA® (Denosumab), PROMACTA® (Eltrombopag Olamine), Propranolol Hydrochloride, PROVENGE® (Sipuleucel-T), Purinethel PURINETHOL® (Mercaptopurine), PURIXAN® (Mercaptopurine), Radium 223 Dichloride, Raloxifene Hydrochloride, Ramucirumab, Rasburicase, R-CHOP, R-CVP, Recombinant Human Papillomavirus (HPV) Bivalent Vaccine, Recombinant Human Papillomavirus (HPV) Nonavalent Vaccine, Recombinant Human Papillomavirus (HPV) Quadrivalent Vaccine, Recombinant Interferon Alfa-2b, Regorafenib, RELISTOR® (Methylnaltrexone Bromide), R-EPOCH, REVLIMID® (Lenalidomide), RHEUMATREX® (Methotrexate), Ribociclib, R-ICE, RITUXAN® (Rituximab), RITUXAN HYCELA® (Rituximab and Hyaluronidase Human), Rituximab, Rituximab and, Hyaluronidase Human, Rolapitant Hydrochloride, Romidepsin, Romiplostim, RUBIDOMYCIN® (Daunorubicin Hydrochloride), RUBRACA® (Rucaparib Camsylate), Rucaparib Camsylate, Ruxolitinib Phosphate, RYDAPT® (Midostaurin), Sclerosol Intrapleural Aerosol (Talc), Siltuximab, Sipuleucel-T, SOMATULINE DEPOT® (Lanreotide Acetate), Sonidegib, Sorafenib Tosylate, SPRYCEL® (Dasatinib), STANFORD V, Sterile Talc Powder (Talc), STERITALC® (Talc), STIVARGA® (Regorafenib), Sunitinib Malate, SUTENT® (Sunitinib Malate), SYLATRON® (Peginterferon Alfa-2b), SYLVANT® (Siltuximab), Synribo SYNRIBO® (Omacetaxine Mepesuccinate), TABLOID® (Thioguanine), TAC, TAFINLAR® (Dabrafenib), TAGRISSO® (Osimertinib), Talc, Talimogene Laherparepvec, Tamoxifen Citrate, TARABINE PFS® (Cytarabine), TARCEVA® (Erlotinib Hydrochloride), TARGRETIN® (Bexarotene), TASIGNA® (Nilotinib), TAXOL® (Paclitaxel), TAXOTERE® (Docetaxel), TECENTRIQ® (Atezolizumab), TEMODAR® (Temozolomide), Temozolomide, Temsirolimus, Thalidomide, THALOMID® (Thalidomide), Thioguanine, Thiotepa, Tisagenlecleucel, TOLAK® (Fluorouracil—Topical), Topotecan Hydrochloride, Toremifene, TORISEL® (Temsirolimus), Tositumomab and Iodine I 131 Tositumomab, TOTECT® (Dexrazoxane Hydrochloride), TPF, Trabectedin, Trametinib, Trastuzumab, TREANDA® (Bendamustine Hydrochloride), Trifluridine and Tipiracil Hydrochloride, TRISENOX® (Arsenic Trioxide), TYKERB® (Lapatinib Ditosylate), UNITUXIN® (Dinutuximab), Uridine Triacetate, VAC, Vandetanib, VAMP, VARUBI® (Rolapitant Hydrochloride), VECTIBIX® (Panitumumab), VeIP, VELBAN® (Vinblastine Sulfate), VELCADE® (Bortezomib), VELSAR® (Vinblastine Sulfate), Vemurafenib, VENCLEXTA® (Venetoclax), Venetoclax, VERZENIO® (Abemaciclib), VIADUR® (Leuprolide Acetate), VIDAZA® (Azacitidine), Vinblastine Sulfate, VINCASAR PFS® (Vincristine Sulfate), Vincristine Sulfate, Vincristine Sulfate Liposome, Vinorelbine Tartrate, VIP, Vismodegib, VISTOGARD® (Uridine Triacetate), VORAXAZE® (Glucarpidase), Vorinostat, VOTRIENT® (Pazopanib Hydrochloride), VYXEOS® (Daunorubicin Hydrochloride and Cytarabine Liposome), WELLCOVORIN® (Leucovorin Calcium), XALKORI® (Crizotinib), XELODA® (Capecitabine), XELIRI, XELOX, XGEVA® (Denosumab), XOFIGO® (Radium 223 Dichloride), XTANDI® (Enzalutamide), YERVOY® (Ipilimumab), YONDELIS® (Trabectedin), ZALTRAP® (Ziv-Aflibercept), ZARXIO® (Filgrastim), ZEJULA® (Niraparib Tosylate Monohydrate), ZELBORAF® (Vemurafenib), ZEVALIN® (Ibritumomab Tiuxetan), ZINECARD® (Dexrazoxane Hydrochloride), Ziv-Aflibercept, ZOFRAN® (Ondansetron Hydrochloride), ZOLADEX® (Goserelin Acetate), Zoledronic Acid, ZOLINZA® (Vorinostat), ZOMETA® (Zoledronic Acid), ZYDELIG® (Idelalisib), ZYKADIA® (Ceritinib), and/or ZYTIGA® (Abiraterone Acetate). Checkpoint inhibitors include, but are not limited to antibodies that block PD-1 (Nivolumab (BMS-936558 or MDX1106), CT-011, MK-3475), PD-L1 (MDX-1105 (BMS-936559), MPDL3280A, MSB0010718C), PD-L2 (rHIgM12B7), CTLA-4 (Ipilimumab (MDX-010), Tremelimumab (CP-675,206)), IDO, B7-H3 (MGA271), B7-H4, TIM3, LAG-3 (BMS-986016).

It is understood and herein contemplated that where the methods treating, decreasing, reducing, inhibiting, ameliorating and/or preventing a cancer and/or metastasis comprise the use of an anti-cancer immunotherapy, the immunotherapy can be administered simultaneously with, concurrently with, or following administration of the modified DAP12, vectors comprising a modified DAP12, or dendritic cells comprising said modified DAP12 or vectors. Thus, also disclosed herein are methods of treating, decreasing, reducing, inhibiting, ameliorating and/or preventing a cancer and/or metastasis, further comprising administering to a subject an anti-cancer immunotherapy. In one aspect, disclosed herein are methods of treating, decreasing, reducing, inhibiting, ameliorating and/or preventing a cancer and/or metastasis wherein the anti-cancer immunotherapy is administered to the subject at least 5, 10, 15, 20, 25, 30, 35, 40, 45, 50, 55, 60, 65, 70, 75, 80, 85, 90 minutes, 2, 3, 4, 5, 6, 7, 8, 9, 10, 11, 12, 13, 14, 15, 16, 17, 18, 19, 20, 21, 22, 23, 24, 25, 26, 27, 28, 29, 30, 32, 35, 36, 40, 42, 45, 48 hours, 3, 4, 5, 6, 7, 8, 9, 10, 11, 12, 13, 14, 15, 16, 17, 18, 19, 20, 21, 22, 23, 24, 25, 26, 27, 28, 29, 30, 31, 45, 58, 59, 60, 61 days, 3, 4, 5, 6, 7, 8, 9, 10, 11, 12 months following administration of the modified DAP12.

It is further understood and herein contemplated that by promoting activation and/or inducing maturation of dendritic cells and/or inducing SYK activation in dendritic cells or by activating T cells and/or stimulating the proliferation of T cells, the disclosed modified DAP12, vectors comprising a modified DAP12, or dendritic cells comprising said modified DAP12 or vectors enhance the efficacy of an anti-cancer immunotherapy. Thus, in one aspect, disclosed herein are methods of enhancing an anti-cancer immunotherapy in a subject comprising administering to the subject the modified DAP12, vector, or dendritic cell of any preceding aspect at least 5, 10, 15, 20, 25, 30, 35, 40, 45, 50, 55, 60, 65, 70, 75, 80, 85, 90 minutes, 2, 3, 4, 5, 6, 7, 8, 9, 10, 11, 12, 13, 14, 15, 16, 17, 18, 19, 20, 21, 22, 23, 24, 25, 26, 27, 28, 29, 30, 32, 35, 36, 40, 42, 45, 48 hours, 3, 4, 5, 6, 7, 8, 9, 10, 11, 12, 13, 14, 15, 16, 17, 18, 19, 20, 21, 22, 23, 24, 25, 26, 27, 28, 29, 30, 31, 45, 58, 59, 60, 61 days, 3, 4, 5, 6, 7, 8, 9, 10, 11, 12 months prior to administration of the anti-cancer immunotherapy.

D. EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

1. Example 1: Constitutively Activated DAP12 Induces Functional Anti-Tumor Activation and Maturation of Human Monocyte-Derived DC a) Results (1) Constitutively Active DAP12-Mutants Induce Syk Activation in Human Mo-DC We have generated a series of twelve DAP12 mutants within the ITAM domain with the purpose of understanding its function in the maturation of myeloid cells. The chosen sites are conserved amino acid residues within the ITAM domain which are essential for signal propagation. Among the changes are the modification of the tyrosines at positions 91, 102, 111 or 112 into either glutamate or aspartate to mimic phosphorylation. Conversely, 91 or 102 were converted to a cysteine to block activation. We also changed aspartate at position 100 into valine or histidine which are basic amino acids that allow normal binding but with rapid dissociation, and valine at position 101 into arginine to disrupt the ITAM interaction with a positive charge (FIG. 1a). The control dominant negative (dn) form of DAP12 is a mutation in the second tyrosine into an alanine shown to not stimulate SYK activation.

In order to determine the activity of each mutant DAP12 clone we assessed the activation of Syk, a main signaling molecule recruited by DAP12 through its ITAM domain. For this purpose, overexpressed Syk was immunoprecipitated (IP) from AD293 cells after co-transfection with each of the DAP12 mutants followed by western blot with a pan-phospho-tyrosine antibody (clone 4G10). As a positive control for Syk activation, antibodies to TREM1 were used to cross-link this receptor and induce signaling, bringing Syk and DAP12 in proximity for activation. Of the tested DAP12 mutants, P17, P19 and P23 were able to induce tyrosine phosphorylation of Syk, demonstrating their activation state (FIG. 1b). We selected P19 and P23 to continue as p17, as described earlier, is meant to rapidly dissociate and therefore not constitutively activated. Immunoprecipitation of DAP12 (FIG. 1c bottom panel) in these cells revealed higher levels of activation with the P19 and the P23 mutants, compared to WT DAP12, concomitant with Syk activation (FIG. 1c, top panel). This observation is consistent with findings in myeloid derived suppressor cells. We then investigated if P19 and P23, physically associates with Syk by co-immunoprecipitating over-expressed DAP12 and Syk. As expected, these activated forms of DAP12 were able to associate with Syk (FIG. 1d). Syk, and its downstream pathway, is a novel target for the induction of DC maturation since it is required for: the internalization of immune complexes, antigen presentation to T lymphocytes, and IL-12 production after FcRγ engagement. To further characterize if these constructs can induce a functional role in DCs, we expressed the mutant DAP12 constructs in human primary Mo-DCs via an adenoviral vector. Mo-DCs were generated from the peripheral blood of healthy human donors and culturing in GM-CSF and IL-4 followed by transduction with either the WT DAP12, P19, or P23 adenoviral constructs. Flow cytometric analysis of transfected Mo-DC showed that the transduction rates were above 70% as assessed by GFP positivity (FIG. 2) and that phospho-Syk levels were higher in Mo-DC expressing either Ad-P19 or Ad-P23, compared with WT DAP12 (FIG. 1e). These results indicate that the P19 and P23 DAP12 mutants have the ability to initiate the downstream signal without involvement of a surface activating receptor.

(2) Constitutively Active DAP12 Induces Phenotypical Maturation and Activation of Mo-DC To determine whether the DAP12 mutants stimulated phenotypic changes associated with DC maturation, flow cytometric analyses were performed on primary Mo-DC from three independent human donors to determine the expression levels of CD83, a specific surface marker of mature DCs, and the co-stimulatory molecules CD40, CD80, and CD86. We observed an up-regulation of CD80 and CD83 in Mo-DC transduced with Ad-P19 or Ad-P23 compared to those transduced with WT DAP12 vector (FIG. 3a and Table 3). However, we did not detect changes in the expression of the co-stimulatory molecules CD40 and CD86 with any of the DAP12 constructs. Other hallmarks of DC activation, such as the chemokine receptor CCR7, were also upregulated by both Ad-P19 and Ad-P23. In order to understand if the increase in co-stimulatory protein expression is due to earlier up-regulation of maturation markers by constitutively active DAP12, we also assess expression 24 hours after transduction (FIG. 4). Similar to the 48-hour time point, at 24 hours P19 and P23 transduced Mo-DCs also show higher CD80, CD83, and CCR7 expression, but with an additional up-regulation of CD86.

TABLE 3

The effects of Ad-P19 or Ad-P23 on Mo-DC surface marker expression

| | Percentage of GFP+ iDC coexpressing indicated markers | | | | | |
|---|---|---|---|---|---|---|
| | CD40 % | CD80 % | CD83 % | CD86 % | HLA-DR % | CCR7 % |
| Ad-LPS | 6.7 ± 4.8 | 75.8 ± 15.2 | 16.9 ± 9.3 | 24.1 ± 15.0 | 0.4 ± 0.5 | 50.2 ± 5.0 |
| Ad-WT | 1.3 ± 0.9 | 5.4 ± 0.3 | 3.8 ± 2.0 | 0.8 ± 0.2 | 0.6 ± 0.4 | 6.5 ± 3.7 |
| Ad-DN-WT | 1.6 ± 1.5 | 2.5 ± 2.8 | 1.1 ± 0.6 | 0.7 ± 0.2 | 2.1 ± 1.6 | 6.9 ± 5.1 |
| Ad-P19 | 2.5 ± 1.2 | 25.6 ± 2.3 | 8.1 ± 1.6 | 1.5 ± 0.9 | 1.4 ± 1.2 | 28.9 ± 12.8 |
| Ad-P23 | 4.0 ± 2.1 | 23.1 ± 0.6 | 8.0 ± 2.0 | 1.8 ± 1.3 | 0.8 ± 0.4 | 26.4 ± 8.1 |

Comparative analysis +/− standard deviation of flow cytometric analysis of different markers in 5 separate experiments. Primary Mo-DC transduced with adenovirus as shown. LPS is the positive control for the experiment transduced with empty GFP+ vector.

Mature DCs are associated with production of inflammatory cytokines and chemokines that define the subsequent anti-tumor response. Hence, we examined the secretory profile of Mo-DC transduced with DAP12 mutants after 5 days in culture. Ad-P19 and Ad-P23 transduced Mo-DCs secrete significantly higher levels of TNF-α, IFN-γ, IL-12p70 and IL-1β, similar to LPS-stimulated Mo-DCs, when compared to either untreated (Med) or Ad-GFP transduced Mo-DC (FIG. 3b, Table 4). These responses indicate a type I inflammatory response, as constitutively active DAP12 had little effect on IL-10 (FIG. 3b) and IL-15 secretion. Importantly, IL-8 which is a cytokine strongly linked to mobilization of myeloid cells, was also shown to be strongly induced by constitutively active DAP12 (P19 and P23), even above cells overexpressing WT DAP12 transfected cells, indicating that activation of DAP12 is critical to make MoDC capable of migration after stimulation. Therefore, constitutively active DAP12 constructs can induce a functional type 1 inflammatory and migratory response.

TABLE 4

| | Ad-GFP vs | | | | |
|---|---|---|---|---|---|
| | WT | DN-WT | Ad-P19 | Ad-P20 | Ad-P23 |
| TNFα | 0.9998 | >0.9999 | 0.0002 | 0.9987 | 0.1033 |
| IL-12p70 | 0.9985 | >0.9999 | <0.0001 | >0.9999 | 0.0752 |
| IL-10 | 0.9926 | 0.9963 | 0.9176 | 0.9406 | 0.4258 |
| IL-8 | 0.5549 | 0.9999 | 0.0005 | 0.8661 | 0.0048 |
| IFN-γ | 0.9996 | 0.9998 | 0.0002 | 0.9999 | 0.0559 |

| | Ad-GFP vs | | | |
|---|---|---|---|---|
| | WT | DN-WT | Ad-P19 | Ad-P23 |
| Proliferation | 0.3939 | 0.3638 | <0.0001 | <0.0001 |
| Lysis | 0.3906 | 0.7983 | <0.0001 | 0.0028 |
| Migration | 0.6277 | <0.0001 | <0.0001 | 0.117 |

| | Ad-GFP vs | | |
|---|---|---|---|
| | Ad-WT | Ad-P19 | Ad-P23 |
| ELISpot | 0.9995 | 0.1658 | 0.0026 |

ANOVA analysis of FIGS. 2b, 3a, 3b, 3c and 4b. Underline denotes p value is significant. Note that two bolded p-values in Ad-P23 close to significant.

(3) Constitutively Active DAP12 Induces Functional Activation of Mo-DC In Vitro

Given the fact that Ad-P19 and Ad-P23 up-regulate CCR7 expression on human Mo-DCs, which is associated with enhanced migration toward MIP-30 (CCL19) in vivo, and increase the secretion of IL-8 which is linked to migration, we examined whether Ad-P19 or Ad-P23 transduced human Mo-DC could migrate toward CCL19 in a chemotaxis trans-well assay. CCL19 induced an increase in migration of LPS-stimulated DCs, Ad-DN-DAP12, Ad-P19, and Ad-P23 transduced Mo-DCs, compared to cells untreated with CCL19 (FIG. 5a, Table 4). In contrast, exposure to Ad-GFP or Ad-DAP12 only slightly increased the CCL19-induced migration of DCs. Furthermore, when these experiments were performed in the absence of CCL19 there were no significant differences between the migration patterns of transduced DCs indicating that Ad-P19 or Ad-P23 can induce Mo-DC migration in vitro.

To understand if this mobilization is also linked to increased antigen presentation and T cell activation, T cell cytolytic activity was tested by $^{51}$Cr release assays after stimulation with Mo-DC pulsed with K562 tumor cell lysates. $^{51}$Cr-labeled target K562 were cultured with CD8+ T cells stimulated with pulsed Mo-DC and compared with T cells stimulated with un-pulsed Mo-DC. CD8+ T cell stimulated with Mo-DC transduced with Ad-P19 or Ad-P23 showed evidence of antigen-specific lysis of K562 cells (FIG. 5b, Table 4). CD8+ T cell stimulated with Mo-DC transduced with Ad-GFP, Ad-WT or Ad-DN-WT showed low levels of cytotoxicity against K562 cells. Furthermore, T cells stimulated with Mo-DC in the absence of tumor cell lysates failed to demonstrate lysis of $^{51}$Cr-labeled targets. These data demonstrate that Ad-P19 or Ad-P23 can stimulate Mo-DCs to induce tumor antigen-specific CD8+ CTL responses.

Figure 5D:
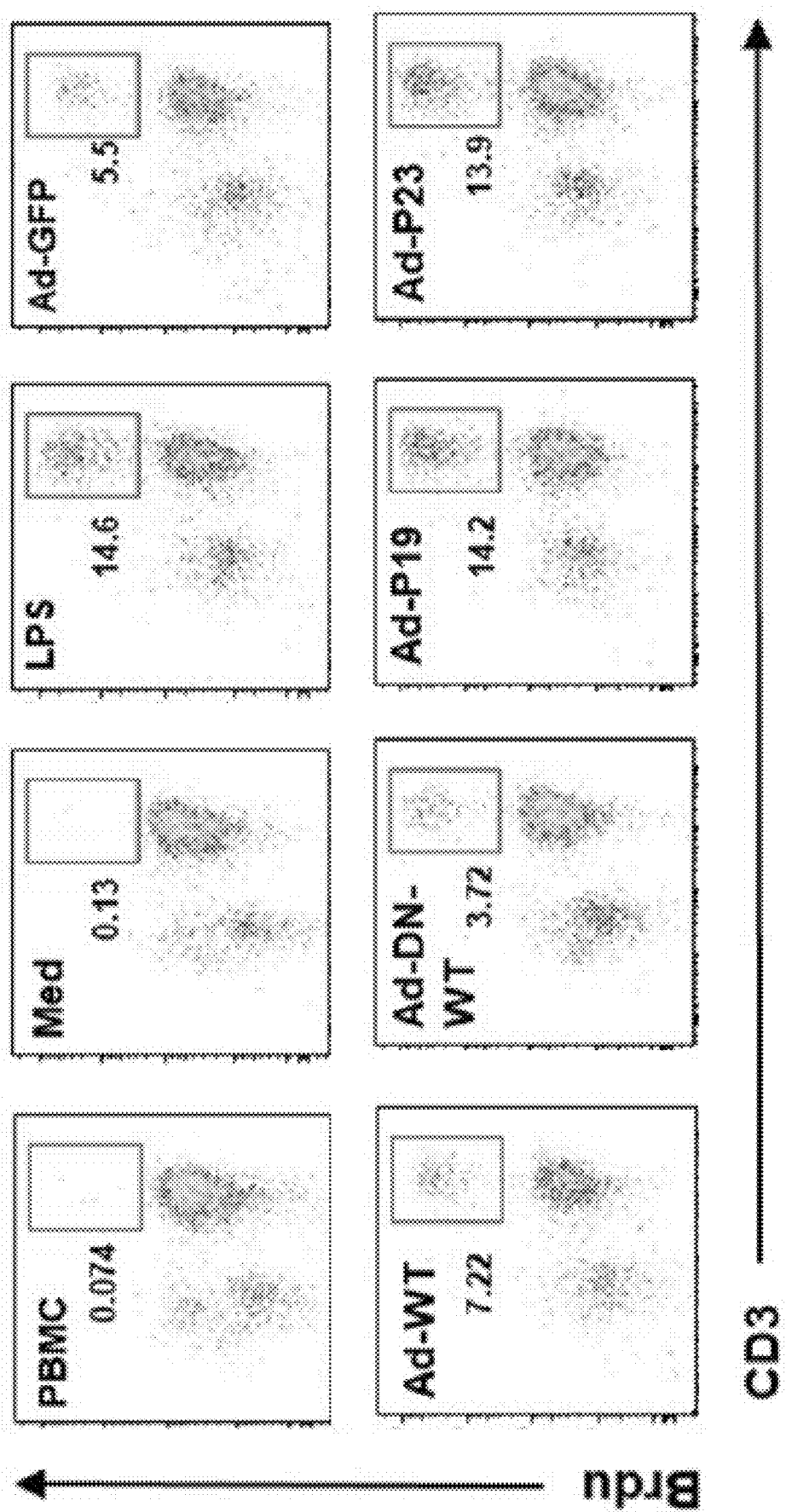

In order to demonstrate the ability for these mutant DAP12 constructs to confer DC induced T cell proliferation, DCs were transduced with Ad-GFP, Ad-WT, Ad-DN-WT, Ad-P19 or Ad-P23 for 48 h and examined for their capacity to stimulate the proliferation of T cells. Again, untreated cells (media) served as negative controls while LPS treated cells served as a positive control. P19 and P23 transduced Mo-DC pulsed with K562 tumor lysate induced significant CD8+ T cell proliferation (FIG. 5c, Table t2) as well as overall CD3+ positive T cell proliferation after 5 days co-culture as assessed by BrdU incorporation, when compared to WT control (FIG. 5d, Table 4). Specifically, we see a doubling of proliferating CD8+ T cells, similar to that of LPS stimulated DC. Consistent with the above phenotypical assays, Ad-P19 and Ad-P23 induced the greatest T cell proliferation.

(4) Intratumoral Injection of Constitutively Active DAP12 Transduced DC Induces Significant Antitumor Effects In Vivo To examine the in vivo antitumor effect of intratumoral injection of caDAP12 activated bone marrow derived DC we used a subcutaneous murine melanoma model. B16 cells ($2.5\times10^5$) were injected in the right suprascapular area of C57BL/6 mice on day 0 (FIG. 6a) followed 8 days later by intratumoral injection of DCs alone (medium, MED), treated with HBSS alone, or transduced with Ad-GFP, Ad-WT, Ad-P19 or Ad-P23 (n=7 mice per group, GFP in FIG. 7a). Treatment with DC alone (MED), HBSS alone, Ad-GFP DC, or Ad-WT DC did not show significant antitumor effects while significant antitumor effects were observed in mice treated with DC transfected with Ad-P19 or Ad-P23 (FIG. 6a, Table 5, FIG. 7b).

TABLE 5

Paired student t-test values

| | Medium | Ad-GFP | Ad-WT | Ad-p19 | Ad-P23 |
|---|---|---|---|---|---|
| Day 7 | | | | | |
| HBSS vs | 0.227012 | 0.155804 | 0.00562 | 0.000243 | 0.132482 |
| Med vs | | 0.168829 | 0.085582 | 0.126083 | 0.544817 |
| AdGFP vs | | | 0.168767 | 0.193095 | 0.720357 |
| Day 10 | | | | | |
| HBSS vs | 0.838925 | 0.2088 | 0.191246 | 0.000179 | 0.003925 |
| Med vs | | 0.003124 | 0.111424 | 0.004858 | 0.008461 |
| AdGFP vs | | | 0.7023 | 0.021071 | 0.02903 |
| Day 14 | | | | | |
| HBSS vs | 0.087598 | 0.120166 | 0.100367 | 0.000196 | 0.000718 |
| Med vs | | 0.450491 | 0.163527 | 0.008035 | 0.002613 |
| AdGFP vs | | | 0.245815 | 0.011623 | 0.004682 |
| Day 18 | | | | | |
| HBSS vs | 0.064465 | 0.202463 | 0.016984 | 0.000607 | 0.003114 |
| Med vs | | 0.088198 | 0.955855 | 0.009669 | 0.009832 |
| AdGFP vs | | | 0.1784 | 0.001072 | 0.001837 |
| Day 21 | | | | | |
| HBSS vs | 0.069485 | 0.260954 | 0.061666 | 0.003163 | 0.007203 |
| Med vs | | 0.104447 | 0.671304 | 0.001028 | 0.002993 |
| AdGFP vs | | | 0.549291 | 0.004537 | 0.001536 |
| Day 25 | | | | | |
| HBSS vs | 0.13873 | 0.055627 | 0.09018 | 0.010939 | 0.00984 |
| Med vs | | 0.259094 | 0.111343 | 0.003299 | 0.001504 |
| AdGFP vs | | | 0.22362 | 0.008242 | 0.002021 |
| Day 28 | | | | | |
| HBSS vs | 0.225245 | 0.053565 | 0.042643 | 0.01083 | 0.014383 |
| Med vs | | 0.943765 | 0.008639 | 0.022113 | 0.012809 |
| AdGFP vs | | | 0.082507 | 0.063996 | 0.017233 |

Paired student t-test analysis of tumor volume comparisons in FIG. 4a. Bold denotes p value is significant.

DCs are antigen presenting cells that play a role in T cell activation and hence we evaluated the functional activity of CD8+ T cells isolated from spleens of the B16 murine melanoma model mice immunized with DCs. C57BL/6 mice (four per group) received $5 \times 10^6$ DCs intravenous once a week for three weeks. Seven days after the last immunization, $CD8^+$ T cells were purified from pooled splenocytes and IFNγ secretion was evaluated by EliSpot as a measure of activation. We observed that the proportion of the $CD8^+$ T cells producing IFN-γ against B16 melanoma cells was significantly greater in $CD8^+$ T cells from mice immunized with DC/Ad-P19 or DC/Ad-P23, compared to mice immunized with Ad-GFP/DC or Ad-DAP12/DC (FIG. 6b). Substantial evidence indicates that the tumor microenvironment is crucial in tumor progression. In particular, tumor-infiltrating lymphocytes (TILs) have been recognized as principal effectors of the local antitumor immune response. We therefore determined whether Ad-P19/DC or Ad-P23/DC treatment enhanced the presence of $CD8^+$ TILs in murine melanoma tumors. Immunohistochemical staining revealed that the number of tumor-infiltrating $CD3^+$ T cells and CD8+ T cells in the group of mice treated with Ad-P19/DC or Ad-P23/DC was significantly greater than that in the group of mice treated with Ad-GFP/DC, Ad-WT/DC or DC alone (FIG. 6c).

b) Discussion

Efficient antigen presentation by DCs is a hallmark of an effective immune response. Despite this, deficient antigen presentation properties are shown by DCs in patients with cancer, which induce a cellular immune deficit that is not intrinsically overcome, and leads to a lack of therapeutic responsiveness. As a result, immunotherapy using ex vivo expanded DC is a potential method to give rise to a cellular immune response, in a situation where tumor induced immune suppression is present. However, despite the promise of DC vaccines, where isolated DC are loaded with tumor antigen, little success has been seen in clinical trials. Based on the fact that DC maturation is a necessary first step for these cells to uptake antigen, migrate, and stimulate T cells, one option is that ex vivo generated DCs from advanced cancer patients might not have sufficient capacity for inducing tumor antigen-specific immune responses due to the inefficiency of typical DC differentiation cultures (i.e.: with GM-CSF and IL-4 or other stimulating cocktails). In the present study we tested the premise that constitutive activation of DAP12 can help override these hurdles for the activation and maturation of DCs, leading to the upregulation of their immune-stimulatory and antigen-presenting capabilities for potential therapeutic use.

Many tumors secrete soluble cytokines that can inhibit the maturation of DC and T cells, and thus suppress the overall immune response. Additionally, in DCs, like other immune cell subsets, there is a unique and complex balance between ITAM and ITIM signaling, and the outcome of such signaling can lead to either cell activation and cytotoxicity, or ineffective cytokine production and death. DAP12 is one such ITAM containing signaling protein that has been shown to be critical for myeloid cell functionality and survival. As a result, we sought new methods to enhance DC activity for adoptive transfer by manipulating this balance using constitutively active mutant DAP12 and demonstrated that transduction of constitutively active DAP12 mutants into primary MoDCs leads to active, functional and responsive DCs, that induce significant antitumor effects in a B16 murine melanoma model. The introduction of constitutively active DAP12 resulted in improved functionality of DCs, indicating that DAP12 has activating properties. The data demonstrated that, unlike wild type DAP12 (Ad-WT) and dominant negative DAP12 (Ad-DN-WT), introduction of constitutively active DAP12 (Ad-P19 or Ad-P23) to immature DCs promote DC maturation, as indicated by up-regulation of CD80, CD83 and CCR7. Interestingly, we found that both Ad-P19 and Ad-P23 were able to induce DC activation including cytokine release, migration, and efficiently increase T cell proliferation and tumor antigen-specific $CD8^+$ cytolytic responses. It is important to note, however, that despite the lack of SYK activation dominant negative DAP12 was able to still induce significant migration indicating an alternative migratory signaling effect of the constructs. This is consistent with the binding of DAP12 to many different receptors and with a variety of functions similar to Syk, a kinase that, apart from self-regulation, can modulate different pathways. Apart from other activated pathways the strength of the interaction between SYK and DAP12 could cause differential effects. The results indicate by showing that Syk and DAP12 are phosphorylated in WT-transfected AD293 cells (FIG. 1C) but they do not physically interact (FIG. 1D), as occurs in P19 and P23- transfected cells. The data can be interpreted as constitutive active DAP12 having a more sustained binding, leading to higher phosphorylation, than the WT transfected cells which may affect the direction of the downstream pathways.

DCs have been used to deliver tumor antigen to elicit an antigen dependent immune response to tumor. Since DCs are professional APCs, their ability to process and present antigen is especially important, in a situation where antigen presentation is hampered by tumor induced immune suppression. Ex vivo generation of DCs has involved multiple approaches including peptide loading, differential cytokine support, and adjuvant approaches using toll like receptor ligands. All of the approaches aim to achieve a functional mature DC that will be reinfused into the patient to elicit a potent cellular immune response. However, these vaccines, despite showing early promise, have yet to display significant efficacy in the tumor setting, potentially due to becoming an immature, tolerogenic DC, which inhibit subsequent effector function. Additionally, immature DC, when infused, will not traffic to the tumor like mature DC's do, as fully mature DCs upregulate CCR7 and respond to CCL19 chemotaxis. It is for these reasons we evaluated enhancing DC functionality through an ITAM containing, constitutively active adaptor protein, to facilitate DC maturation into an antigen presenting, anti-tumor DC.

Herein is shown that transfection with constitutively active DAP12 stimulates Myeloid Derived Suppressor Cell (MDSC) maturation, and improves colony formation in myelodysplastic syndromes. The role of DAP12 in the activation of antigen presenting cell responses has been established. Moreover, early studies in myeloid cells identified DAP12 as a receptor by showing that when ligated by TREM1 it can induce activation and inflammatory responses, particularly of neutrophils and macrophages and the changes in these DAP12 pathways are linked to cancer survival. Additional pro-inflammatory responses have been shown to be amplified by DAP12 in the context of systemic inflammation, where increased cytokine levels were seen. However, unlike MoDC's, plasmacytoid dendritic cells (pDC) in response to DAP12 signaling with SIGLEC-H down-modulate the large quantities of type I interferon normally present in pDCs and leads to reduced responsiveness to TLR ligands. This is advantageous in the context disclosed herein as reduction of TLR ligands also limits the tolerogenic nature of the microenvironment and potentially allows pDCs anti-tumor responses. Based on the fact that GM-CSF can modulate myeloid cells, pre-activation with GM-CSF, or similar myeloid factors, can lead to myeloid skewing into immature suppressive cells, again indicating that forced DAP12 is a novel mechanism to break strong tolerance such as the one induced by the tumor microenvironment. This is critical as it is known that the tumor microenvironment can subvert the expression and functionality of DAP12 in malignancy.

In summary, the data indicates that transduction of constitutively DAP12 enhances DC function without inducing adverse events in this preclinical model of subcutaneous B16 melanoma. Such a modality represents a significant improvement over other more inflammatory adjuvants, such as TLR ligands, or complete/incomplete Freud's adjuvant. The work shows that DAP12 activation is both an important mediator of DC activation and maturation, and while the complex nature of ITAM signaling needs additional study, the groundwork laid here indicates that constitutively active DAP12 represents an attractive and potent option for DC vaccine augmentation. The combination of intratumor administration of Ad-P19/DC or Ad-P23/DC can elicit a strong antitumor immune response in vivo, indicating that constitutively activated DAP12 gene therapy could be a useful strategy for directly activating DCs for cancer immunotherapy.

c) Materials and Methods (1) Isolation of PBMCs and Human Monocyte-Derived DC (hMoDC) Preparation Peripheral blood was purchased as buffy coats from normal healthy donors that donated blood at the Southwest Florida Blood Bank (Tampa, FL). Peripheral blood mononuclear cells (PBMCs) were separated by Ficoll-Hypaque gradient centrifugation (Cellgro; Mediatech). Cells at the interface were collected and washed three times in cold PBS. After isolation, PBMCs were cultured in 10% FBS RPMI-1640 (GIBCO) at 37° C. and 5% $CO_2$. After 2 hours, the non-adherent cells were removed and the culture plates were washed with cold PBS to obtain a pure fraction of adherent $CD14^+$ monocytes. The adherent cells were re-suspended in RPMI-1640 medium supplemented with 10% FBS, 1000 U/ml GM-CSF (Berlex) and 500 U/ml IL-4 (R&D Systems) in a humidified incubator at 37° C. and 5% $CO_2$ for 5 days. Media was replaced every three days while in culture. On day 5, these human monocyte-derived DCs (MoDCs) were further transduced with adenovirus at a multiplicity of infection (MOI) of 50 for an additional 2 days.

(2) Construction of DAP12 Mutants

Two-step overlap extension polymerase chain reaction (PCR) was used to construct DAP12 mutants. Mutants were created by PCR mutagenic primers using wild-type DAP12 as a template using the primers in Table 6. P23 was recently reported in a publication. The mutant DAP12 DNA fragments were ligated into the vector PCDNA3 at the Hind III, XhoI restriction sites and cloned into *Escherichia coli*. Sequence analysis was performed to verify the sequence.

TABLE 6

Mutagenesis Primers

| Primer name | Sequence |
|---|---|
| PCDNA3 | 5'-AATACGACTCACTATAGGGA-3' (SEQ ID NO: 2) |
| | 5'-GGACAGTGGGAGTGGCACCTTCCA-3' (SEQ ID NO: 3) |
| DAP12 P7 | 5'-GTAGACAACCGACCTCTGACC-3 (SEQ ID NO: 4) |
| | 5'-AGGTCGGTTGTCTACAGCGAC-3' (SEQ ID NO: 5) |
| DAP12 P8 | 5'-CGCTCATTTGTATTCCGGCCTCTGTGC-3' (SEQ ID NO: 6) |
| | 5'- CAGAGGCCGGAATACAAATGAGCGGCC-3' (SEQ ID NO: 7) |

TABLE 6-continued

Mutagenesis Primers

| Primer name | Sequence |
|---|---|
| DAP12 P9 | 5'-ACCGAGTCGCCTGATC AGGAGCTCCA-3' (SEQ ID NO: 8) |
| | 5'-GAGCTCCTGATCAGGCGACTCGGT-3' (SEQ ID NO: 9) |
| DAP12 P10 | 5'-CGCTCATTTCTCTTCCGGCCTCTGTGT-3' (SEQ ID NO: 10) |
| | 5'-CAGAGGCCGGAAGAGAAATGAGCGGCC-3' (SEQ ID NO: 11) |
| DAP12 P11 | 5'-TCGGATGTCGACAGCGACCTCAAC-3' (SEQ ID NO: 12) |
| | 5'-GTGTTGAGGTCGCTGTCGACATCC-3' (SEQ ID NO: 13) |
| DAP12 P17 | 5'-CAGAGGTCGGTTCGCTACAGCGACCTC-3' (SEQ ID NO: 14) |
| | 5'-GTCGCTGTAGCGAACCGACCTCTGACC-3' (SEQ ID NO: 15) |
| DAP12 P18 | 5'-CAGAGGTCGCATGTCTACAGCCACCTCAACAC-3' (SEQ ID NO: 16) |
| | 5'-TGTTGAGGTGGCTGTAGACATGCGACCTCTGAC-3' (SEQ ID NO: 17) |
| DAP12 P19 | 5'-GATGTCTACAGCAACCTCAACACACAGAG-3' (SEQ ID NO: 18) |
| | 5'-CTGTGTGTTGAGGTTGCTGTAGACATCCG-3' (SEQ ID NO: 19) |
| DAP12 P20 | 5'-ACCGAGTCGCCTTGTCAGGAGCTCCAGG-3' (SEQ ID NO: 20) |
| | 5'-TGGAGCTCCTGACAAGGCGACTCGGTCTC-3' (SEQ ID NO: 21) |
| DAP12 P21 | 5'-GTCGGATGTCTGCAGCGACCTCAACACAC-3' (SEQ ID NO: 22) |
| | 5'-GTTGAGGTCGCTGCAGACATCCGACCTC-3' (SEQ ID NO: 23) |
| DAP12 P22 | 5'-GATGTCTACAGCGACTACAACACACAGAG-3' (SEQ ID NO: 24) |
| | 5'-GCCTCTGTGTGTTGTAGTCGCTGTAGAC-3' (SEQ ID NO: 25) |
| DAP12 P23 | 5'-GTCTACAGCGACCTCAAAACACAGAGGC-3' (SEQ ID NO: 26) |
| | 5'-CGGCCTCTGTGTTTTGAGGTCGCTGTAG-3' (SEQ ID NO: 27) |

(3) Preparation of Adenoviral Vector

DAP12 mutant plasmids were sub-cloned into a pShuttle-IRES-hrGFP-1 vector (containing the CMV promoter and hrGFP). The PmeI-digested shuttle vectors were then co-transformed into electro-competent BJ5183 bacteria with pAdEasy-1 (containing the viral backbone) and selected on Kanamycin LB plates. The plasmid in the bacteria was amplified and purified using a plasmid maxiprep system (Qiagen). The complete adeno-vector was linearized by PacI digestion and then transfected into AD293 cells using Lipofectamine following manufacturer recommendations (Invitrogen). The human AD293 cell line was obtained from the American Type Culture Collection and was maintained in Dulbecco's modified Eagle's medium supplemented with 10% fetal bovine serum, 100 U/ml penicillin, and 100 µg/ml streptomycin at 37° C. in a humidified 5% $CO_2$ incubator. All recombinant adenoviruses were amplified in AD293 cells. Viral stocks were obtained by amplification of the AD293 cells followed by standard two-step CsCl gradient ultracentrifugation, dialysis, and storage as a glycerol (10% volume/volume) stock at −80° C. The titer of each viral stock was routinely $10^{11}$-$10^{12}$ plaque forming units (pfu) when assayed on AD293 cells.

(4) Crosslinking, Immunoprecipitation and Western Analysis

AD293 cells (a cell line derived from HEK293 with improved cell adherence and plaque formation, Agilent) were washed with Dulbecco's PBS (DPBS), and resuspended in 2.0 µg/ml of anti-human TREM-1 antibody (R&D Systems) on ice for 30 min. After washing with DPBS, cells were incubated with 1.0 µg/ml of Affinipure rabbit anti-mouse IgG (H+L) Ab (Jackson Immunoresearch) at 37° C. for 10 min. Cells were then scraped off the plates and followed by centrifugation at 400 g for 10 minutes at 4° C. Cells were washed twice with cold 1×DPBS and lysed on ice for 30 min at 4° C. in 1 ml of lysis buffer (1% NP-40, 10 mM Tris, 150 mM NaCl, 0.5 mM phenylmethylsulfonyl fluoride, 10 mM iodoacetamide, 50 mM NaF, 1 mM ethylenediaminetetraacetic acid, 1 mM sodium orthovanadate, 0.25% sodium Deoxycholate, 10 µl Ala-Ala-Phe p-nitroanilide (SIGMA), 10 µl protease cocktail I (SIGMA cat #P2850) and 10 µl protease cocktail II (SIGMA cat #P5726). Cell lysates were centrifuged at 12,000 g at 4° C. for 15 minutes to remove nuclei and cell debris, after which the clarified lysate supernatant was isolated. The protein concentration of the soluble extracts was determined using the Bradford protein assay (Bio-Rad, Hercules, CA, USA) following manufacturer protocol. Western blots were blocked in PBST containing 4% BSA for 1 h and then incubated overnight at 4° C. in primary antibodies. Mouse anti-flag (M2) was purchased from Sigma, phosphotyrosine (clone 4G10) was purchased from Upstate Biotechnology. Rabbit Abs to phospho-ERK ($Thr^{202}/Tyr^{204}$), phospho-Syk ($Tyr^{525/526}$), pan- ERK and pan-Syk were purchased from Cell Signaling Technology. Blots were washed three times in PBST, followed by incubation for 1 hour with horseradish peroxidase-conjugated secondary antibodies in PBST containing 5% non-fat dried milk. The blots were washed three times in PBST followed by detection with enhanced chemiluminescence detection system (ECL, Amersham, Piscataway, NJ, USA). In some instances, blots were stripped in stripping buffer (Pierce) at 37° C. for 15 min. For IP, cleared lysates with equivalent amount of protein were incubated with 5 μg of Myc-Tag antibody (SIGMA) with overnight rotation at 4° C., then 30 μl of protein G-agarose beads (Sigma) were added, and allowed to mix for 2 h at 4° C. The precipitates were pelleted by centrifugation, the supernatant was removed, and the pellet washed three times with lysis buffer, and proteins were eluted by heating beads in 50 uL of 2×SDS sample buffer for 10 50° C. Following pelleting by centrifugation, the supernatant was transferred to a new microcentrifuge tube, and DTT was added at 100 mM. 50 uL of 3×SDS sample buffer with DTT was added to the pelleted beads, constituting a second elution. Following a 5-10 minute boil of samples, proteins were resolved by 10% SDS-polyacrylamide gel electrophoresis and transferred to polyvinylidene difluoride (PVDF) membranes for western blotting.

(5) Flow Cytometry

Dendritic cells were harvested, and $1\times10^6$ cells were washed with cold 1×DPBS and then incubated with anti-CD40-APC (BD Pharmigen), anti-CD80-PE (eBiosciences), anti-CD83-PE-Cy5 (BD Pharmigen), anti-CD86-PE (eBiosciences), anti-HLA-DR-PE (eBiosciences) and anti-CCR7-PE-Cy7 (BD Pharmigen) labeled antibodies (BD Pharmigen) for 30 min on ice. After washes, cells were fixed with 1% paraformaldehyde (Fisher Scientific) and data were collected on an LSRII flow cytometer (BD Pharmigen). Expression of cell surface markers was analyzed on gated GFP positive cells using Flowjo 6.3.4 software.

(6) DC Migration Assay

Day 5 DCs were transduced with DAP12 adenovirus for 48 hours, cells were washed to remove unbound virus, and assayed for migration in response to the chemokine CCL19 (100 ng/mL). Assay medium (25 μl) containing serum-free medium or chemokine CCL19 (100 ng/mL), was loaded into the lower chambers of a trans-well plate. Fifty microliters of DCs suspension ($1\times10^6$/ml) in plain RPMI 1640 medium was added to the upper compartment of the chemotaxis chamber. The two compartments were separated by a 5-μm pore size polycarbonate filter (Nucleopore Corp., Pleasanton, CA). Spontaneous migration was determined as the movement of cells toward the control medium. The chamber was incubated for 1 hour at 37° C. in humidified 5% $CO_2$ incubator. After culture the filter was removed and stained with Diff-Quik (Harleco, Gibbstown, NJ). The number of DCs from the upper chamber that infiltrated across the filter to appear on the underside was recorded in three oil immersion fields for each well, and each experimental condition was assayed in triplicate wells.

(7) Cytotoxicity Assays

CD8+ T cell were isolated from healthy volunteer PBMC using a human CD8+ T cell enrichment cocktail (RosetteSep). These cells were then stimulated in vitro with K562 lysate-pulsed DCs (DC:T cell ratio 1:20). At day 6, CD8+ T cell were washed extensively in PBS and used in 5 hour $^{51}$Cr-release assay. Briefly, target tumor cells were labeled with 200 ρCi of $^{51}$Cr in 0.2 ml of medium at 37° C. in a 5% $CO_2$ atmosphere for 1 hour. The cells were then washed three times and added to effector cells at concentration of $5\times10^3$ cells/well in 96-well round-bottomed culture plates, resulting in E/T ratios ranging from 20:1 to 10:1 in a final volume of 0.2 ml in each well. After 5 hour incubation at 37° C., 100 μl of culture supernatants was harvested and counted in a gamma counter. The percent specific $^{51}$Cr release was determined according to the equation [(experimental cpm−spontaneous cpm)/total cpm incorporated]×100. All determinations were done in triplicate, and the SEM of all assays was calculated.

(8) T Cell Proliferation Assays

Day 5 DCs were either transduced with DAP12 adenoviruses or LPS followed by a pulse with K562 lysate. After harvest, DCs were treated with mitomycin C for 1 hour at 37°, then cells were washed 3 times with 1×DPBS and counted. Cells were plated in a 48-well plate at a 1:20 DC:PBMCs cell ratio ($2.0\times10^5$ PBMC cells/well). After 5 days co-culture, cells were harvested, washed, counted, and analyzed by flow cytometry. To measure proliferation by BrdU incorporation, 10 μM BrdU was added to cell cultures during the final 30 min, and then cells were harvested, stained for CD3, washed, fixed, and permeabilized, then incubated with 300 μg/ml DNase for 1 hour at 37° C. After washing, cells were incubated with APC-conjugated anti-BrdU antibody for 30 minutes at room temperature and analyzed on a LSRII flow cytometer (BD Pharmigen).

(9) Antitumor Effects

B16 tumor cells ($2.5\times10^5$) were injected subcutaneously in the right suprascapular area of C57BL/6 mice, and seven-day-old established tumors were treated with an intratumoral injection of $1\times10^6$ DCs infected with adenovirus in a volume of 100 μl of HBSS administered once a week for 3 weeks. Treatment groups included MED (untreated)/DC, Ad-GFP/DC, Ad-WT/DC, Ad-P19/DC, Ad-P23/DC or HBSS alone with each group consisting of seven animals. Mice received $1\times10^7$ PFU of adenoviral vector or HBSS as a control on days 13 and 20. Two bisecting diameters of each tumor were measured with calipers, and tumor size was measured every 3-4 days. The volume was calculated using the formula V=0.4 $ab^2$ with "a" as the larger diameter and "b" as the smaller diameter. The total length of the study was 28 days.

(10) ELISA and EliSpot Assays

Human MoDC ($1\times10^6$ cells/ml) were transduced with DAP12 adenoviruses or LPS for 48 h. Supernatants were collected and analyzed for the presence of IL-12p70, IL-10, TNF-α, IFN-γ, and IL-1β by ELISA (Ready-SET-Go) following the manufacturer's instructions (eBiosciences). ELISA kit for IL-15 were purchased from BD Biosciences. For detection of CD8+ T cells secreting IFN-γ, EliSpot was performed using CD8+ T cells from spleens that were purified by positive selection using antibody-coated magnetic beads following the directions provided by the vendor (Miltenyi Biotec; Auburn, CA). Responder (CD8 purified) cells were incubated at $3\times10^5$, $1\times10^5$ and $3\times10^4$ cells per well together with $5\times10^4$ stimulator cells (B16 cells). Cultures were incubated at 37° C. for 20 hours and spots (IFN-γ producing cells) were developed as described by the EliSpot kit manufacturer (Mabtech, Inc., Mariemont, OH). Spot counting was done with an AID EliSpot Reader System (Autoimmun Diagnostika GmbH, Strassberg, Germany).

(11) Immunohistochemistry Staining

Formalin-fixed, paraffin-embedded tumor tissues were cut into 5-μM sections. Slides were stained using a Ventana Discovery XT automated system (Ventana Medical Systems, Tucson) as per manufacturer's protocol with proprietary reagents. Briefly, slides were deparaffinized on the automated system with EZ Prep solution (Ventana). Heat-induced epitope retrieval method was used in Cell Conditioning solution (Ventana). To block endogenous peroxides and protein the Ventana Discovery XT Inhibitor CM was added to the slides. A rabbit polyclonal primary antibody that reacts to CD3 (Cell Marque, Rocklin, CA) was used at a prediluted strength and incubated for 32 min. The Ventana Anti-rabbit secondary Antibody was used for 20 min. A rabbit monoclonal primary antibody that reacts to CD8 (Abcam, Cambridge, MA) was used at 1:25 and incubated for 60 min. The Ventana Anti-rabbit secondary Antibody was used for 16 min. The detection system used was the Ventana Chromo-Map DAB kit and slides were then counterstained with hematoxylin. All of these were performed automatically by the system. Slides were then dehydrated and coverslipped as per normal laboratory protocol.

(12) Generation of Murine Bone Marrow-Derived DC and Transduction with DAP12 Adenovirus Male C57BL/6 mice aged from 6 to 8 weeks were purchased from NCI-Harlan (Fredrick, MD). All mice were housed in pathogen-free units of the Division of Comparative Medicine at H. Lee Moffitt Cancer Center, University of South Florida. Bone marrow MNCs were isolated from the tibias and femurs of C57BL/6 mice and the red blood cells were lysed. DCs were isolated using microbeads and LSMACS columns according to the manufacturer's protocol (Miltenyi Biotec). Purified DCs were maintained at 37° C. in 5% C02-humidified atmosphere using RPMI 1640 supplemented with 10% fetal bovine serum (FBS), 20 ng/mL murine recombinant GM-CSF and 10 ng/mL IL-4. Cell cultures were incubated for 6 days with a media change every 2 days. Recombinant murine IL-4 was purchased from RDI and murine GM-CSF was purchased from Biosource.

On day 6, BMDCs were transduced with adenovirus at a multiplicity of infection (MOI) of 200. Briefly, BMDCs were seeded in 2% FBS, antibiotics-free RPMI containing the desired number of viral particles in a final volume of 200 µl. The plates were incubated overnight at 37° C. followed by culturing in complete culture medium with the cytokines for an additional 24 h. BMDCs were harvested, washed with HBSS three times, and removed dead cells using Dead Cell Removal kit prior to receiving intravenous (i.v.) injection. In control groups, mice received BMDCs that did not undergo transduction.

(13) Immunizations

Day 6 BMDCs were transduced with MED, Ad-GFP, Ad-P19, Ad-P23 or Ad-DAP12, and the next day they were pulsed with B16 lysate for 24 h. After DCs were harvested, dead cells were removed using Dead Cell Removal kit ((Miltenyi Biotec; Auburn, CA). For DCs immunizations, B6 mice were injected intravenously with a $2.5 \times 10^6$ treated DCs in a volume of 300 µl once a week for 3 weeks. CTLs for Elispot assays were obtained from DCs-immunized mice 7 days after the third immunization.

(14) Statistical Analysis

Statistical significance to assess the numbers of antigen-specific CD8+ T cells (ELISPOT) and cytokine levels (ELISA) were determined by unpaired Student t tests as well as one-way Analysis of Variance (ANOVA). Tumor sizes between 2 populations throughout time and cytotoxicity assays at various E:T ratios were analyzed for significance using two-way ANOVA. Additionally, area under the curve (AUC) analysis was conducted on the data from FIG. 6a. A one-way ANOVA was applied to these data to compare tumor size throughout time between various treatment groups. All analysis and graphics were done using GraphPad Prism, and p values <0.05 were considered to be statistically significant.

E. REFERENCES

Anguille, S.; Smits, E. L.; Cools, N.; Goossens, H.; Berneman, Z. N.; Van Tendeloo, V. F. Short-term cultured, interleukin-15 differentiated dendritic cells have potent immunostimulatory properties. *J Transl Med* 2009, 7, 109, doi:10.1186/1479-5876-7-109.

Ardavin, C.; Martinez del Hoyo, G.; Martin, P.; Anjuere, F.; Arias, C. F.; Marin, A. R.; Ruiz, S.; Parrillas, V.; Hernandez, H. Origin and differentiation of dendritic cells. *Trends in immunology* 2001, 22, 691-700.

Baggiolini, M.; Loetscher, P. Chemokines in inflammation and immunity. *Immunology today* 2000, 21, 418-420, doi:10.1016/s0167-5699(00)01672-8.

Bakker, A. B.; Hoek, R. M.; Cerwenka, A.; Blom, B.; Lucian, L.; McNeil, T.; Murray, R.; Phillips, L. H.; Sedgwick, J. D.; Lanier, L. L. DAP12-deficient mice fail to develop autoimmunity due to impaired antigen priming. *Immunity* 2000, 13, 345-353, doi:10.1016/s1074-7613(00)00034-0.

Barrow, A. D.; Trowsdale, J. You say ITAM and I say ITIM, let's call the whole thing off: the ambiguity of immunoreceptor signalling. *European journal of immunology* 2006, 36, 1646-1653, doi:10.1002/eji.200636195.

Berk, E.; Xu, S.; Czerniecki, B. J. Dendritic cells matured in the presence of TLR ligands overcome the immunosuppressive functions of regulatory T cells. *Oncoimmunology* 2014, 3, e27617, doi:10.4161/onci.27617.

Billadeau, D. D.; Leibson, P. J. ITAMs versus ITIMs: striking a balance during cell regulation. *The Journal of clinical investigation* 2002, 109, 161-168, doi:10.1172/JCI14843.

Bouchon, A.; Facchetti, F.; Weigand, M. A.; Colonna, M. TREM-1 amplifies inflammation and is a crucial mediator of septic shock. *Nature* 2001, 410, 1103-1107.

Bouchon, A.; Hernandez-Munain, C.; Cella, M.; Colonna, M. A DAP12-mediated pathway regulates expression of CC chemokine receptor 7 and maturation of human dendritic cells. *The Journal of experimental medicine* 2001, 194, 1111-1122.

Chen, B.; Zhou, M.; Zhang, H.; Wang, C.; Hu, X.; Wang, B.; Wang, E. TREM1/Dap12-based CAR-T cells show potent antitumor activity. *Immunotherapy* 2019, 11, 1043-1055, doi:10.2217/imt-2019-0017.

Chen, X.; Bai, F.; Sokol, L.; Zhou, J.; Ren, A.; Painter, J. S.; Liu, J.; Sallman, D. A.; Chen, Y. A.; Yoder, J. A., et al. A critical role for DAP10 and DAP12 in CD8+ T cell-mediated tissue damage in large granular lymphocyte leukemia. *Blood* 2008.

Chen, X.; Eksioglu, E. A.; Carter, J. D.; Fortenbery, N.; Donatelli, S. S.; Zhou, J.; Liu, J.; Yang, L.; Gilvary, D.; Djeu, J., et al. Inactivation of DAP12 in PMN inhibits TREM1-mediated activation in rheumatoid arthritis. *PloS one* 2015, 10, e0115116, doi:10.1371/journal.pone.0115116.

Chen, X.; Eksioglu, E. A.; Zhou, J.; Zhang, L.; Djeu, J.; Fortenbery, N.; Epling-Burnette, P.; Van Bijnen, S.; Dolstra, H.; Cannon, J., et al. Induction of myelodysplasia by myeloid-derived suppressor cells. *The Journal of clinical investigation* 2013, 123, 4595-4611, doi:10.1172/JCI67580.

Chen, X.; Eksioglu, E. A.; Zhou, J.; Zhang, L.; Djeu, J.; Fortenbery, N.; Epling-Burnette, P.; Van Bijnen, S.; Dolstra, H.; Cannon, J., et al. Induction of myelodysplasia by myeloid-derived suppressor cells. *The Journal of clinical investigation* 2013, 10.1172/JCI67580, doi:10.1172/JCI67580.

Davids, M. S.; Burger, J. A. Cell Trafficking in Chronic Lymphocytic Leukemia. *Open journal of hematology* 2012, 3, doi:10.13055/ojhmt_3_s1_03.120221.

De Vries, I. J.; Krooshoop, D. J.; Scharenborg, N. M.; Lesterhuis, W. J.; Diepstra, J. H.; Van Muijen, G. N.; Strijk, S. P.; Ruers, T. J.; Boerman, O. C.; Oyen, W. J., et al. Effective migration of antigen-pulsed dendritic cells to lymph nodes in melanoma patients is determined by their maturation state. *Cancer Res* 2003, 63, 12-17.

Dhodapkar, M. V.; Steinman, R. M.; Krasovsky, J.; Munz, C.; Bhardwaj, N. Antigen-specific inhibition of effector T cell function in humans after injection of immature dendritic cells. *The Journal of experimental medicine* 2001, 193, 233-238.

Donatelli, S. S.; Zhou, J. M.; Gilvary, D. L.; Eksioglu, E. A.; Chen, X.; Cress, W. D.; Haura, E. B.; Schabath, M. B.; Coppola, D.; Wei, S., et al. TGF-beta-inducible microRNA-183 silences tumor-associated natural killer cells. *Proc Natl Acad Sci USA* 2014, 111, 4203-4208, doi:10.1073/pnas.1319269111.

Eksioglu, E. A.; Eisen, S.; Reddy, V. Dendritic cells as therapeutic agents against cancer. *Frontiers in bioscience* 2010, 15, 321-347.

Eksioglu, E. A.; Kielbasa, J.; Eisen, S.; Reddy, V. Granulocyte-macrophage colony-stimulating factor increases the proportion of circulating dendritic cells after autologous but not after allogeneic hematopoietic stem cell transplantation. *Cytotherapy* 2011, 13, 888-896, doi:10.3109/14653249.2011.579956.

Fasbender, F.; Claus, M.; Wingert, S.; Sandusky, M.; Watzl, C. Differential Requirements for Src-Family Kinases in SYK or ZAP70-Mediated SLP-76 Phosphorylation in Lymphocytes. *Frontiers in immunology* 2017, 8, 789, doi:10.3389/fimmu.2017.00789.

Fontes, J. A.; Barin, J. G.; Talor, M. V.; Stickel, N.; Schaub, J.; Rose, N. R.; Cihakova, D. Complete Freund's adjuvant induces experimental autoimmune myocarditis by enhancing IL-6 production during initiation of the immune response. *Immun Inflamm Dis* 2017, 5, 163-176, doi:10.1002/iid3.155.

Giordano, D.; Magaletti, D. M.; Clark, E. A. Nitric oxide and cGMP protein kinase (cGK) regulate dendritic-cell migration toward the lymph-node-directing chemokine CCL19. *Blood* 2006, 107, 1537-1545, doi:10.1182/blood-2005-07-2901.

Gmyrek, G. B.; Akilesh, H. M.; Graham, D. B.; Fuchs, A.; Yang, L.; Miller, M. J.; Sandoval, G. J.; Sheehan, K. C.; Schreiber, R. D.; Diamond, M. S., et al. Loss of DAP12 and FcRgamma drives exaggerated IL-12 production and CD8(+) T cell response by CCR2(+) Mo-DCs. *PLoS one* 2013, 8, e76145, doi:10.1371/journal.pone.0076145.

Graham, D. B.; Stephenson, L. M.; Lam, S. K.; Brim, K.; Lee, H. M.; Bautista, J.; Gilfillan, S.; Akilesh, S.; Fujikawa, K.; Swat, W. An ITAM-signaling pathway controls cross-presentation of particulate but not soluble antigens in dendritic cells. *The Journal of experimental medicine* 2007, 204, 2889-2897, doi:10.1084/jem.20071283.

Heizmann, B.; Reth, M.; Infantino, S. Syk is a dual-specificity kinase that self-regulates the signal output from the B-cell antigen receptor. *Proceedings of the National Academy of Sciences* 2010, 107, 18563-18568, doi:10.1073/pnas.1009048107.

Hinshaw, D. C.; Shevde, L. A. The Tumor Microenvironment Innately Modulates Cancer Progression. *Cancer Res* 2019, 79, 4557-4566, doi:10.1158/0008-5472.CAN-18-3962.

Hiscott, J.; Pitha, P.; Genin, P.; Nguyen, H.; Heylbroeck, C.; Mamane, Y.; Algarte, M.; Lin, R. Triggering the interferon response: the role of IRF-3 transcription factor. *Journal of interferon & cytokine research: the official journal of the International Society for Interferon and Cytokine Research* 1999, 19, 1-13, doi:10.1089/107999099314360.

Ivanov, S.; Scallan, J. P.; Kim, K. W.; Werth, K.; Johnson, M. W.; Saunders, B. T.; Wang, P. L.; Kuan, E. L.; Straub, A. C.; Ouhachi, M., et al. CCR7 and IRF4-dependent dendritic cells regulate lymphatic collecting vessel permeability. *The Journal of clinical investigation* 2016, 126, 1581-1591, doi:10.1172/JCI84518.

Jakus, Z.; Fodor, S.; Abram, C. L.; Lowell, C. A.; Mocsai, A. Immunoreceptor-like signaling by beta 2 and beta 3 integrins. *Trends in cell biology* 2007, 17, 493-501, doi:10.1016/j.tcb.2007.09.001.

Jonuleit, H.; Kuhn, U.; Muller, G.; Steinbrink, K.; Paragnik, L.; Schmitt, E.; Knop, J.; Enk, A. H. Pro-inflammatory cytokines and prostaglandins induce maturation of potent immunostimulatory dendritic cells under fetal calf serum-free conditions. *European journal of immunology* 1997, 27, 3135-3142, doi:10.1002/eji.1830271209.

Kilpelainen, P. T.; Hietala, O. A. Mutation of aspartate-233 to valine in mouse ornithine decarboxylase reduces enzyme activity. *The international journal of biochemistry & cell biology* 1998, 30, 803-809.

Kluckova, K.; Kozak, J.; Szaboova, K.; Rychly, B.; Svajdler, M.; Suchankova, M.; Tibenska, E.; Filova, B.; Steno, J.; Matejcik, V., et al. TREM-1 and TREM-2 Expression on Blood Monocytes Could Help Predict Survival in High-Grade Glioma Patients. *Mediators of inflammation* 2020, 2020, 1798147, doi:10.1155/2020/1798147.

Lanier, L. L. DAP10- and DAP12-associated receptors in innate immunity. *Immunological reviews* 2009, 227, 150-160, doi:10.1111/j.1600-065X.2008.00720.x.

Lanier, L. L. NK cell recognition. *Annu Rev Immunol* 2005, 23, 225-274.

Lanier, L. L.; Bakker, A. B. The ITAM-bearing transmembrane adaptor DAP12 in lymphoid and myeloid cell function. *Immunology today* 2000, 21, 611-614.

Lanier, L. L.; Corliss, B. C.; Wu, J.; Leong, C.; Phillips, J. H. Immunoreceptor DAP12 bearing a tyrosine-based activation motif is involved in activating NK cells. *Nature* 1998, 391, 703-707, doi:10.1038/35642.

Laufer, J. M.; Kindinger, I.; Artinger, M.; Pauli, A.; Legler, D. F. CCR7 Is Recruited to the Immunological Synapse, Acts as Co-stimulatory Molecule and Drives LFA-1 Clustering for Efficient T Cell Adhesion Through ZAP70. *Frontiers in immunology* 2019, 9, doi:10.3389/fimmu.2018.03115.

Ma, Y.; Adjemian, S.; Mattarollo, S. R.; Yamazaki, T.; Aymeric, L.; Yang, H.; Portela Catani, J. P.; Hannani, D.; Duret, H.; Steegh, K., et al. Anticancer chemotherapy-induced intratumoral recruitment and differentiation of antigen-presenting cells. *Immunity* 2013, 38, 729-741, doi:10.1016/j.immuni.2013.03.003.

Michielsen, A. J.; Hogan, A. E.; Marry, J.; Tosetto, M.; Cox, F.; Hyland, J. M.; Sheahan, K. D.; O'Donoghue, D. P.; Mulcahy, H. E.; Ryan, E. J., et al. Tumour tissue microenvironment can inhibit dendritic cell maturation in colorectal cancer. *PLoS one* 2011, 6, e27944, doi:10.1371/journal.pone.0027944.

Mildner, A.; Jung, S. Development and function of dendritic cell subsets. *Immunity* 2014, 40, 642-656, doi:10.1016/j.immuni.2014.04.016.

Mocsai, A.; Humphrey, M. B.; Van Ziffle, J. A.; Hu, Y.; Burghardt, A.; Spusta, S. C.; Majumdar, S.; Lanier, L. L.;

Lowell, C. A.; Nakamura, M. C. The immunomodulatory adapter proteins DAP12 and Fc receptor gamma-chain (FcRgamma) regulate development of functional osteoclasts through the Syk tyrosine kinase. *Proc Natl Acad Sci USA* 2004, 101, 6158-6163, doi:10.1073/pnas.0401602101.

Palucka, K.; Banchereau, J. Dendritic-cell-based therapeutic cancer vaccines. Immunity 2013, 39, 38-48, doi:10.1016/j.immuni.2013.07.004.

Pinheiro da Silva, F.; Aloulou, M.; Benhamou, M.; Monteiro, R. C. Inhibitory ITAMs: a matter of life and death. *Trends in immunology* 2008, 29, 366-373.

Ravetch, J. V.; Lanier, L. L. Immune inhibitory receptors. *Science* 2000, 290, 84-89.

Reis e Sousa, C. Dendritic cells in a mature age. *Nature reviews. Immunology* 2006, 6, 476-483, doi:10.1038/nri1845.

Ribas, A.; Glaspy, J. A.; Lee, Y.; Dissette, V. B.; Seja, E.; Vu, H. T.; Tchekmedyian, N. S.; Oseguera, D.; Comin-Anduix, B.; Wargo, J. A., et al. Role of dendritic cell phenotype, determinant spreading, and negative costimulatory blockade in dendritic cell-based melanoma immunotherapy. *Journal of immunotherapy* 2004, 27, 354-367.

Ris-Stalpers, C.; Trifiro, M. A.; Kuiper, G. G.; Jenster, G.; Romalo, G.; Sai, T.; van Rooij, H. C.; Kaufman, M.; Rosenfield, R. L.; Liao, S., et al. Substitution of aspartic acid-686 by histidine or asparagine in the human androgen receptor leads to a functionally inactive protein with altered hormone-binding characteristics. *Molecular endocrinology* 1991, 5, 1562-1569, doi:10.1210/mend-5-10-1562.

Sedlik, C.; Orbach, D.; Veron, P.; Schweighoffer, E.; Colucci, F.; Gamberale, R.; Ioan-Facsinay, A.; Verbeek, S.; Ricciardi-Castagnoli, P.; Bonnerot, C., et al. A critical role for Syk protein tyrosine kinase in Fc receptor-mediated antigen presentation and induction of dendritic cell maturation. *Journal of immunology* 2003, 170, 846-852.

Sjolin, H.; Robbins, S. H.; Bessou, G.; Hidmark, A.; Tomasello, E.; Johansson, M.; Hall, H.; Charifi, F.; Karlsson Hedestam, G. B.; Biron, C. A., et al. DAP12 signaling regulates plasmacytoid dendritic cell homeostasis and down-modulates their function during viral infection. *Journal of immunology* 2006, 177, 2908-2916.

Tawab, A.; Fan, Y.; Read, E. J.; Kurlander, R. J. Effect of ex vivo culture duration on phenotype and cytokine production by mature dendritic cells derived from peripheral blood monocytes. *Transfusion* 2009, 49, 536-547, doi:10.1111/j.1537-2995.2008.02020.x.

Trakatelli, M.; Toungouz, M.; Blocklet, D.; Dodoo, Y.; Gordower, L.; Laporte, M.; Vereecken, P.; Sales, F.; Mortier, L.; Mazouz, N., et al. A new dendritic cell vaccine generated with interleukin-3 and interferon-beta induces CD8+ T cell responses against NA17-A2 tumor peptide in melanoma patients. *Cancer Immunol Immunother* 2006, 55, 469-474, doi:10.1007/s00262-005-0056-z.

Turnbull, I. R.; McDunn, J. E.; Takai, T.; Townsend, R. R.; Cobb, J. P.; Colonna, M. DAP12 (KARAP) amplifies inflammation and increases mortality from endotoxemia and septic peritonitis. *The Journal of experimental medicine* 2005, 202, 363-369, doi:10.1084/jem.20050986.

Turnis, M. E.; Rooney, C. M. Enhancement of dendritic cells as vaccines for cancer. *Immunotherapy* 2010, 2, 847-862, doi:10.2217/imt.10.56.

Underhill, D. M.; Goodridge, H. S. The many faces of ITAMs. *Trends in immunology* 2007, 28, 66-73, doi:10.1016/j.it.2006.12.004.

Villadangos, J. A.; Schnorrer, P. Intrinsic and cooperative antigen-presenting functions of dendritic-cell subsets in vivo. *Nature reviews. Immunology* 2007, 7, 543-555, doi:10.1038/nri2103.

Zhou, W.; Freed, C. R. Tyrosine-to-cysteine modification of human alpha-synuclein enhances protein aggregation and cellular toxicity. *The Journal of biological chemistry* 2004, 279, 10128-10135, doi:10.1074/jbc.M307563200.

What is claimed is:

1. A modified 12-kilodalton DNAX activating protein (DAP12) comprising one or more substitutions in the cytoplasmic domain of DAP12; wherein the one or more substitutions occurs at a residue corresponding to residues 91, 99, 100, 101, 102, 104, 105, 106, 111, or 112 of DAP12; wherein at least one substitution comprises an asparagine to lysine substitution at residue 106 (N106K).

2. The modified DAP12 of claim 1, wherein the one or more substitutions further comprise a Y91E, Y91C, Y91D, S99H, D100H, D100V, V101R, Y102C, Y102D, Y102E, D104H, D104N, L105Y, Y111D, Y111E, Y112D or Y112E substitution.

3. The modified DAP12 of claim 2, wherein the one or more substitutions mimic phosphorylation.

4. The modified DAP12 of claim 3, wherein the one or more substitutions comprise a Y91E, Y91D, Y102D, Y102E, Y111D, Y111E, Y112D or Y112E substitution.

5. The modified DAP12 of claim 2, wherein the one or more substitutions block activation of dendritic cells.

6. The modified DAP12 of claim 5, wherein the one or more substitutions comprise a Y91C and/or Y102C substitution.

7. The modified DAP12 of claim 2, wherein the one or more substitutions comprise a D100V or D100H substitution.

8. The modified DAP12 of claim 2, wherein the one or more substitutions disrupt the ITAM interaction.

9. The modified DAP12 of claim 8, wherein the one or more substitutions comprises a V101R substitution.

10. The modified DAP12 of claim 1, wherein the one or more substitutions occur in the immunoreceptor tyrosine-based activation motif (ITAM) sequence.

11. A vector comprising a nucleic acid sequence encoding the modified DAP12 of claim 1.

12. A dendritic cell comprising the modified DAP12 of claim 1.

13. A modified 12-kilodalton DNAX activating protein (DAP12) comprising one or more substitutions in the cytoplasmic domain of DAP12, wherein the one or more substitutions comprises a D100V substitution; a Y91E, Y102E, and Y112E substitution; a Y91D substitution; a Y91E, Y102E, Y111E, and Y112E substitution; a Y91D and Y102D substitution; a D100V and V101R substitution; a S99H and a D104H substitution; a D104N substitution; a Y91C substitution; a L105Y substitution; or a N106K substitution.

14. A method of treating melanoma in a subject comprising administering to the subject the modified DAP12 of claim 1.

15. The method of treating a subject with melanoma of claim 14, further comprising administering to the subject a dendritic cell.

16. The method of treating a subject with melanoma of claim 14, wherein the modified DAP12 is in dendritic cell.

17. The method of treating a subject with melanoma of claim 14, further comprising administering to the subject an anti-cancer immunotherapy.

18. The method of treating a subject with melanoma of claim 17, wherein the anti-cancer immunotherapy is administered to the subject at least 5, 10, 15, 20, 25, 30, 35, 40, 45, 50, 55, 60, 65, 70, 75, 80, 85, 90 minutes, 2, 3, 4, 5, 6, 7, 8, 9, 10, 11, 12, 13, 14, 15, 16, 17, 18,19, 20, 21, 22, 23, 24, 25, 26, 27, 28, 29, 30, 32, 35, 36, 40, 42, 45, 48 hours, 3, 4, 5, 6, 7, 8, 9, 10, 11, 12, 13, 14, 15, 16, 17, 18, 19, 20, 21, 22, 23, 24, 25, 26, 27, 28, 29, 30, 31, 45, 58, 59, 60, 61 days, 3, 4, 5, 6, 7, 8, 9, 10, 11 or 12 months following administration of the modified DAP12.

19. A method of promoting activation of dendritic cells comprising contacting a dendritic cell with the modified DAP12 of claim 1.

20. A method of inducing maturation of dendritic cells comprising contacting a dendritic cell with the modified DAP12 of claim 1.

21. A method of activating T cells comprising contacting the T cells with the modified DAP12 of claim 1.

22. A method of stimulating the proliferation of T cells comprising contacting the T cells with the modified DAP12 of claim 1.

23. A method of enhancing an anti-cancer immunotherapy in a subject with melanoma comprising administering to the subject the modified DAP12 of claim 1 at least 5, 10, 15, 20, 25, 30, 35, 40, 45, 50, 55, 60, 65, 70, 75, 80, 85, 90 minutes, 2, 3, 4, 5, 6, 7, 8, 9, 10, 11, 12, 13, 14, 15, 16, 17, 18, 19, 20, 21, 22, 23, 24, 25, 26, 27, 28, 29, 30, 32, 35, 36, 40, 42, 45, 48 hours, 3, 4, 5, 6, 7, 8, 9, 10, 11, 12, 13, 14, 15, 16, 17, 18, 19, 20, 21, 22, 23, 24, 25, 26, 27, 28, 29, 30, 31, 45, 58, 59, 60, 61 days, 3, 4, 5, 6, 7, 8, 9, 10, 11 or 12 months prior to administration of the anti-cancer immunotherapy.

\* \* \* \* \*